US011851478B2

(12) United States Patent
Crowe, Jr.

(10) Patent No.: US 11,851,478 B2
(45) Date of Patent: Dec. 26, 2023

(54) ANTIBODY-MEDIATED NEUTRALIZATION OF CHIKUNGUNYA VIRUS

(71) Applicant: Vanderbilt University, Nashville, TN (US)

(72) Inventor: James E Crowe, Jr., Nashville, TN (US)

(73) Assignee: VANDERBILT UNIVERSITY, Nashville, TN (US)

(*) Notice: Subject to any disclaimer, the term of this patent is extended or adjusted under 35 U.S.C. 154(b) by 663 days.

(21) Appl. No.: 16/959,760

(22) PCT Filed: Jan. 4, 2019

(86) PCT No.: PCT/US2019/012313
§ 371 (c)(1),
(2) Date: Jul. 2, 2020

(87) PCT Pub. No.: WO2019/156758
PCT Pub. Date: Aug. 15, 2019

(65) Prior Publication Data
US 2021/0009662 A1 Jan. 14, 2021

Related U.S. Application Data

(60) Provisional application No. 62/614,010, filed on Jan. 5, 2018.

(51) Int. Cl.
| | | |
|---|---|---|
| *A61P 31/14* | (2006.01) | |
| *A61K 39/42* | (2006.01) | |
| *C07K 16/10* | (2006.01) | |
| *G01N 33/569* | (2006.01) | |
| *A61K 39/00* | (2006.01) | |

(52) U.S. Cl.
CPC .......... *C07K 16/1081* (2013.01); *A61K 39/42* (2013.01); *A61P 31/14* (2018.01); *G01N 33/56983* (2013.01); *A61K 2039/505* (2013.01); *C07K 2317/24* (2013.01); *C07K 2317/56* (2013.01); *C07K 2317/565* (2013.01); *C07K 2317/76* (2013.01)

(58) Field of Classification Search
CPC ............ A61K 39/42; A61K 2039/505; G01N 33/56983; C07K 2317/56; C07K 2317/565; C07K 2317/76
See application file for complete search history.

(56) References Cited

U.S. PATENT DOCUMENTS

| | | |
|---|---|---|
| 9,441,032 B2 | 9/2016 | Warter et al. |
| 9,738,704 B2 | 8/2017 | Warter et al. |
| 2013/0189279 A1 | 7/2013 | Warter et al. |
| 2018/0127487 A1 | 5/2018 | Carter et al. |

FOREIGN PATENT DOCUMENTS

| | | |
|---|---|---|
| WO | WO 2011/124635 | 10/2011 |
| WO | WO 2015/010125 | 1/2015 |
| WO | WO 2016/168417 | 10/2016 |

OTHER PUBLICATIONS

Bréhin et al., "Production and characterization of mouse monoclonal antibodies reactive to Chikungunya envelope E2 glycoprotein." *Virology*, 371(1): 185-195, 2008.
Chu et al., "Deciphering the protective role of adaptive immunity to CHIKV/IRES a novel candidate vaccine against Chikungunya in the A129 mouse model." *Vaccine*, 31(33):3353-3360, 2013.
Chua et al., "Characterization of mouse monoclonal antibodies targeting linear epitopes on Chikungunya virus E2 glycoprotein." *Journal of Virological Methods*, 195: 126-133, 2014.
Coudere et al., "Prophylaxis and therapy for Chikungunya virus infection." *The Journal of Infectious Diseases*, 200(4): 516-523, 2009.
Extended European Search Report issued in European Application No. 16780715.5, dated Dec. 19, 2018.
Fong et al., "Exposure of epitope residues on the outer face of the chikungunya virus envelope trimer determines antibody neutralizing efficacy." *Journal of Virology*, JVI-01943, 2014.
Eric et al., "Use of human monoclonal antibodies to treat Chikungunya virus infection." *The Journal of Infectious Diseases*, 207(2): 319-322, 2012.
Goh et al., "Monoclonal antibodies specific for the capsid protein of chikungunya virus suitable for multiple applications," *Journal of General Virology*, 96 (3): 507-512, 2015.
Goh et al., "Neutralizing monoclonal antibodies to the E2 protein of chikungunya virus protects against disease in a mouse model," *Clinical Immunology*, 149(3): 487-497, 2013.
Hallengärd et al., "Prime-boost immunization strategies against Chikungunya virus." *Journal of Virology*, JVI-01926, 2014.
Hawman et al., "Chronic joint disease caused by persistent Chikungunya virus infection is controlled by the adaptive immune response." *Journal of Virology*, JVI-02666, 2013.
International Preliminary Report on Patentability issued in corresponding PCT Application No. PCT/US2019/012313, dated Jul. 16, 2020.
International Search Report and Written Opinion issued in corresponding PCT Application No. PCT/US2019/012313, dated Aug. 23, 2019.
International Search Report and Written Opinion issued in International Application No. PCT/US2016/027466, dated Oct. 7, 2016.
Invitation to Pay Additional Fees issued in International Application No. PCT/US2016/027466, dated Jun. 24, 2016.
Kam et al., "Early neutralizing IgG response to Chikungunya virus in infected patients targets a dominant linear epitope on the E2 glycoprotein." *EMBO Molecular Medicine*, 4(4): 330-343, 2012.

(Continued)

*Primary Examiner* — Janet L Andres
*Assistant Examiner* — Ruixue Wang
(74) *Attorney, Agent, or Firm* — Parker Highlander PLLC

(57) ABSTRACT

The present disclosure is directed to antibodies binding to and neutralizing Chikungunya virus (CHIKV) and methods for use thereof.

27 Claims, 27 Drawing Sheets
Specification includes a Sequence Listing.

(56) References Cited

OTHER PUBLICATIONS

Kam et al., "Longitudinal analysis of the human antibody response to chikungunya virus infection: implications for sero-diagnosis assays and vaccine development." *Journal of Virology*, JVI-01780, 2012.
Kielian et al., "Alphavirus entry and membrane fusion," *Viruses*, 2(4): 796-825, 2010.
Lee et al., "Chikungunya virus neutralization antigens and direct cell-to-cell transmission are revealed by human antibody-escape mutants." *PLoS Pathogens*, 7(12): e1002390, 2011.
Lum et al., "An essential role of antibodies in the control of Chikungunya virus infection." *The Journal of Immunology*, 1300304, 2013.
Masrinoul et al., "Monoclonal antibody targeting chikungunya virus envelope 1 protein inhibits virus release." *Virology*, 464:111-117, 2014.
Office Communication issued in corresponding Chilean Application No. 201702596, dated May 29, 2019. Original—English Translation provied below.
Office Communication issued in corresponding Chilean Application No. 201702596, dated May 29, 2019. English Machine Translation.
Office Communication issued in corresponding Eurasian Application No. 201792220, dated Mar. 26, 2019.
Office Communication issued in corresponding Eurasian Application No. 201792220/28, dated Dec. 17, 2019. English Translation with Original.
Office Communication issued in corresponding Japanese Application No. 2017-553887, dated Mar. 17, 2020. English Translation with Original.
Office Communication issued in corresponding Ukraine Application No. a 2017 11061, dated Feb. 10, 2021. English Translation.
Padlan et al., "Anatomy of the antibody molecule." *Molecular immunology*, 31(3): 169-217, 1994.
Pal et al., "Chikungunya viruses that escape monoclonal antibody therapy are clinically attenuated, stable, and not purified in mosquitoes." *Journal of Virology*, JVI-01032, 2014.
Pal et al., "Development of a highly protective combination monoclonal antibody therapy against Chikungunya virus." *PLoS Pathogens*, 9(4): e1003312, 2013.
Schilte et al., "Chikungunya virus-associated long-term arthralgia: a 36-month prospective longitudinal study." *PLoS Neglected Tropical Diseases*, 7(3): e2137, 2013.
Search Report and Written Opinion issued in Singapore Application No. 11201708152S, dated Oct. 9, 2018.
Selvarajah et al., "A neutralizing monoclonal antibody targeting the acid-sensitive region in chikungunya virus E2 protects from disease." *PLoS Neglected Tropical Diseases*, 7(9): e2423, 2013.
Sissoko et al., "Post-epidemic Chikungunya disease on Reunion Island: course of rheumatic manifestations and associated factors over a 15-month period." *PLoS Neglected Tropical Diseases*, 3(3): e389, 2009.
Smith et al., "Isolation and characterization of broad and ultrapotent human monoclonal antibodies with therapeutic activity against chikungunya virus." *Cell Host & Microbe*, 18(1): 86-95, 2015.
Staples et al., "Chikungunya fever: an epidemiological review of a re-emerging infectious disease." *Clinical Infectious Diseases*, 49 (6): 942-948, 2009.
Supplementary European Search Report issued in European Application No. 16780715.5, dated Oct. 8, 2018.
Warter et al., "Chikungunya virus envelope-specific human monoclonal antibodies with broad neutralization potency." *The Journal of Immunology*, 186(5):3258-64, 2011.

| Plate 1 | 1 | 2 | 3 | 4 | 5 | 6 | 7 | 8 | 9 | 10 | 11 | 12 |
|---|---|---|---|---|---|---|---|---|---|---|---|---|
| A | 0.4 | 1.1 | 0.3 | 1.4 | 0.4 | 1.0 | 0.8 | 0.3 | 0.9 | 0.3 | 0.5 | 1.1 |
| B | 1.5 | 0.5 | 0.9 | 1.5 | 0.3 | 0.3 | 1.5 | 0.3 | 0.2 | 0.6 | 0.6 | 0.3 |
| C | 1.3 | 1.7 | 1.3 | 2.3 | 1.6 | 1.7 | 0.4 | 1.3 | 0.7 | 0.4 | 0.4 | 0.8 |
| D | 1.9 | 2.1 | 2.5 | 0.5 | 0.2 | 1.9 | 0.6 | 0.5 | 0.2 | 0.7 | 1.7 | 0.5 |
| E | 1.0 | 2.3 | 0.4 | 1.5 | 1.4 | 0.6 | 0.9 | 2.1 | 2.5 | 0.7 | 0.5 | 2.0 |
| F | 2.1 | 0.4 | 2.0 | 1.1 | 1.1 | 0.4 | 1.8 | 1.7 | 0.3 | 1.7 | 0.9 | 2.0 |
| G | 0.4 | 1.8 | 2.0 | 0.6 | 0.4 | 1.9 | 0.6 | 1.7 | 1.2 | 0.7 | 2.3 | 1.7 |
| H | 1.5 | 0.6 | 0.7 | 1.5 | 0.7 | 2.6 | 1.1 | 0.7 | 2.5 | 1.4 | 0.9 | 0.9 |

FIG. 2

| Plate 2 | 1 | 2 | 3 | 4 | 5 | 6 | 7 | 8 | 9 | 10 | 11 | 12 |
|---------|---|---|---|---|---|---|---|---|---|----|----|----|
| A | 0.6 | 2.6 | 2.4 | 0.4 | 0.4 | 1.4 | 0.9 | 1.5 | 1.3 | 1.9 | 0.5 | 1.4 |
| B | 0.9 | 0.4 | 0.5 | 1.6 | 0.9 | 0.3 | 0.4 | 1.9 | 0.3 | 1.6 | 0.6 | 0.4 |
| C | 1.3 | 1.4 | 0.5 | 0.5 | 1.7 | 0.7 | 1.8 | 0.4 | 0.4 | 0.2 | 1.0 | 0.5 |
| D | 2.2 | 1.4 | 0.7 | 2.0 | 1.8 | 1.8 | 0.9 | 1.0 | 0.3 | 1.3 | 0.3 | 0.5 |
| E | 0.5 | 0.5 | 0.8 | 1.8 | 0.7 | 1.0 | 0.3 | 0.4 | 1.1 | 0.5 | 0.4 | 2.1 |
| F | 1.7 | 1.3 | 1.2 | 0.7 | 0.5 | 0.5 | 0.6 | 0.5 | 0.5 | 0.3 | 1.5 | 0.9 |
| G | 0.8 | 0.8 | 0.5 | 0.5 | 1.1 | 0.8 | 0.7 | 2.1 | 1.0 | 2.3 | 0.6 | 0.7 |
| H | 1.7 | 0.9 | 0.4 | 1.2 | 2.3 | 1.5 | 1.0 | 2.6 | 1.8 | 1.5 | 1.6 | 2.6 |

FIG. 2 (Cont'd)

| Plate 3 | 1 | 2 | 3 | 4 | 5 | 6 | 7 | 8 | 9 | 10 | 11 | 12 |
|---|---|---|---|---|---|---|---|---|---|---|---|---|
| A | 1.6 | 0.4 | 1.7 | 2.2 | 1.4 | 1.8 | 0.5 | 0.3 | 1.6 | 2.1 | 0.3 | 0.3 |
| B | 2.0 | 2.3 | 0.4 | 2.3 | 1.9 | 1.3 | 1.5 | 1.3 | 0.4 | 0.6 | 1.5 | 0.7 |
| C | 0.7 | 1.6 | 1.3 | 1.0 | 1.0 | 0.5 | 0.6 | 1.5 | 1.8 | 0.5 | 0.4 | 0.4 |
| D | 0.8 | 0.5 | 0.5 | 0.4 | 0.8 | 2.1 | 1.3 | 0.6 | 2.0 | 0.3 | 0.3 | 1.4 |
| E | 1.3 | 2.5 | 2.2 | 1.5 | 0.4 | 0.4 | 1.2 | 0.4 | 1.2 | 1.4 | 0.8 | 0.5 |
| F | 0.6 | 0.8 | 2.2 | 0.7 | 0.6 | 0.4 | 0.3 | 2.2 | 2.0 | 0.9 | 0.7 | 0.7 |
| G | 0.6 | 1.5 | 0.6 | 0.5 | 0.4 | 2.1 | 0.4 | 2.4 | 2.4 | 0.5 | 0.5 | 1.5 |
| H | 0.8 | 1.9 | 0.6 | 2.2 | 0.4 | 0.9 | 0.5 | 1.7 | 1.3 | 0.5 | 0.7 | 0.9 |

FIG. 2 (Cont'd)

| Plate 4 | 1 | 2 | 3 | 4 | 5 | 6 | 7 | 8 | 9 | 10 | 11 | 12 |
|---|---|---|---|---|---|---|---|---|---|---|---|---|
| A | 2.0 | 1.6 | 1.0 | 0.4 | 1.3 | 2.3 | 0.8 | 0.3 | 0.4 | 0.7 | 0.4 | 1.5 |
| B | 1.7 | 1.8 | 1.1 | 0.9 | 0.8 | 1.5 | 1.5 | 1.7 | 0.6 | 2.2 | 1.2 | 1.3 |
| C | 0.4 | 0.5 | 1.1 | 2.0 | 2.0 | 1.5 | 1.7 | 1.8 | 0.8 | 1.8 | 0.7 | 0.5 |
| D | 0.7 | 0.4 | 2.0 | 2.6 | 1.6 | 0.7 | 0.7 | 1.6 | 0.4 | 0.4 | 1.0 | 0.5 |
| E | 2.7 | 2.4 | 0.4 | 2.2 | 2.3 | 1.7 | 0.5 | 0.8 | 0.7 | 1.7 | 0.5 | 0.9 |
| F | 0.3 | 1.1 | 0.5 | 0.4 | 1.5 | 0.4 | 1.4 | 0.6 | 1.9 | 2.4 | 1.9 | 0.3 |
| G | 0.3 | 0.4 | 0.4 | 0.6 | 0.5 | 0.9 | 1.3 | 1.3 | 1.5 | 2.5 | 0.6 | 0.3 |
| H | 0.3 | 0.5 | 0.4 | 0.3 | 0.4 | 0.8 | 0.6 | 0.7 | 1.3 | 0.4 | 0.3 | 0.4 |

FIG. 2 (Cont'd)

| Plate 1 | 1 | 2 | 3 | 4 | 5 | 6 | 7 | 8 | 9 | 10 | 11 | 12 |
|---|---|---|---|---|---|---|---|---|---|---|---|---|
| A | 0.2 | 0.9 | 0.2 | 0.3 | 0.3 | 0.3 | 0.2 | 0.2 | 0.2 | 0.2 | 0.2 | 0.2 |
| B | 0.2 | 0.2 | 0.2 | 0.2 | 0.2 | 0.2 | 0.3 | 0.2 | 0.2 | 0.2 | 0.2 | 0.2 |
| C | 0.2 | 2.0 | 0.3 | 1.7 | 0.3 | 0.5 | 0.2 | 0.3 | 0.4 | 0.5 | 0.3 | 0.5 |
| D | 0.3 | 0.3 | 0.4 | 0.4 | 0.2 | 0.6 | 0.5 | 0.4 | 0.2 | 0.3 | 0.3 | 0.6 |
| E | 1.2 | 0.4 | 0.3 | 1.2 | 1.8 | 0.3 | 1.4 | 0.3 | 0.5 | 0.6 | 0.2 | 0.2 |
| F | 0.3 | 0.2 | 2.1 | 0.3 | 0.2 | 0.3 | 0.3 | 0.3 | 0.2 | 0.2 | 0.3 | 0.2 |
| G | 0.2 | 0.3 | 0.8 | 0.3 | 0.3 | 0.6 | 0.3 | 0.3 | 0.3 | 0.3 | 0.7 | 0.3 |
| H | 0.5 | 0.4 | 0.4 | 1.6 | 0.4 | 0.3 | 0.3 | 0.3 | 0.3 | 0.3 | 0.4 | 0.4 |

FIG. 3

| Plate 2 | 1 | 2 | 3 | 4 | 5 | 6 | 7 | 8 | 9 | 10 | 11 | 12 |
|---|---|---|---|---|---|---|---|---|---|---|---|---|
| A | 0.3 | 2.9 | 0.3 | 0.3 | 0.3 | 0.4 | 0.3 | 1.5 | 0.3 | 0.4 | 0.4 | 0.3 |
| B | 0.5 | 0.3 | 0.3 | 0.3 | 0.5 | 0.2 | 0.3 | 0.3 | 0.3 | 2.0 | 0.3 | 0.3 |
| C | 1.0 | 0.4 | 0.4 | 0.5 | 0.4 | 0.7 | 0.2 | 0.3 | 0.2 | 0.2 | 0.2 | 0.3 |
| D | 1.0 | 0.5 | 1.0 | 0.3 | 0.3 | 2.5 | 0.3 | 1.3 | 0.2 | 0.4 | 0.2 | 0.3 |
| E | 0.3 | 0.4 | 0.4 | 0.4 | 0.2 | 0.2 | 0.3 | 0.9 | 0.3 | 0.4 | 0.3 | 0.4 |
| F | 1.8 | 0.3 | 0.3 | 0.3 | 0.3 | 0.3 | 0.6 | 0.2 | 0.3 | 0.2 | 2.0 | 0.2 |
| G | 0.3 | 1.2 | 0.4 | 0.3 | 0.3 | 0.3 | 0.3 | 3.1 | 0.3 | 0.3 | 0.6 | 0.3 |
| H | 1.1 | 0.4 | 0.3 | 0.4 | 0.7 | 0.4 | 0.3 | 0.5 | 0.3 | 0.3 | 1.8 | 1.3 |

*FIG. 3 (Cont'd)*

| Plate 3 | 1 | 2 | 3 | 4 | 5 | 6 | 7 | 8 | 9 | 10 | 11 | 12 |
|---|---|---|---|---|---|---|---|---|---|---|---|---|
| A | 0.6 | 0.3 | 0.5 | 2.2 | 1.3 | 1.3 | 0.5 | 0.3 | 0.4 | 1.7 | 0.3 | 0.3 |
| B | 0.4 | 0.5 | 0.3 | 0.3 | 0.8 | 0.3 | 1.6 | 0.4 | 0.4 | 0.4 | 0.2 | 0.3 |
| C | 0.3 | 0.3 | 0.2 | 0.3 | 0.6 | 0.3 | 0.3 | 0.4 | 0.3 | 0.3 | 0.5 | 0.3 |
| D | 1.1 | 0.2 | 0.4 | 0.3 | 1.1 | 0.5 | 0.3 | 0.8 | 1.0 | 0.3 | 0.3 | 0.2 |
| E | 0.3 | 3.4 | 3.5 | 0.2 | 0.5 | 0.3 | 0.4 | 0.3 | 0.9 | 0.4 | 0.4 | 0.4 |
| F | 0.4 | 0.4 | 0.5 | 0.5 | 0.7 | 0.3 | 0.2 | 1.0 | 2.2 | 0.3 | 0.4 | 0.3 |
| G | 0.3 | 0.3 | 0.3 | 0.4 | 0.3 | 0.9 | 0.3 | 0.3 | 0.4 | 0.9 | 0.3 | 1.3 |
| H | 1.1 | 0.5 | 0.4 | 0.4 | 0.3 | 0.3 | 0.3 | 0.3 | 0.4 | 0.3 | 0.9 | 0.7 |

*FIG. 3 (Cont'd)*

| Plate 4 | 1 | 2 | 3 | 4 | 5 | 6 | 7 | 8 | 9 | 10 | 11 | 12 |
|---|---|---|---|---|---|---|---|---|---|---|---|---|
| A | 0.3 | 0.3 | 0.3 | 0.3 | 0.2 | 0.7 | 0.5 | 0.3 | 0.2 | 0.2 | 0.3 | 0.3 |
| B | 2.2 | 0.3 | 1.2 | 0.3 | 0.2 | 0.3 | 0.2 | 0.3 | 0.4 | 0.3 | 0.5 | 1.5 |
| C | 0.2 | 0.2 | 0.3 | 2.4 | 1.7 | 0.3 | 1.9 | 0.6 | 0.3 | 0.5 | 0.3 | 0.3 |
| D | 0.7 | 0.2 | 1.3 | 3.4 | 0.3 | 0.3 | 0.3 | 2.0 | 0.3 | 0.3 | 0.4 | 0.3 |
| E | 0.9 | 2.7 | 0.3 | 0.5 | 0.3 | 0.5 | 0.3 | 0.6 | 0.6 | 1.1 | 0.3 | 0.9 |
| F | 0.2 | 0.2 | 1.5 | 0.3 | 2.2 | 0.3 | 0.4 | 0.3 | 1.1 | 0.6 | 0.3 | 0.2 |
| G | 0.2 | 1.6 | 0.3 | 0.6 | 0.3 | 0.3 | 0.4 | 1.0 | 1.6 | 0.3 | 0.3 | 0.4 |
| H | 0.2 | 0.4 | 0.3 | 0.2 | 1.8 | 0.3 | 0.4 | 1.3 | 0.3 | 0.3 | 0.2 | 0.2 |

*FIG. 3 (Cont'd)*

| Plate 1 | 1 | 2 | 3 | 4 | 5 | 6 | 7 | 8 | 9 | 10 | 11 | 12 |
|---|---|---|---|---|---|---|---|---|---|---|---|---|
| A | 0.3 | 0.7 | 0.2 | 0.3 | 0.3 | 0.2 | 0.2 | 0.2 | 0.4 | 0.2 | 0.3 | 0.2 |
| B | 0.2 | 0.2 | 0.2 | 0.2 | 0.2 | 0.2 | 0.2 | 0.2 | 0.2 | 0.2 | 0.2 | 0.2 |
| C | 0.2 | 0.3 | 0.3 | 0.2 | 0.3 | 0.3 | 0.2 | 0.2 | 0.3 | 0.2 | 0.3 | 0.2 |
| D | 0.3 | 0.2 | 0.3 | 0.3 | 0.2 | 0.3 | 0.3 | 0.4 | 0.2 | 0.3 | 0.3 | 0.3 |
| E | 0.2 | 0.3 | 0.3 | 0.4 | 1.6 | 0.2 | 0.8 | 0.3 | 0.4 | 0.3 | 0.2 | 0.2 |
| F | 0.3 | 0.2 | 1.5 | 0.3 | 0.2 | 0.3 | 0.3 | 0.3 | 0.2 | 0.2 | 0.3 | 0.2 |
| G | 0.2 | 0.3 | 0.3 | 0.2 | 0.2 | 0.2 | 0.3 | 0.3 | 0.2 | 0.3 | 1.1 | 0.3 |
| H | 0.4 | 0.3 | 0.4 | 0.3 | 0.3 | 0.3 | 0.3 | 0.3 | 0.3 | 0.3 | 0.3 | 0.2 |

FIG. 4

| Plate 2 | 1 | 2 | 3 | 4 | 5 | 6 | 7 | 8 | 9 | 10 | 11 | 12 |
|---|---|---|---|---|---|---|---|---|---|---|---|---|
| A | 0.3 | 1.9 | 0.3 | 0.2 | 0.2 | 0.8 | 0.2 | 0.2 | 0.3 | 0.3 | 0.3 | 0.2 |
| B | 0.3 | 0.3 | 0.2 | 0.3 | 0.2 | 0.2 | 0.2 | 2.3 | 0.3 | 2.0 | 0.3 | 0.3 |
| C | 0.2 | 0.3 | 0.3 | 0.4 | 0.3 | 0.5 | 0.2 | 0.2 | 0.2 | 0.2 | 0.2 | 0.3 |
| D | 0.3 | 0.3 | 0.6 | 0.2 | 0.4 | 0.2 | 0.3 | 1.1 | 0.2 | 0.3 | 0.2 | 0.2 |
| E | 0.2 | 0.3 | 0.3 | 0.3 | 0.4 | 0.2 | 0.3 | 1.3 | 0.2 | 0.2 | 0.3 | 0.2 |
| F | 0.2 | 0.2 | 0.4 | 0.3 | 0.4 | 0.2 | 0.6 | 0.2 | 0.3 | 0.2 | 0.7 | 0.2 |
| G | 0.3 | 0.3 | 0.4 | 0.3 | 0.3 | 0.2 | 0.3 | 2.8 | 0.3 | 0.3 | 0.3 | 0.3 |
| H | 0.7 | 0.4 | 0.2 | 0.3 | 0.3 | 0.3 | 0.3 | 0.3 | 0.3 | 0.2 | 0.3 | 1.0 |

FIG. 4 (Cont'd)

| Plate 3 | 1 | 2 | 3 | 4 | 5 | 6 | 7 | 8 | 9 | 10 | 11 | 12 |
|---|---|---|---|---|---|---|---|---|---|---|---|---|
| A | 0.2 | 0.2 | 0.4 | 0.2 | 1.2 | 0.3 | 0.4 | 0.2 | 0.3 | 0.5 | 0.3 | 0.3 |
| B | 0.3 | 0.3 | 0.3 | 0.3 | 0.6 | 0.3 | 0.3 | 0.3 | 0.3 | 0.3 | 0.3 | 0.2 |
| C | 0.2 | 0.3 | 0.2 | 0.2 | 0.4 | 0.3 | 0.2 | 0.4 | 0.2 | 0.2 | 0.6 | 0.2 |
| D | 0.3 | 0.2 | 0.3 | 0.2 | 0.5 | 0.5 | 0.2 | 0.3 | 0.3 | 0.3 | 0.2 | 0.2 |
| E | 0.2 | 1.6 | 2.8 | 0.2 | 0.2 | 0.2 | 0.3 | 0.3 | 0.3 | 0.2 | 0.3 | 0.5 |
| F | 0.3 | 0.3 | 0.5 | 0.4 | 0.2 | 0.4 | 0.2 | 0.2 | 0.4 | 0.2 | 0.3 | 0.2 |
| G | 0.3 | 0.2 | 0.3 | 0.3 | 0.2 | 0.4 | 0.3 | 0.3 | 0.3 | 0.3 | 0.2 | 0.3 |
| H | 0.4 | 0.4 | 0.3 | 0.4 | 0.3 | 0.2 | 0.3 | 0.3 | 0.3 | 0.3 | 0.7 | 0.3 |

*FIG. 4 (Cont'd)*

| Plate 4 | 1 | 2 | 3 | 4 | 5 | 6 | 7 | 8 | 9 | 10 | 11 | 12 |
|---|---|---|---|---|---|---|---|---|---|---|---|---|
| A | 0.3 | 0.3 | 0.3 | 0.3 | 0.2 | 0.4 | 1.2 | 0.3 | 0.3 | 0.2 | 0.3 | 0.5 |
| B | 0.9 | 0.3 | 1.0 | 0.3 | 0.2 | 0.3 | 0.2 | 0.3 | 0.4 | 0.2 | 0.5 | 0.3 |
| C | 0.2 | 0.2 | 0.4 | 0.2 | 0.3 | 0.3 | 0.2 | 0.3 | 0.3 | 0.5 | 0.3 | 0.4 |
| D | 0.3 | 0.2 | 1.4 | 3.7 | 0.3 | 0.4 | 0.3 | 1.5 | 0.3 | 0.3 | 0.4 | 0.3 |
| E | 0.4 | 0.3 | 0.2 | 0.5 | 0.2 | 1.2 | 0.7 | 0.5 | 0.8 | 0.4 | 0.3 | 0.4 |
| F | 0.2 | 0.2 | 0.3 | 1.7 | 2.0 | 0.2 | 0.3 | 0.3 | 1.8 | 0.3 | 0.3 | 0.2 |
| G | 0.2 | 0.4 | 0.9 | 0.3 | 0.3 | 0.3 | 0.3 | 0.3 | 0.4 | 0.3 | 0.3 | 0.3 |
| H | 0.2 | 0.4 | 0.3 | 0.2 | 0.3 | 0.3 | 0.5 | 0.3 | 0.3 | 0.4 | 0.3 | 0.2 |

FIG. 4 (Cont'd)

|  | Well | CHKV | MAYV | RRV |
|---|---|---|---|---|
| 1 | 1C2 | 1.7 | 2.0 | 0.3 |
| 2 | 1C4 | 2.3 | 1.7 | 0.2 |
| 3 | 1D3 | 2.5 | 0.4 | 0.3 |
| 4 | 1E2 | 2.3 | 0.4 | 0.3 |
| 5 | 1E5 | 1.4 | 1.8 | 1.6 |
| 6 | 1E9 | 2.5 | 0.5 | 0.4 |
| 7 | 1F3 | 2.0 | 2.1 | 1.5 |
| 8 | 1G11 | 2.3 | 0.7 | 1.1 |
| 9 | 1H6 | 2.6 | 0.3 | 0.3 |
| 10 | 1H9 | 2.5 | 0.3 | 0.3 |
| 11 | 2A2 | 2.6 | 2.9 | 1.9 |
| 12 | 2A3 | 2.4 | 0.3 | 0.3 |
| 13 | 2B10 | 1.6 | 2.0 | 2.0 |
| 14 | 2B8 | 1.9 | 0.3 | 2.3 |
| 15 | 2D1 | 2.2 | 1.0 | 0.3 |
| 16 | 2D4 | 2.0 | 0.3 | 0.2 |
| 17 | 2D6 | 1.8 | 2.5 | 0.2 |
| 18 | 2E12 | 2.1 | 0.4 | 0.2 |
| 19 | 2F11 | 1.5 | 2.0 | 0.7 |
| 20 | 2G10 | 2.3 | 0.3 | 0.3 |
| 21 | 2G8 | 2.1 | 3.1 | 2.8 |
| 22 | 2H12 | 2.6 | 1.3 | 1.0 |
| 23 | 2H5 | 2.3 | 0.7 | 0.3 |
| 24 | 2H8 | 2.6 | 0.5 | 0.3 |
| 25 | 3A10 | 2.1 | 1.7 | 0.5 |
| 26 | 3A4 | 2.2 | 2.2 | 0.2 |
| 27 | 3B1 | 2.0 | 0.4 | 0.3 |
| 28 | 3B2 | 2.3 | 0.5 | 0.3 |
| 29 | 3B4 | 2.3 | 0.3 | 0.3 |
| 30 | 3D6 | 2.1 | 0.5 | 0.5 |

FIG. 5

|    | Well | CHKV | MAYV | RRV |
|----|------|------|------|-----|
| 31 | 3D9  | 2.0  | 1.0  | 0.3 |
| 32 | 3E2  | 2.5  | 3.4  | 1.6 |
| 33 | 3E3  | 2.2  | 3.5  | 2.8 |
| 34 | 3F3  | 2.2  | 0.5  | 0.5 |
| 35 | 3F8  | 2.2  | 1.0  | 0.2 |
| 36 | 3F9  | 2.0  | 2.2  | 0.4 |
| 37 | 3G6  | 2.1  | 0.9  | 0.4 |
| 38 | 3G8  | 2.4  | 0.3  | 0.3 |
| 39 | 3G9  | 2.4  | 0.4  | 0.3 |
| 40 | 3H4  | 2.2  | 0.4  | 0.4 |
| 41 | 4A1  | 2.0  | 0.3  | 0.3 |
| 42 | 4A6  | 2.3  | 0.7  | 0.4 |
| 43 | 4B1  | 1.7  | 2.2  | 0.9 |
| 44 | 4B10 | 2.2  | 0.3  | 0.2 |
| 45 | 4C4  | 2.0  | 2.4  | 0.2 |
| 46 | 4C5  | 2.0  | 1.7  | 0.3 |
| 47 | 4D3  | 2.0  | 1.3  | 1.4 |
| 48 | 4D4  | 2.6  | 3.4  | 3.7 |
| 49 | 4D8  | 1.6  | 2.0  | 1.5 |
| 50 | 4E1  | 2.7  | 0.9  | 0.4 |
| 51 | 4E2  | 2.4  | 2.7  | 0.3 |
| 52 | 4E4  | 2.2  | 0.5  | 0.5 |
| 53 | 4E5  | 2.3  | 0.3  | 0.2 |
| 54 | 4F10 | 2.4  | 0.6  | 0.3 |
| 55 | 4F4  | 0.4  | 0.3  | 1.7 |
| 56 | 4F5  | 1.5  | 2.2  | 2.0 |
| 57 | 4F9  | 1.9  | 1.1  | 1.8 |
| 58 | 4G10 | 2.5  | 0.3  | 0.3 |

*FIG. 5*
*(Cont'd)*

Chik Mabs- MAYV

- ● hCHKV-4
- ■ hCHKV-8
- ▲ hCHKV-9
- ▼ hCHKV-12
- ◆ hCHKV-13
- ○ hCHKV-19
- □ hCHKV-22
- △ hCHKV-23
- ▽ hCHKV-24
- ◇ hCHKV-27
- ◈ hCHKV-29
- ★ hCHKV-31
- + hCHKV-32
- × hCHKV-35
- ⊙ hCHKV-50
- ⊡ hCHKV-53
- ◈ WNV hE16

FIG. 6 (Cont'd)

Second round of mAbs, CHKV-1 and -48

- ■ hCHKV-1
- ▼ hCHKV-48
- ▲ WNV hE16

FIG. 7

WNV hE16

- ■ LR (ESCA)
- ▲ Ross (ESCA)
- □ 99659 (Asian)
- ▼ AF15561 (Asian)
- △ 37997 (WA)
- ● IbH35 (WA)

FIG. 8
(Cont'd)

| Clone | Donor | Position on 384-well | Screening assay | | | | | |
|---|---|---|---|---|---|---|---|---|
| | | | Antigens used for ELISA | | | Neutralization assay | | |
| | | | CHKV | MAYV | RRV | CHKV | MAYV | RRV (1:2) |
| 24 | 891 | 2H8 | 2.6 | 0.5 | 0.3 | 100 | 12 | 0 |
| 35 | 891 | 3F8 | 2.2 | 1.0 | 0.2 | 100 | 41 | 15 |
| 27 | 891 | 3B1 | 2.0 | 0.4 | 0.3 | 97 | 0 | 1 |
| 8 | 891 | 1G11 | 2.3 | 0.7 | 1.1 | 100 | 29 | 19 |
| 12 | 891 | 2A3 | 2.4 | 0.3 | 0.3 | 100 | 9 | 18 |
| 29 | 891 | 3B4 | 2.3 | 0.3 | 0.3 | 97 | 0 | 4 |
| 32 | 891 | 3E2 | 2.5 | 3.4 | 1.6 | 95 | 89 | 0 |
| 53 | 891 | 4E5 | 2.3 | 0.3 | 0.2 | 100 | 0 | 3 |
| 31 | 891 | 3D9 | 2.0 | 1.0 | 0.3 | 87 | 10 | 11 |
| 50 | 891 | 4E1 | 2.7 | 0.9 | 0.4 | 97 | 24 | 11 |
| 4 | 891 | 1E2 | 2.3 | 0.4 | 0.3 | 99 | 0 | 7 |
| 9 | 891 | 1H6 | 2.6 | 0.3 | 0.3 | 98 | 11 | 3 |
| 13 | 891 | 2B10 | 1.6 | 2.0 | 2.0 | 91 | 48 | 12 |
| 19 | 891 | 2F11 | 1.5 | 2.0 | 0.7 | 82 | 66 | 11 |
| 22 | 891 | 2H12 | 2.6 | 1.3 | 1.0 | 95 | 17 | 6 |
| 23 | 891 | 2H5 | 2.3 | 0.7 | 0.3 | 100 | 15 | 6 |
| 1 | 891 | 1C2 | 1.7 | 2.0 | 0.3 | 80 | 66 | 4 |
| 48 | 891 | 4D4 | 2.6 | 3.4 | 3.7 | 95 | 41 | 70 |
| NC=No clone available | | | | | | | | |
| 2 | 891 | 1C4 | 2.3 | 1.7 | 0.2 | 100 | 61 | 15 |
| 3 | 891 | 1D3 | 2.5 | 0.4 | 0.3 | 100 | 0 | 17 |

*FIG. 9*

| IgG sent | Purified MAbs-FRNT results | | | | Apparent affinity |
|---|---|---|---|---|---|
| | IC50 value (ng/mL) | | | | |
| | CHIKV | MAYV | RRV | | |
| VIM458 | 4 | >10000 | | | High |
| VIM458 | 11 | >10000 | | | High |
| VIM458 | 17 | >10000 | | | High |
| VIM458 | 24 | >10000 | | | High |
| VIM458 | 25 | >10000 | | | High |
| VIM458 | 86 | >10000 | | | High |
| VIM458 | 81 | >10000 | | | High |
| VIM458 | 319 | >10000 | | | Low |
| VIM458 | 684 | >10000 | | | Low |
| VIM458 | 2266 | >10000 | | | High |
| VIM458 | >10000 | >10000 | | | Low |
| VIM458 | >10000 | >10000 | | | Low |
| VIM458 | >10000 | >10000 | | | Low |
| VIM458 | >10000 | >10000 | | | Low |
| VIM458 | >10000 | >10000 | | | Low |
| VIM458 | >10000 | >10000 | | | Low |
| VIM513 | >10000 | >10000 | | | Low |
| VIM513 | 37 | >10000 | | | |
| | | | | | |
| | | | | | |
| NC | | | | | |
| NC | | | | | |

*FIG. 9*
*(Cont'd)*

| 5 | 891 | 1E5 | 1.4 | 1.8 | 1.6 | 66 | 57 | 13 |
|---|---|---|---|---|---|---|---|---|
| 6 | 891 | 1E9 | 2.5 | 0.5 | 0.4 | 100 | 15 | 6 |
| 7 | 891 | 1F3 | 2.0 | 2.1 | 1.5 | 99 | 79 | 6 |
| 10 | 891 | 1H9 | 2.5 | 0.3 | 0.3 | 100 | 0 | 0 |
| 11 | 891 | 2A2 | 2.6 | 2.9 | 1.9 | 99 | 95 | 74 |
| 14 | 891 | 2B8 | 1.9 | 0.3 | 2.3 | 99 | 21 | 15 |
| 15 | 891 | 2D1 | 2.2 | 1.0 | 0.3 | 100 | 40 | 0 |
| 16 | 891 | 2D4 | 2.0 | 0.3 | 0.2 | 99 | 10 | 0 |
| 17 | 891 | 2D6 | 1.8 | 2.5 | 0.2 | 97 | 97 | 2 |
| 18 | 891 | 2E12 | 2.1 | 0.4 | 0.2 | 99 | 22 | 2 |
| 20 | 891 | 2G10 | 2.3 | 0.3 | 0.3 | 96 | 2 | 0 |
| 21 | 891 | 2G8 | 2.1 | 3.1 | 2.8 | 75 | 64 | 18 |
| 25 | 891 | 3A10 | 2.1 | 1.7 | 0.5 | 100 | 27 | 9 |
| 26 | 891 | 3A4 | 2.2 | 2.2 | 0.2 | 99 | 94 | 3 |
| 28 | 891 | 3B2 | 2.3 | 0.5 | 0.3 | 100 | 0 | 10 |
| 30 | 891 | 3D6 | 2.1 | 0.5 | 0.5 | 91 | 0 | 5 |
| 33 | 891 | 3E3 | 2.2 | 3.5 | 2.8 | 92 | 82 | 5 |
| 34 | 891 | 3F3 | 2.2 | 0.5 | 0.5 | 100 | 0 | 19 |
| 36 | 891 | 3F9 | 2.0 | 2.2 | 0.4 | 97 | 32 | 19 |
| 37 | 891 | 3G6 | 2.1 | 0.9 | 0.4 | 99 | 41 | 16 |
| 38 | 891 | 3G8 | 2.4 | 0.3 | 0.3 | 100 | 1 | 14 |
| 39 | 891 | 3G9 | 2.4 | 0.4 | 0.3 | 100 | 7 | 15 |
| 40 | 891 | 3H4 | 2.2 | 0.4 | 0.4 | 71 | 14 | 26 |

*FIG. 9*
*(Cont'd)*

| NC | | | | | |
|----|--|--|--|--|--|
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |

*FIG. 9*
*(Cont'd)*

| 41 | 891 | 4A1 | 2.0 | 0.3 | 0.3 | 89 | 16 | 18 |
| --- | --- | --- | --- | --- | --- | --- | --- | --- |
| 42 | 891 | 4A6 | 2.3 | 0.7 | 0.4 | 85 | 5 | 13 |
| 43 | 891 | 4B1 | 1.7 | 2.2 | 0.9 | 89 | 92 | 19 |
| 44 | 891 | 4B10 | 2.2 | 0.3 | 0.2 | 90 | 2 | 0 |
| 45 | 891 | 4C4 | 2.0 | 2.4 | 0.2 | 84 | 43 | 2 |
| 46 | 891 | 4C5 | 2.0 | 1.7 | 0.3 | 97 | 19 | 0 |
| 47 | 891 | 4D3 | 2.0 | 1.3 | 1.4 | 97 | 25 | 5 |
| 49 | 891 | 4D8 | 1.6 | 2.0 | 1.5 | 97 | 12 | 14 |
| 51 | 891 | 4E2 | 2.4 | 2.7 | 0.3 | 95 | 28 | 9 |
| 52 | 891 | 4E4 | 2.2 | 0.5 | 0.5 | 100 | 1 | 0 |
| 54 | 891 | 4F10 | 2.4 | 0.6 | 0.3 | 86 | 2 | 17 |
| 55 | 891 | 4F4 | 0.4 | 0.3 | 1.7 | 69 | 5 | 30 |
| 56 | 891 | 4F5 | 1.5 | 2.2 | 2.0 | 82 | 95 | 20 |
| 57 | 891 | 4F9 | 1.9 | 1.1 | 1.8 | 98 | 27 | 34 |
| 58 | 891 | 4G10 | 2.5 | 0.3 | 0.3 | 100 | 0 | 6 |
| 59 | 891 | 4E10 | 1.7 | 1.1 | 0.4 | 92 | 83 | 0 |

FIG. 9
(Cont'd)

| | | | | | |
|---|---|---|---|---|---|
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |
| NC | | | | | |

*FIG. 9*
*(Cont'd)*

SEQUENCE LISTING

<160> NUMBER OF SEQ ID NOS: 220

<210> SEQ ID NO 1
<211> LENGTH: 315
<212> TYPE: DNA
<213> ORGANISM: Artificial sequence
<220> FEATURE:
<223> OTHER INFORMATION: Synthetic oligonucleotide

<400> SEQUENCE: 1

```
tcctatgagc tgactcagcc accctcagtg tccgtgtctg caggacagac agccaccatc      60
acctgctctg gagataaatt gggggataaa tatgcttgct ggtatcagca gaagccaggc     120
cagtcccctg tgctggtcat ctatcaagat agccaacggc cctcagggat ccctgagcga     180
ttctctggct ccaactctgg gaacacagcc actctgacca tcagcgggac ccaggctatg     240
gatgaggctg actattactg tcaggcgtgg gacagcagcg tggtattcgg cggagggacc     300
aagctgaccg tccta                                                      315
```

<210> SEQ ID NO 2
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 2

```
caggtgcagc tggtggagtc gggggggaggc gtggtccagc ctgggaggtc cctgagactc      60
tcctgtgcag cctcagaatc caccttcagc ggctatgcta tgcactgggt ccgccaggct     120
ccaggcaagg ggctggagtg ggtggcagtc acatcatatg atggaagtag taactactac     180
gcagactccg tgaggggccg attcaccatt ttgagagaca tttccaagaa cacgctgttt     240
ctgcaaatga acagcctgag agctgaggac acggctgtct attactgtgt gagggaatat     300
tacggtctgg atgtctgggg ccagggacc ctggtcaccg tctcctca                   348
```

<210> SEQ ID NO 3
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 3

```
gacatccaga tgacccagtc tccatccttc ctgtctgcat ctgtaggaga cagagtcacc      60
atcacttgcc gggccagtca gggcattagc cgttatttag cctggtatca gcaaaaacca     120
gggaaagccc ctaaactcct gatgtctgtt ccatccactt tacaaagtgg ggtcccatca     180
```

```
aggttcagcg gcagtggatc tgggacagaa ttcactctca caatcagcag cctacagcct    240
gaagattttg caacttatta ctgtcaacac cttaatggtt acccgtactc tttcggcgga    300
gggaccaagg tggagatcaa a                                              321

<210> SEQ ID NO 4
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 4
caggtccagc tggtacagtc tggggctgag gtgaagaagc ctggggcctc agtgaaggtc     60
tcctgcaagg tttccggata caccctcact gacttatcca tgcactgggt gcgacaggcc    120
cctggaaaag gcttgagtg gatgggaggt tttgatcctg aagatagtga acaatctac     180 gcacagaagt tccagggcag agtcaccatg accgaggaca tctacagata cagcctac     240 atggagctga gcagcctgag atctgacgac acggccgtct attactgtgc aacagaaaat    300
ttcgatactt taattggtca ttataaattt gacttctggg gccagggaac cctggtcacc    360
gtctcctca                                                            369

<210> SEQ ID NO 5
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 5
gacatccaga tgacccagtc tccatcgtcc ctgtctgcat ctgtaggaga cagagtcacc     60
atcacttgcc aggcgagtca agacattagc aactatttaa attggtatca gcagaaacca    120
gggaaagccc ctaacctcct gatccacgat gcatccaatt tggaaacagg gtcccatcc     180 aggttcagtg gaagtggatc tgggacacat tttactctca ccatcagcag cctgcagcct    240
gaagatattg caacatatta ctgtcaacag tatgataatc ccctcgaac tttcggccct     300 gggaccaaag tggatatcaa a                                              321

<210> SEQ ID NO 6
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 6
gaagtgcagc tggtggagtc tgggggaggc ttggtacagc ctggcaggtc cctgagactc     60
tcctgtgcag cctctggatt caccttttgat gattatgcca tgcactgggt ccggcaaggt   120
ccagggaagg gctggagtg gtctcagga attagttgga aaagtggcag tataggctat       180
gcggactctg tgaagggtcg attcaccatc accagagaca cgccaaaaa gtccctatat    240 ctgcaaatga acagtctgag agctgaggac acggccttgt attactgtac aaaagacgcg    300
atcccgtcat attgtgatag tatcagctgc tataggcga atgggaacta cgactttttc    360
ggtatggacg cctggggcca agggaccctg gtcaccgtct cctca                    405
```

```
<210> SEQ ID NO 7
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 7
gacatccaga tgacccagtc tccatcgtcc ctgtctgcat ctgtaggaga cagagtcacc    60
atcacttgcc aggcgagtca agacattagc aactatttaa attggtatca gcagaaacca   120
gggaaagccc ctaacctcct gatccacgat gcatccaatt tggaaacagg ggtcccatcc   180
aggttcagtg gaagtggatc tgggacacat tttactctca ccatcagcag cctgcagcct   240
gaagatattg caacatatta ctgtcaacag tatgataatc tccctcgaac tttcggccct   300
gggaccaaag tggatatcaa a                                             321

<210> SEQ ID NO 8
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 8
gaggtgcagc tggtggagtc cgggggaggc ttggtccagc cggggaagtc cctgagactc    60
tcctgtgcag cctctggagt caccttagt ggttttcgga tgagctgggt ccgccaggct   120
cccgggaagg ggctggagtg ggtggccgac attaaccaag atggaagtga gacgtactat   180
gtggactctg tgaagggccg attcaccatc tccagagaca acgccaagaa ctcagtgttt   240
ctgctactga acagtctgag agccgtggac acggctgttt attactgtgc gagagtggtg   300
ggccttgttg cttttgatgt ctgggccaa gggaccctgg tcaccgtctc ctca          354

<210> SEQ ID NO 9

<400> SEQUENCE: 9

000

<210> SEQ ID NO 10
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 10
gaagtgcagc tggtggagtc tggggggaggc ttggttcagc ctggcaggtc cctgagactc   60
tcctgtgcag cctctggatt catgtttgat gattgtgcca tgcactgggt ccggcaagct   120
ccagggaagg gcctggagtg ggtctcaggt attaattggg atagtgctag aatagactat   180
gcggcctctc tgaagggccg attcaccata tccagagaca acgccaggaa ctccctatat   240
ctgcaaatga acagtctgcg acctgaggac acggccttgt attactgtgt aaaagcctcg   300
gaccgtggat atactggcta cgacacctct tttgactact ggggccaggg aaccctggtc   360
accgtctcct ca                                                       372

<210> SEQ ID NO 11
<211> LENGTH: 330
<212> TYPE: DNA
<213> ORGANISM: Artificial sequence
```

```
<220> FEATURE:
<223> OTHER INFORMATION: Synthetic oligonucleotide

<400> SEQUENCE: 11
cagtctgtgc tgactcagcc accctcagcg tctgggaccc ccgggcagag ggtcaccatc    60
tcttgttctg gaagcagctc caacatcgga aggaatactg taaactggta ccagcaactc   120
ccaggaacgc cccccaaact cctcacctat agtaataatc agcggccctc agggtccct    180 gaccgattct ctggctccaa gtctggcacc tcagcctccc tggccatcag tgggctgcag   240
tctgaggatg aggctgatta ttactgtgca gcatgggatg acagcctgag tgggtatgtc   300
ttcggaactg ggaccaaggt caccgtccta                                     330

<210> SEQ ID NO 12
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 12
gaggtgcagc tggtggagtc tgggggagac ctggtacagc cggggggtc cctgagactc     60 tcctgtgtag cctctggatt cagttttagt aactttgcca tgagctgggt ccgccaggct   120
ccagggaagg ggctggagtg ggtcgcagga attagtggta gtggatctag cacataccat   180
gcggccgccg tgcagggccg gttcaccatc tccagagaca attccaagaa tacactgtat   240
ctgcaaatgg acagcctgag agtcgacgac atggccatat attattgtac gaaagatgca   300
gagaatcagt tgctatattg gttcgacccc tggggccagg gaaccctggt caccgtctcc   360
tca                                                                 363

<210> SEQ ID NO 13
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 13
gacatccaga tgacccagtc tccatcctcc ctgtcttcat ctgtaggaga cagaatcaca     60
atcacttgcc gggcaagtcg gagcatcagt atgtatgtaa attggtatgt ccagagacca   120
gggcacgccc caaagctcct catctatgct gcatccactt tgcaaactgg agtcccgtca   180
aggttcagtg gcagtggatc tgggacagat ttcactctca ccatcagcag tctgcaacct   240
gaagattttg caatttacta ctgtcaacag acttacacta cccgacgtt cggccagggg    300 accaaggtgg aaatcaaa                                                 318

<210> SEQ ID NO 14
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 14
caggtgcagc tgcaggagtc gggcccagga ctggtgaagc cttcggggac tctgtccctc     60
agctgcgctg tctctggtgg ctccatcagt agttatgact ggtggagttg ggtccgccag   120
ttcccaggaa aggggctgga gtggattggg gaaatctatc atagtgggag caccaattac   180
```

```
aacccgtccc tcaagagtcg agtcaccatt tcagtagaca agtccaacaa ccagttctcc    240
ctgaacctga cctctgtgac cgccgcggac acggccgtct attactgtgc gagaggcaat    300
ttacaacgcc ccggggtcta cttcggtttg gacgtctggg gcccagggac cctggtcacc    360
gtctcctca                                                            369
```

```
<210> SEQ ID NO 15
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 15
cagtctgccc tgactcagcc tccctccgcg tccgggtctc ctggacagtc agtcaccatc     60
tcctgcactg gaaccagcag tgacgttggt ggttataaat atgtctcctg gtaccaacag    120
tacccaggca agcccccac actcataatt tatgaggtca ctgaacggcc ctcaggggtc     180
cctgatcgct tctctggctc caagtctggc aacacggcct ccctgaccgt ctctgggctc    240
caggctgagg atgaggctga ttattactgc agctcctatg ccgccaacaa caatttgctt    300
ttcggcggag ggaccaagct gaccgtccta                                     330
```

```
<210> SEQ ID NO 16
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 16
caggtgcagc tgcaggagtc gggcccagga ctggtgaagc cttcggggac tctgtccctc     60
agctgcgctg tctctggtgg ctccatcagt agttatgact ggtggagttg ggtccgccag    120
ttcccaggaa aggggctgga gtggattggg gaaatctatc atagtgggag caccaattac    180
aacccgtccc tcaagagtcg agtcaccatt tcagtagaca agtccaacaa ccagttctcc    240
ctgaacctga cctctgtgac cgccgcggac acggccgtct attactgtgc gagaggcaat    300
ttacaacgcc ccggggtcta cttcggtttg gacgtctggg gcccagggac cctggtcacc    360
gtctcctca                                                            369
```

```
<210> SEQ ID NO 17
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 17
cagtctgtgc tgactcagcc accctcagcg tctgggaccc ccgggcagag agtcagcatt     60
gcttgttctg gaggcagctt caacatcgaa ataactatc tttcctggta ccaacaagtc    120
ccaggaacgg cccccaaact cctcatctat cacaatgatc agcggccctc agaagtccct    180
gaccgattct ctgcctccag gtctggcccc tcagcctccc tggccatcag tgggctccgg    240
tccgaggatg aggctcatta ttactgtgca acatgggatg acagtctgag tggttgggtg    300
ttcggcggag ggaccaagtt gaccgtcctg                                     330
```

<210> SEQ ID NO 18
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 18

```
caggtgcagc tgcaggagtc gggcccagga ctggtgaagc cttcggggac cctgtccctc      60
acctgcgctg tctctggtgg ctccatcagt agtagttcgt ggtggagttg ggtccgccag     120
cccccaggga aggggctgga atggattgga gaaatctatt ggagtgggag aaccaactac     180
aacccgtccc tcaggagtcg agtcaccata tcagtagaca gtccaagaac cagttctcc     240
ctgacgctga tctctgtgac cgccgcggac acggccgtgt attactgtgc aaaaactccg     300
gatactgcta tgggcgagga tgttttttgat atctggggcc aagggaccct ggtcaccgtc     360
tcctca                                                                 366
```

<210> SEQ ID NO 19
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 19

```
cagtctgtgc tgactcagcc accctcagcg tctgggaccc ccgggcagac agtcaccatc      60
tcttgttctg gaagcaactc caacctcgga agtaattatg tagtctggta ccagcaggtc     120
ccaggaacgg cccccaaact cctcatctat aggaataatc agcgccctc cggggtctct     180
gaccgattct ctggctccaa gtctggcacc tcagcctccc tggccatcag tgggctccgg     240
tccgaggatg aggctgatta tcactgtgca acatgggatg acagcctgag tggtcgggtg     300
ttcggcggag gaaccaaact gaccgtccta                                      330
```

<210> SEQ ID NO 20
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 20

```
caggtgcagc tggtggagtc tgggggaggc gtggtccagc ctgggaagtc cctgagactc      60
tcctgtgcag cctctggatt caccttccgt aactatggca tgcactgggt ccgccaggct     120
ccaggcaagg ggctggactg ggtggcactt atatcatatg atggaactca taagtactat     180
aaagactccc tgaagggccg attcaccatc tccagagaca atttccagaa cacagtagat     240
ctgcaaatca acagcctgag acctgacgac acggctgtct attactgtgc gaaagaactt     300
gcgacttccg gagtggttga acctcttgac tcctggggcc agggaaccct ggtcaccgtc     360
tcctca                                                                 366
```

<210> SEQ ID NO 21
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 21

```
gaaattgtgt tgacgcagtc tccaggcacc ctgtctttgt ctccagggga aagagccacc    60
ctctcctgca gggccagtca gagtcttgtc agcagctact tcggctggta ccaacagaag   120
cgtggccagt ctcccaggct cctcatctat gctgcatcca ccaggccac tggcatccca    180 gacaggttca gtggcagtgg gtctgggaca gacttcactc tcaccatcag cagactggag   240
cctgaagatt ttgcagtgta ttactgtcag cagtatggta acacaccttt cactttcggc   300
ggagggacca aggtggagat caaa                                          324
```

<210> SEQ ID NO 22
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 22

```
caggtccaac ttgtgcagtc tggggctgag gtgaagaagc ctggggcctc agtgaaggtt    60
tcctgcaagc cttctggata caacttcatt gactatgcta tgcattgggt gcgccaggcc   120
cccggacaaa ggcttgagtg gatgggatgg atcaacgccg ccaatgataa tagagaatat   180
tcacagaagt ttcagggcag agtcacccctt actcgggaca catccgcgac cacagcctac   240
atggagctga gcagcctgac atttgaagac acggctgtgt attactgtgc gagagatcgg   300
ggtactatgg ttcggggagt cggcggctgg ttcgacccct ggggccaggg aaccctggtc   360
accgtctcct ca                                                       372
```

<210> SEQ ID NO 23
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 23

```
tcctatgtgc tgactcagcc accctcggtg tcagtggccc caggagagac ggccaggatt    60
acctgtgggg gaaacaacat tggaagtaaa agtgtgcact ggtaccagca gaagccagtc   120
caggcccctg tggtggtcgt ctatgatgat agcgaccggc cctcaggat ccctgagcga    180 ttctctggct ccaactctgg gaacacggcc accctgacca tcagcagggt cgaagccggg   240
gatgaggccg actattactg tcaggtgtgg gatagtagta gtaatcatcc ggtgttcggc   300
ggagggacca aggtggccgt ccta                                          324
```

<210> SEQ ID NO 24
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 24

```
gaagtgcagc tggtggagtc tgggggagtc gtggtacagc ctgggggtc cctgagactc     60 tcctgtgcag cctctggatt caactttgat gattatacca tgcactgggt ccgtcaagct   120
ccggggaagg gcctggagtg ggtctctctt attacttggg atggtctcag cacatactat   180
gcagactcta tgaagggccg attcaccatc tccagagaca cagcaagga ctccctgtat    240 ctgcaaatgg acagtctgag aactgaggac accgccttct attattgtgt aagagatatg   300
```

```
gggcccgggg cagtccactt ctacttctac ggtatggacg tctggggcca agggaccctg    360
gtcaccgtct cctca                                                    375

<210> SEQ ID NO 25
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 25
cagtctgccc tgactcagcc tgcctccgtg tctgggtctc ctggacagtc gatcaccatc    60
tcctgcactg gaaccagcag tgatgttggg aattataacc ttgtctcctg gtaccaacaa   120
cacccaggca aagtccccaa actcatcatt tatgaggtca gtaagcggcc ctcaggggatt  180 tctaagcgct ctctctgcctc caagtctggc aacacggcct ccctgacaat ctctgggctc  240
caggctgagg acgaggctga ttattactgc tgctcatatg ctggtagtag cggggtgttc   300
ggcgcaggga ccaagctgac cgtcctc                                       327

<210> SEQ ID NO 26
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 26
gaggtgcagc tggtggagtc tgggggaggc ttggtacagc ctgggggggtc cctgagactc    60 tcctgtgcag cctctggatt cacctttagc aattatgcca tgagctgggt ccgccaggct   120
ccagggaagg ggctggagtg ggtctcaggc atcagtggaa gtggtagaac cacatactac   180
acagactccg tgaagggccg gttcaacatc tccagagaca acaccaagaa cacgctgttt   240
ctgcaaatga acagcctgag agccgaggac acggccgtat attattgtgt gaaagataga   300
gctggctggt tcgggaacta ctttgactac tgggggccagg gaaccctggt caccgtctcc   360
tca                                                                 363

<210> SEQ ID NO 27
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 27
gacatccaga tgacccagtc tccatcctca ctgtctgcat ctgtaggaga cagagtcacc    60
atcacttgtc gggcgagtca gggcattagc aattatttag cctggtttca gcagaaacca   120
gggaaagccc ctaagtccct gatctatgct gcatccagtt tgcaaagtgg ggtcccatca   180
aagttcagcg gcagtagatc tgggacaaat ttcactctca ccatcagcag cctgcagcct   240
gaagattttg caacttatta ctgccaacaa tataatactt accctccgac gttcggccaa   300
gggaccacgg tggaaatcaa a                                             321

<210> SEQ ID NO 28
<211> LENGTH: 366
<212> TYPE: DNA
<213> ORGANISM: Artificial sequence
<220> FEATURE:
<223> OTHER INFORMATION: Synthetic oligonucleotide
```

<400> SEQUENCE: 28

| caggtccagc tggtgcagtc tggggctgag gtgaagaagc ctggggcctc agtgaaggtt | 60 |
| tcctgcaagg cttctggata caccttcact acctttgcta tgcattgggt gcgccaggcc | 120 |
| cccggacaag gcttgagtg catgggatgg atcaacactg ccaatggtta cacaaaatat | 180 |
| tcacagaagt tccagggcag ggtcaccatt accagcgaca catccgcgag cacagcctcc | 240 |
| atggagctga gcagcctgac atctaaagac acggctgttt attactgtgc gagagttcaa | 300 |
| gatttcggtc actacgaagg gggatacggc tactggggcc agggaaccct ggtcaccgtc | 360 |
| tcctca | 366 |

<210> SEQ ID NO 29
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 29

| cagtctgtgc tgacgcagcc gccctcagtg tctggggccc cagggcagag ggtcatcatc | 60 |
| tcctgcactg ggagcagctc caacatcggg gcaggttatg atgtacactg gtaccagcaa | 120 |
| cttccaggaa cagcccccaa actcctcatc tatggtaaca gctatcggcc ctcaggggtc | 180 |
| cctgaccgat tctctggctc caggtctggc acctcagcct ccctggccat cactgggctc | 240 |
| caggctgagg atgaggctga ttattactgc cagtcccacg acagcagcct gaatgatttt | 300 |
| aatgtgttcg gcagtggcac caaggtgacc gtcctc | 336 |

<210> SEQ ID NO 30
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 30

| gaggtgcagc tggtggagtc tgggggaggc ttggtaccgc cggggggtc cctgagagtc | 60 |
| tcctgtgcag cctctggatt cactttaaga agttatgtca tggcctgggt ccgccaggct | 120 |
| ccagggaagg gctggagtg gtctcaggt attagtggtg atggtgatca cacatactac | 180 |
| gcagactccg tgaagggccg gttcaccatc tccagagaca attccaagaa cacactgtat | 240 |
| ctgcaaatgc acagcctgag agccgaggac acggccctgt attactgtgt gaaagattgg | 300 |
| gggatacgtg ggatctacta ccctccggt atggacgtct ggggccaagg gaccacggtc | 360 |
| atcgtctcct ca | 372 |

<210> SEQ ID NO 31
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 31

| tcccttgagc tggcacagcc accctcggtg tcagtgtccc caggacagac ggccaggatc | 60 |
| acctgctctg gagatggatt gccacaggca tatgcttatt ggtaccaaaa gaagccaggc | 120 |
| caggcccctg tgccgttaat atataaagac actgagaggc cctcagggat ccctgagcga | 180 |
| ttctctggct ccagctcagg gacaacagtc acgttgacca tcagtggagt ccaggcagaa | 240 |

```
gacgaggctg actattactg tcaatctgca gacagcattg gtactaatgt tatattcggc    300
ggagggacca agctgaccgt ccta                                          324
```

<210> SEQ ID NO 32
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 32

```
caggtgcagc tgcaggagtc gggcccagga ctggtgaagc cttcacagac cctgtccctc    60
acctgcgctg tctccggtgg ctccatcagc agtggtggtt actcctggag ctggatccgg   120
cagccaccag ggaagggact ggagtggatt gggtatatct attacagtgg gagcacctac   180
tacaacccgt ccctcaagag tcgacttacc atatctatgg acacgtcgaa gaaccacttc   240
tccctgaagc tgagctctgt gaccgccgcg gacacggccg tgtattactg tgccaccgac   300
tattgtagta gtaccagctg caatacaggg gcccctgtca actggggcca gggaaccctg   360
gtcaccgtct cctca                                                    375
```

<210> SEQ ID NO 33
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 33

```
gacatccagt tgacccagtc tccatccttc ctgtctgcat ctgtaggaga cagagtcacc    60
atcacttgcc gggccagtca gggcattagc agttatttag cctggtatca gcaaaaacca   120
gggaaagccc ctaagctcct gatcaatgct gcatccactt tgcaaagtgg ggtcccgtca   180
agattcagcg gcagtggatc tgggacagaa ttcactctca caatcagcag cctgcagcct   240
gaagattttg caacttatta ctgtcaacag tttaatgctt acccgtacac ttttggccag   300
gggaccaagc tggagatcaa a                                             321
```

<210> SEQ ID NO 34
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 34

```
gaagtgcagc tggtggagtc tgggggaggc ttggtacagc ctggcaggtc cctgagactc    60
tcctgtgcag cctctggatt tacctttgat gattatgcca tgcactgggt ccggcaagct   120
ccagggaagg gcctggagtg ggtctcaggt attagttgga atagtggttt cataggctat   180
gcggactctg tgaagggccg attcaccatc tccagagaca acgccaagaa ctccctgtat   240
ctgcaaatga acagtctgag agctgaggac acggccttgt attactgtgc aaaggatttg   300
ggacgggcgt atagcagtgg ctggtacctc tttgactact ggggccaggg aaccctggtc   360
accgtctcct ca                                                       372
```

<210> SEQ ID NO 35
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 35

```
tcctatgtgc tgactcagcc accctcagtg tcagtggccc caggaaagac ggccaggatt      60
acctgtgggg gaaacaacat tggaagtaaa agtgtgcact ggtatcagca gctgccaggc     120
caggcccctg tgctggtcgt ctatgatgat agcgaccggc cctcagggat ccctgagcga     180
ttctctggct ccaactctgg gtacacggcc accctgatta tcagcagggt cgaagccggg     240
gatgaggccg actattactg tcaggtgtgg gatagtacta gtgatcatgc ttgtgtcttc     300
ggacctggaa ccaaggtcac cgtccta                                         327
```

<210> SEQ ID NO 36
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 36

```
cagctgcagc tgcaggagtc gggcccagga ctggtgaagc cttcggagac cctgtccctc      60
acctgcactg tctctggtgg ctccatcagc agtactagtc actactgggg ctggatccgc     120
cagcccccag ggaaggggct ggagtggatt ggcaatattt attatagtgg gagcacctac     180
tacaaatcgt ccctcaagag tcgagtcgcc atatcagtag acacgtccaa gaaccagttc     240
tccctgaagc tgagctctgt gaccgccgcg gacacggccg tgtatttctg tgcgagagta     300
gttgtagggg ggtactatga taatagaggt tattatagag gtccccccac ccctctgtac     360
tactttgact actggggcca gggaaccctg gtcaccgtct cctca                     405
```

<210> SEQ ID NO 37
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 37

```
gacatccaga tgacccagtc tccatcttcc gtgtctgcat ctgtaggaga cagagtcacc      60
atctcttgtc gggcgagtca gggtattagc acctggttag cctggtatca gcagaaacca     120
gggaaagccc ctaagctcct gatctatgct gtatccagtt tgcaaagtgg ggtcccatca     180
aggttcagcg gcagtggatc tgggacagat ttcactctca ccatcagcag cctgcagcct     240
gaggattttg caacttacta ttgtcaacag gctaacagtc tctcgtggac gttcggccaa     300
gggaccaagg tggaaatcaa a                                               321
```

<210> SEQ ID NO 38
<211> LENGTH: 116
<212> TYPE: PRT
<213> ORGANISM: Artificial sequence
<220> FEATURE:
<223> OTHER INFORMATION: Synthetic peptide

<400> SEQUENCE: 38

```
Gln Val Gln Leu Val Glu Ser Gly Gly Gly Val Val Gln Pro Gly Arg
1               5                   10                  15
Ser Leu Arg Leu Ser Cys Ala Ala Ser Glu Ser Thr Phe Ser Gly Tyr
            20                  25                  30
```

```
Ala Met His Trp Val Arg Gln Ala Pro Gly Lys Gly Leu Glu Trp Val
            35                  40                  45

Ala Val Thr Ser Tyr Asp Gly Ser Ser Asn Tyr Tyr Ala Asp Ser Val
 50                  55                  60

Arg Gly Arg Phe Thr Ile Leu Arg Asp Ile Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Val Arg Glu Tyr Tyr Gly Leu Asp Val Trp Gly Arg Gly Thr Leu Val
                100                 105                 110

Thr Val Ser Ser
        115
```

<210> SEQ ID NO 39
<211> LENGTH: 107
<212> TYPE: PRT
<213> ORGANISM: Artificial sequence
<220> FEATURE:
<223> OTHER INFORMATION: Synthetic peptide

<400> SEQUENCE: 39

```
Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ser Arg Tyr
                 20                  25                  30

Leu Ala Trp Tyr Gln Gln Lys Pro Gly Lys Ala Pro Lys Leu Leu Met
            35                  40                  45

Ser Val Pro Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln His Leu Asn Gly Tyr Pro Tyr
                 85                  90                  95

Ser Phe Gly Gly Gly Thr Lys Val Glu Ile Lys
            100                 105
```

<210> SEQ ID NO 40
<211> LENGTH: 123
<212> TYPE: PRT
<213> ORGANISM: Artificial sequence
<220> FEATURE:
<223> OTHER INFORMATION: Synthetic peptide

<400> SEQUENCE: 40

```
Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Asp Leu
                 20                  25                  30

Ser Met His Trp Val Arg Gln Ala Pro Gly Lys Gly Leu Glu Trp Met
            35                  40                  45

Gly Gly Phe Asp Pro Glu Asp Ser Glu Thr Ile Tyr Ala Gln Lys Phe
 50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Asp Asp Thr Ala Val Tyr Tyr Cys
                 85                  90                  95
```

Ala Thr Glu Asn Phe Asp Thr Leu Ile Gly His Tyr Lys Phe Asp Phe
            100                 105                 110

Trp Gly Gln Gly Thr Leu Val Thr Val Ser Ser
        115                 120

<210> SEQ ID NO 41
<211> LENGTH: 107
<212> TYPE: PRT
<213> ORGANISM: Artificial sequence
<220> FEATURE:
<223> OTHER INFORMATION: Synthetic peptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Asn Leu Leu Ile
        35                  40                  45

His Asp Ala Ser Asn Leu Glu Thr Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Ile Ala Thr Tyr Tyr Cys Gln Gln Tyr Asp Asn Leu Pro Arg
                85                  90                  95

Thr Phe Gly Pro Gly Thr Lys Val Asp Ile Lys
            100                 105

<210> SEQ ID NO 42
<211> LENGTH: 135
<212> TYPE: PRT
<213> ORGANISM: Artificial sequence
<220> FEATURE:
<223> OTHER INFORMATION: Synthetic peptide

<400> SEQUENCE: 42

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Gly Pro Gly Lys Gly Leu Glu Trp Val
        35                  40                  45

Ser Gly Ile Ser Trp Lys Ser Gly Ser Ile Gly Tyr Ala Asp Ser Val
    50                  55                  60

Lys Gly Arg Phe Thr Ile Thr Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Thr Lys Asp Ala Ile Pro Ser Tyr Cys Asp Ser Ile Ser Cys Tyr Arg
            100                 105                 110

Ala Asn Gly Asn Tyr Asp Phe Phe Gly Met Asp Ala Trp Gly Gln Gly
        115                 120                 125

Thr Leu Val Thr Val Ser Ser
    130                 135

<210> SEQ ID NO 43
<211> LENGTH: 107
<212> TYPE: PRT
<213> ORGANISM: Artificial sequence
<220> FEATURE:
<223> OTHER INFORMATION: Synthetic peptide

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Asn Leu Leu Ile
        35                  40                  45

His Asp Ala Ser Asn Leu Glu Thr Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Ile Ala Thr Tyr Tyr Cys Gln Gln Tyr Asp Asn Leu Pro Arg
                85                  90                  95

Thr Phe Gly Pro Gly Thr Lys Val Asp Ile Lys
            100                 105

<210> SEQ ID NO 44
<211> LENGTH: 105
<212> TYPE: PRT
<213> ORGANISM: Artificial sequence
<220> FEATURE:
<223> OTHER INFORMATION: Synthetic peptide

<400> SEQUENCE: 44

Ser Tyr Glu Leu Thr Gln Pro Pro Ser Val Ser Val Ser Ala Gly Gln
1               5                   10                  15

Thr Ala Thr Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Val Val Phe
                85                  90                  95

Gly Gly Gly Thr Lys Leu Thr Val Leu
            100                 105

<210> SEQ ID NO 45
<211> LENGTH: 118
<212> TYPE: PRT
<213> ORGANISM: Artificial sequence
<220> FEATURE:
<223> OTHER INFORMATION: Synthetic peptide

<400> SEQUENCE: 45

Glu Val Gln Leu Val Glu Ser Gly Gly Gly Leu Val Gln Pro Gly Lys
1               5                   10                  15

Ser Leu Arg Leu Ser Cys Ala Ala Ser Gly Val Thr Phe Ser Gly Phe
            20                  25                  30

Arg Met Ser Trp Val Arg Gln Ala Pro Gly Lys Gly Leu Glu Trp Val
        35                  40                  45

Ala Asp Ile Asn Gln Asp Gly Ser Glu Thr Tyr Tyr Val Asp Ser Val
    50                  55                  60

-continued

```
Lys Gly Arg Phe Thr Ile Ser Arg Asp Asn Ala Lys Asn Ser Val Phe
 65                  70                  75                  80

Leu Leu Leu Asn Ser Leu Arg Ala Val Asp Thr Ala Val Tyr Tyr Cys
                 85                  90                  95

Ala Arg Val Val Gly Leu Val Ala Phe Asp Val Trp Gly Gln Gly Thr
            100                 105                 110

Leu Val Thr Val Ser Ser
        115

<210> SEQ ID NO 46

<400> SEQUENCE: 46

000

<210> SEQ ID NO 47
<211> LENGTH: 124
<212> TYPE: PRT
<213> ORGANISM: Artificial sequence
<220> FEATURE:
<223> OTHER INFORMATION: Synthetic peptide

<400> SEQUENCE: 47

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Met Phe Asp Asp Cys
                20                  25                  30

Ala Met His Trp Val Arg Gln Ala Pro Gly Lys Gly Leu Glu Trp Val
            35                  40                  45

Ser Gly Ile Asn Trp Asp Ser Ala Arg Ile Asp Tyr Ala Ala Ser Leu
    50                  55                  60

Lys Gly Arg Phe Thr Ile Ser Arg Asp Asn Ala Arg Asn Ser Leu Tyr
 65                  70                  75                  80

Leu Gln Met Asn Ser Leu Arg Pro Glu Asp Thr Ala Leu Tyr Tyr Cys
                 85                  90                  95

Val Lys Ala Ser Asp Arg Gly Tyr Thr Gly Tyr Asp Thr Ser Phe Asp
            100                 105                 110

Tyr Trp Gly Gln Gly Thr Leu Val Thr Val Ser Ser
            115                 120

<210> SEQ ID NO 48
<211> LENGTH: 110
<212> TYPE: PRT
<213> ORGANISM: Artificial sequence
<220> FEATURE:
<223> OTHER INFORMATION: Synthetic peptide

<400> SEQUENCE: 48

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Arg Asn
                20                  25                  30

Thr Val Asn Trp Tyr Gln Gln Leu Pro Gly Thr Pro Lys Leu Leu
            35                  40                  45

Thr Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
 65                  70                  75                  80
```

```
Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu
            100                 105                 110

<210> SEQ ID NO 49
<211> LENGTH: 121
<212> TYPE: PRT
<213> ORGANISM: Artificial sequence
<220> FEATURE:
<223> OTHER INFORMATION: Synthetic peptide

<400> SEQUENCE: 49

Glu Val Gln Leu Val Glu Ser Gly Gly Asp Leu Val Gln Pro Gly Gly
1               5                   10                  15

Ser Leu Arg Leu Ser Cys Val Ala Ser Gly Phe Ser Phe Ser Asn Phe
            20                  25                  30

Ala Met Ser Trp Val Arg Gln Ala Pro Gly Lys Gly Leu Glu Trp Val
        35                  40                  45

Ala Gly Ile Ser Gly Ser Gly Ser Ser Thr Tyr His Ala Ala Ala Val
    50                  55                  60

Gln Gly Arg Phe Thr Ile Ser Arg Asp Asn Ser Lys Asn Thr Leu Tyr
65                  70                  75                  80

Leu Gln Met Asp Ser Leu Arg Val Asp Asp Met Ala Ile Tyr Tyr Cys
                85                  90                  95

Thr Lys Asp Ala Glu Asn Gln Leu Leu Tyr Trp Phe Asp Pro Trp Gly
            100                 105                 110

Gln Gly Thr Leu Val Thr Val Ser Ser
            115                 120

<210> SEQ ID NO 50
<211> LENGTH: 106
<212> TYPE: PRT
<213> ORGANISM: Artificial sequence
<220> FEATURE:
<223> OTHER INFORMATION: Synthetic peptide

<400> SEQUENCE: 50

Asp Ile Gln Met Thr Gln Ser Pro Ser Ser Leu Ser Ser Val Gly
1               5                   10                  15

Asp Arg Ile Thr Ile Thr Cys Arg Ala Ser Arg Ser Ile Ser Met Tyr
            20                  25                  30

Val Asn Trp Tyr Val Gln Arg Pro Gly His Ala Pro Lys Leu Leu Ile
        35                  40                  45

Tyr Ala Ala Ser Thr Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Thr Tyr Thr Asn Pro Thr
                85                  90                  95

Phe Gly Gln Gly Thr Lys Val Glu Ile Lys
            100                 105

<210> SEQ ID NO 51
<211> LENGTH: 123
<212> TYPE: PRT
<213> ORGANISM: Artificial sequence
<220> FEATURE:
<223> OTHER INFORMATION: Synthetic peptide
```

```
<400> SEQUENCE: 51

Gln Val Gln Leu Gln Glu Ser Gly Pro Gly Leu Val Lys Pro Ser Gly
1               5                   10                  15

Thr Leu Ser Leu Ser Cys Ala Val Ser Gly Gly Ser Ile Ser Ser Tyr
            20                  25                  30

Asp Trp Trp Ser Trp Val Arg Gln Phe Pro Gly Lys Gly Leu Glu Trp
        35                  40                  45

Ile Gly Glu Ile Tyr His Ser Gly Ser Thr Asn Tyr Asn Pro Ser Leu
50                  55                  60

Lys Ser Arg Val Thr Ile Ser Val Asp Lys Ser Asn Asn Gln Phe Ser
65                  70                  75                  80

Leu Asn Leu Thr Ser Val Thr Ala Ala Asp Thr Ala Val Tyr Tyr Cys
                85                  90                  95

Ala Arg Gly Asn Leu Gln Arg Pro Gly Val Tyr Phe Gly Leu Asp Val
            100                 105                 110

Trp Gly Pro Gly Thr Leu Val Thr Val Ser Ser
            115                 120

<210> SEQ ID NO 52
<211> LENGTH: 110
<212> TYPE: PRT
<213> ORGANISM: Artificial sequence
<220> FEATURE:
<223> OTHER INFORMATION: Synthetic peptide

<400> SEQUENCE: 52

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Lys Tyr Val Ser Trp Tyr Gln Gln Tyr Pro Gly Lys Ala Pro Thr Leu
        35                  40                  45

Ile Ile Tyr Glu Val Thr Glu Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Ala Asn
                85                  90                  95

Asn Asn Leu Leu Phe Gly Gly Gly Thr Lys Leu Thr Val Leu
            100                 105                 110

<210> SEQ ID NO 53
<211> LENGTH: 123
<212> TYPE: PRT
<213> ORGANISM: Artificial sequence
<220> FEATURE:
<223> OTHER INFORMATION: Synthetic peptide

<400> SEQUENCE: 53

Gln Val Gln Leu Gln Glu Ser Gly Pro Gly Leu Val Lys Pro Ser Gly
1               5                   10                  15

Thr Leu Ser Leu Ser Cys Ala Val Ser Gly Gly Ser Ile Ser Ser Tyr
            20                  25                  30

Asp Trp Trp Ser Trp Val Arg Gln Phe Pro Gly Lys Gly Leu Glu Trp
        35                  40                  45

Ile Gly Glu Ile Tyr His Ser Gly Ser Thr Asn Tyr Asn Pro Ser Leu
50                  55                  60
```

```
Lys Ser Arg Val Thr Ile Ser Val Asp Lys Ser Asn Asn Gln Phe Ser
 65                  70                  75                  80

Leu Asn Leu Thr Ser Val Thr Ala Ala Asp Thr Ala Val Tyr Tyr Cys
                 85                  90                  95

Ala Arg Gly Asn Leu Gln Arg Pro Gly Val Tyr Phe Gly Leu Asp Val
            100                 105                 110

Trp Gly Pro Gly Thr Leu Val Thr Val Ser Ser
            115                 120
```

<210> SEQ ID NO 54
<211> LENGTH: 110
<212> TYPE: PRT
<213> ORGANISM: Artificial sequence
<220> FEATURE:
<223> OTHER INFORMATION: Synthetic peptide

<400> SEQUENCE: 54

```
Gln Ser Val Leu Thr Gln Pro Pro Ser Ala Ser Gly Thr Pro Gly Gln
 1               5                  10                  15

Arg Val Ser Ile Ala Cys Ser Gly Gly Ser Phe Asn Ile Glu Asn Asn
             20                  25                  30

Tyr Leu Ser Trp Tyr Gln Gln Val Pro Gly Thr Ala Pro Lys Leu Leu
             35                  40                  45

Ile Tyr His Asn Asp Gln Arg Pro Ser Glu Val Pro Asp Arg Phe Ser
 50                  55                  60

Ala Ser Arg Ser Gly Pro Ser Ala Ser Leu Ala Ile Ser Gly Leu Arg
 65                  70                  75                  80

Ser Glu Asp Glu Ala His Tyr Tyr Cys Ala Thr Trp Asp Asp Ser Leu
                 85                  90                  95

Ser Gly Trp Val Phe Gly Gly Gly Thr Lys Leu Thr Val Leu
            100                 105                 110
```

<210> SEQ ID NO 55
<211> LENGTH: 122
<212> TYPE: PRT
<213> ORGANISM: Artificial sequence
<220> FEATURE:
<223> OTHER INFORMATION: Synthetic peptide

<400> SEQUENCE: 55

```
Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
             20                  25                  30

Ser Trp Trp Ser Trp Val Arg Gln Pro Pro Gly Lys Gly Leu Glu Trp
             35                  40                  45

Ile Gly Glu Ile Tyr Trp Ser Gly Arg Thr Asn Tyr Asn Pro Ser Leu
 50                  55                  60

Arg Ser Arg Val Thr Ile Ser Val Asp Lys Ser Lys Asn Gln Phe Ser
 65                  70                  75                  80

Leu Thr Leu Ile Ser Val Thr Ala Ala Asp Thr Ala Val Tyr Tyr Cys
                 85                  90                  95

Ala Lys Thr Pro Asp Thr Ala Met Gly Glu Asp Val Phe Asp Ile Trp
            100                 105                 110

Gly Gln Gly Thr Leu Val Thr Val Ser Ser
            115                 120
```

<210> SEQ ID NO 56
<211> LENGTH: 110
<212> TYPE: PRT
<213> ORGANISM: Artificial sequence
<220> FEATURE:
<223> OTHER INFORMATION: Synthetic peptide

<400> SEQUENCE: 56

```
Gln Ser Val Leu Thr Gln Pro Pro Ser Ala Ser Gly Thr Pro Gly Gln
1               5                   10                  15

Thr Val Thr Ile Ser Cys Ser Gly Ser Asn Ser Asn Leu Gly Ser Asn
            20                  25                  30

Tyr Val Val Trp Tyr Gln Gln Val Pro Gly Thr Ala Pro Lys Leu Leu
        35                  40                  45

Ile Tyr Arg Asn Asn Gln Arg Pro Ser Gly Val Ser Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr His Cys Ala Thr Trp Asp Asp Ser Leu
                85                  90                  95

Ser Gly Arg Val Phe Gly Gly Gly Thr Lys Leu Thr Val Leu
            100                 105                 110
```

<210> SEQ ID NO 57
<211> LENGTH: 122
<212> TYPE: PRT
<213> ORGANISM: Artificial sequence
<220> FEATURE:
<223> OTHER INFORMATION: Synthetic peptide

<400> SEQUENCE: 57

```
Gln Val Gln Leu Val Glu Ser Gly Gly Gly Val Val Gln Pro Gly Lys
1               5                   10                  15

Ser Leu Arg Leu Ser Cys Ala Ala Ser Gly Phe Thr Phe Arg Asn Tyr
            20                  25                  30

Gly Met His Trp Val Arg Gln Ala Pro Gly Lys Gly Leu Asp Trp Val
        35                  40                  45

Ala Leu Ile Ser Tyr Asp Gly Thr His Lys Tyr Tyr Lys Asp Ser Leu
    50                  55                  60

Lys Gly Arg Phe Thr Ile Ser Arg Asp Asn Phe Gln Asn Thr Val Asp
65                  70                  75                  80

Leu Gln Ile Asn Ser Leu Arg Pro Asp Asp Thr Ala Val Tyr Tyr Cys
                85                  90                  95

Ala Lys Glu Leu Ala Thr Ser Gly Val Val Glu Pro Leu Asp Ser Trp
            100                 105                 110

Gly Gln Gly Thr Leu Val Thr Val Ser Ser
        115                 120
```

<210> SEQ ID NO 58
<211> LENGTH: 108
<212> TYPE: PRT
<213> ORGANISM: Artificial sequence
<220> FEATURE:
<223> OTHER INFORMATION: Synthetic peptide

<400> SEQUENCE: 58

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Val Ser Ser
            20                  25                  30
```

```
Tyr Phe Gly Trp Tyr Gln Gln Lys Arg Gly Gln Ser Pro Arg Leu Leu
            35                  40                  45

Ile Tyr Ala Ala Ser Thr Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Asn Thr Pro
                 85                  90                  95

Phe Thr Phe Gly Gly Gly Thr Lys Val Glu Ile Lys
            100                 105
```

```
<210> SEQ ID NO 59
<211> LENGTH: 124
<212> TYPE: PRT
<213> ORGANISM: Artificial sequence
<220> FEATURE:
<223> OTHER INFORMATION: Synthetic peptide

<400> SEQUENCE: 59

Gln Val Gln Leu Val Gln Ser Gly Ala Glu Val Lys Lys Pro Gly Ala
 1               5                  10                  15

Ser Val Lys Val Ser Cys Lys Pro Ser Gly Tyr Asn Phe Ile Asp Tyr
             20                  25                  30

Ala Met His Trp Val Arg Gln Ala Pro Gly Gln Arg Leu Glu Trp Met
         35                  40                  45

Gly Trp Ile Asn Ala Ala Asn Asp Asn Arg Glu Tyr Ser Gln Lys Phe
 50                  55                  60

Gln Gly Arg Val Thr Leu Thr Arg Asp Thr Ser Ala Thr Thr Ala Tyr
 65                  70                  75                  80

Met Glu Leu Ser Ser Leu Thr Phe Glu Asp Thr Ala Val Tyr Tyr Cys
                 85                  90                  95

Ala Arg Asp Arg Gly Thr Met Val Arg Gly Val Gly Gly Trp Phe Asp
            100                 105                 110

Pro Trp Gly Gln Gly Thr Leu Val Thr Val Ser Ser
            115                 120
```

```
<210> SEQ ID NO 60
<211> LENGTH: 108
<212> TYPE: PRT
<213> ORGANISM: Artificial sequence
<220> FEATURE:
<223> OTHER INFORMATION: Synthetic peptide

<400> SEQUENCE: 60

Ser Tyr Val Leu Thr Gln Pro Pro Ser Val Ser Val Ala Pro Gly Glu
 1               5                  10                  15

Thr Ala Arg Ile Thr Cys Gly Gly Asn Asn Ile Gly Ser Lys Ser Val
             20                  25                  30

His Trp Tyr Gln Gln Lys Pro Val Gln Ala Pro Val Val Val Val Tyr
         35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asn His
                 85                  90                  95

Pro Val Phe Gly Gly Gly Thr Lys Val Ala Val Leu
            100                 105
```

<210> SEQ ID NO 61
<211> LENGTH: 125
<212> TYPE: PRT
<213> ORGANISM: Artificial sequence
<220> FEATURE:
<223> OTHER INFORMATION: Synthetic peptide

<400> SEQUENCE: 61

```
Glu Val Gln Leu Val Glu Ser Gly Gly Val Val Gln Pro Gly Gly
1               5                   10                  15

Ser Leu Arg Leu Ser Cys Ala Ala Ser Gly Phe Asn Phe Asp Asp Tyr
            20                  25                  30

Thr Met His Trp Val Arg Gln Ala Pro Gly Lys Gly Leu Glu Trp Val
        35                  40                  45

Ser Leu Ile Thr Trp Asp Gly Leu Ser Thr Tyr Tyr Ala Asp Ser Met
    50                  55                  60

Lys Gly Arg Phe Thr Ile Ser Arg Asp Asn Ser Lys Asp Ser Leu Tyr
65                  70                  75                  80

Leu Gln Met Asp Ser Leu Arg Thr Glu Asp Thr Ala Phe Tyr Tyr Cys
                85                  90                  95

Val Arg Asp Met Gly Pro Gly Ala Val His Phe Tyr Phe Tyr Gly Met
            100                 105                 110

Asp Val Trp Gly Gln Gly Thr Leu Val Thr Val Ser Ser
        115                 120                 125
```

<210> SEQ ID NO 62
<211> LENGTH: 109
<212> TYPE: PRT
<213> ORGANISM: Artificial sequence
<220> FEATURE:
<223> OTHER INFORMATION: Synthetic peptide

<400> SEQUENCE: 62

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asn Tyr
            20                  25                  30

Asn Leu Val Ser Trp Tyr Gln Gln His Pro Gly Lys Val Pro Lys Leu
        35                  40                  45

Ile Ile Tyr Glu Val Ser Lys Arg Pro Ser Gly Ile Ser Lys Arg Phe
    50                  55                  60

Ser Ala Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Gly Val Phe Gly Ala Gly Thr Lys Leu Thr Val Leu
            100                 105
```

<210> SEQ ID NO 63
<211> LENGTH: 121
<212> TYPE: PRT
<213> ORGANISM: Artificial sequence
<220> FEATURE:
<223> OTHER INFORMATION: Synthetic peptide

<400> SEQUENCE: 63

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Ala Met Ser Trp Val Arg Gln Ala Pro Gly Lys Gly Leu Glu Trp Val
        35                  40                  45

Ser Gly Ile Ser Gly Ser Gly Arg Thr Thr Tyr Tyr Thr Asp Ser Val
 50                  55                  60

Lys Gly Arg Phe Asn Ile Ser Arg Asp Asn Thr Lys Asn Thr Leu Phe
 65                  70                  75                  80

Leu Gln Met Asn Ser Leu Arg Ala Glu Asp Thr Ala Val Tyr Tyr Cys
                 85                  90                  95

Val Lys Asp Arg Ala Gly Trp Phe Gly Asn Tyr Phe Asp Tyr Trp Gly
            100                 105                 110

Gln Gly Thr Leu Val Thr Val Ser Ser
            115                 120

<210> SEQ ID NO 64
<211> LENGTH: 107
<212> TYPE: PRT
<213> ORGANISM: Artificial sequence
<220> FEATURE:
<223> OTHER INFORMATION: Synthetic peptide

<400> SEQUENCE: 64

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
                 20                  25                  30

Leu Ala Trp Phe Gln Gln Lys Pro Gly Lys Ala Pro Lys Ser Leu Ile
            35                  40                  45

Tyr Ala Ala Ser Ser Leu Gln Ser Gly Val Pro Ser Lys Phe Ser Gly
 50                  55                  60

Ser Arg Ser Gly Thr Asn Phe Thr Leu Thr Ile Ser Ser Leu Gln Pro
 65                  70                  75                  80

Glu Asp Phe Ala Thr Tyr Tyr Cys Gln Gln Tyr Asn Thr Tyr Pro Pro
                 85                  90                  95

Thr Phe Gly Gln Gly Thr Thr Val Glu Ile Lys
            100                 105

<210> SEQ ID NO 65
<211> LENGTH: 122
<212> TYPE: PRT
<213> ORGANISM: Artificial sequence
<220> FEATURE:
<223> OTHER INFORMATION: Synthetic peptide

<400> SEQUENCE: 65

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Phe
                 20                  25                  30

Ala Met His Trp Val Arg Gln Ala Pro Gly Gln Gly Leu Glu Cys Met
            35                  40                  45

Gly Trp Ile Asn Thr Ala Asn Gly Tyr Thr Lys Tyr Ser Gln Lys Phe
 50                  55                  60

Gln Gly Arg Val Thr Ile Thr Ser Asp Thr Ser Ala Ser Thr Ala Ser
 65                  70                  75                  80

Met Glu Leu Ser Ser Leu Thr Ser Lys Asp Thr Ala Val Tyr Tyr Cys
                 85                  90                  95
```

Ala Arg Val Gln Asp Phe Gly His Tyr Gly Glu Gly Tyr Gly Tyr Trp
            100                 105                 110

Gly Gln Gly Thr Leu Val Thr Val Ser Ser
        115                 120

<210> SEQ ID NO 66
<211> LENGTH: 112
<212> TYPE: PRT
<213> ORGANISM: Artificial sequence
<220> FEATURE:
<223> OTHER INFORMATION: Synthetic peptide

<400> SEQUENCE: 66

Gln Ser Val Leu Thr Gln Pro Pro Ser Val Ser Gly Ala Pro Gly Gln
1               5                   10                  15

Arg Val Ile Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Tyr Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Glu Asp Glu Ala Asp Tyr Tyr Cys Gln Ser His Asp Ser Ser
                85                  90                  95

Leu Asn Asp Phe Asn Val Phe Gly Ser Gly Thr Lys Val Thr Val Leu
            100                 105                 110

<210> SEQ ID NO 67
<211> LENGTH: 124
<212> TYPE: PRT
<213> ORGANISM: Artificial sequence
<220> FEATURE:
<223> OTHER INFORMATION: Synthetic peptide

<400> SEQUENCE: 67

Glu Val Gln Leu Val Glu Ser Gly Gly Gly Leu Val Pro Pro Gly Gly
1               5                   10                  15

Ser Leu Arg Val Ser Cys Ala Ala Ser Gly Phe Thr Leu Arg Ser Tyr
            20                  25                  30

Val Met Ala Trp Val Arg Gln Ala Pro Gly Lys Gly Leu Glu Trp Val
        35                  40                  45

Ser Gly Ile Ser Gly Asp Gly Asp His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Leu Tyr Tyr Cys
                85                  90                  95

Val Lys Asp Trp Gly Ile Arg Gly Ile Tyr Tyr Pro Ser Gly Met Asp
            100                 105                 110

Val Trp Gly Gln Gly Thr Thr Val Ile Val Ser Ser
        115                 120

<210> SEQ ID NO 68
<211> LENGTH: 108
<212> TYPE: PRT
<213> ORGANISM: Artificial sequence
<220> FEATURE:
<223> OTHER INFORMATION: Synthetic peptide -continued

<400> SEQUENCE: 68

Ser Leu Glu Leu Ala Gln Pro Pro Ser Val Ser Val Ser Pro Gly Gln
1               5                   10                  15

Thr Ala Arg Ile Thr Cys Ser Gly Asp Gly Leu Pro Gln Ala Tyr Ala
            20                  25                  30

Tyr Trp Tyr Gln Lys Pro Gly Gln Ala Pro Val Pro Leu Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ile Gly Thr Asn
                85                  90                  95

Val Ile Phe Gly Gly Gly Thr Lys Leu Thr Val Leu
            100                 105

<210> SEQ ID NO 69
<211> LENGTH: 125
<212> TYPE: PRT
<213> ORGANISM: Artificial sequence
<220> FEATURE:
<223> OTHER INFORMATION: Synthetic peptide

<400> SEQUENCE: 69

Gln Val Gln Leu Gln Glu Ser Gly Pro Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Leu Thr Ile Ser Met Asp Thr Ser Lys Asn His Phe
65                  70                  75                  80

Ser Leu Lys Leu Ser Ser Val Thr Ala Ala Asp Thr Ala Val Tyr Tyr
                85                  90                  95

Cys Ala Thr Asp Tyr Cys Ser Ser Thr Ser Cys Asn Thr Gly Ala Pro
            100                 105                 110

Val Asn Trp Gly Gln Gly Thr Leu Val Thr Val Ser Ser
        115                 120                 125

<210> SEQ ID NO 70
<211> LENGTH: 107
<212> TYPE: PRT
<213> ORGANISM: Artificial sequence
<220> FEATURE:
<223> OTHER INFORMATION: Synthetic peptide

<400> SEQUENCE: 70

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Asn Ala Ala Ser Thr Leu Gln Ser Gly Val Pro Ser Arg Phe Ser Gly
    50                  55                  60

```
Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Phe Asn Ala Tyr Pro Tyr
                 85                  90                  95

Thr Phe Gly Gln Gly Thr Lys Leu Glu Ile Lys
                100                 105

<210> SEQ ID NO 71
<211> LENGTH: 124
<212> TYPE: PRT
<213> ORGANISM: Artificial sequence
<220> FEATURE:
<223> OTHER INFORMATION: Synthetic peptide

<400> SEQUENCE: 71

Glu Val Gln Leu Val Glu Ser Gly Gly Leu Val Gln Pro Gly Arg
 1               5                  10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
             35                  40                  45

Ser Gly Ile Ser Trp Asn Ser Gly Phe Ile Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Leu Gly Arg Ala Tyr Ser Ser Gly Trp Tyr Leu Phe Asp
                100                 105                 110

Tyr Trp Gly Gln Gly Thr Leu Val Thr Val Ser Ser
            115                 120

<210> SEQ ID NO 72
<211> LENGTH: 109
<212> TYPE: PRT
<213> ORGANISM: Artificial sequence
<220> FEATURE:
<223> OTHER INFORMATION: Synthetic peptide

<400> SEQUENCE: 72

Ser Tyr Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
                 20                  25                  30

His Trp Tyr Gln Gln Leu Pro Gly Gln Ala Pro Val Leu Val Val Tyr
             35                  40                  45

Asp Asp Ser Asp Arg Pro Ser Gly Ile Pro Glu Arg Phe Ser Gly Ser
         50                  55                  60

Asn Ser Gly Tyr Thr Ala Thr Leu Ile Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Ala Cys Val Phe Gly Pro Gly Thr Lys Val Thr Val Leu
                100                 105

<210> SEQ ID NO 73
<211> LENGTH: 135
<212> TYPE: PRT
<213> ORGANISM: Artificial sequence
```

```
<220> FEATURE:
<223> OTHER INFORMATION: Synthetic peptide

<400> SEQUENCE: 73

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Lys Ser Ser
    50                  55                  60

Leu Lys Ser Arg Val Ala Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Val Val Val Gly Gly Tyr Tyr Asp Asn Arg Gly Tyr Tyr
            100                 105                 110

Arg Gly Pro Pro Thr Pro Leu Tyr Tyr Phe Asp Tyr Trp Gly Gln Gly
        115                 120                 125

Thr Leu Val Thr Val Ser Ser
    130                 135

<210> SEQ ID NO 74
<211> LENGTH: 107
<212> TYPE: PRT
<213> ORGANISM: Artificial sequence
<220> FEATURE:
<223> OTHER INFORMATION: Synthetic peptide

<400> SEQUENCE: 74

Asp Ile Gln Met Thr Gln Ser Pro Ser Ser Val Ser Ala Ser Val Gly
1               5                   10                  15

Asp Arg Val Thr Ile Ser Cys Arg Ala Ser Pro Gly Ile Ser Thr Trp
            20                  25                  30

Leu Ala Trp Tyr Gln Gln Lys Pro Gly Lys Ala Pro Lys Leu Leu Ile
        35                  40                  45

Tyr Ala Val Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Leu Ser Trp
                85                  90                  95

Thr Phe Gly Gln Gly Thr Lys Val Glu Ile Lys
            100                 105

<210> SEQ ID NO 75
<211> LENGTH: 8
<212> TYPE: PRT
<213> ORGANISM: Artificial sequence
<220> FEATURE:
<223> OTHER INFORMATION: Synthetic peptide

<400> SEQUENCE: 75

Glu Ser Thr Phe Ser Gly Tyr Ala
1               5
```

```
<210> SEQ ID NO 76
<211> LENGTH: 8
<212> TYPE: PRT
<213> ORGANISM: Artificial sequence
<220> FEATURE:
<223> OTHER INFORMATION: Synthetic peptide

<400> SEQUENCE: 76

Thr Ser Tyr Asp Gly Ser Ser Asn
1               5

<210> SEQ ID NO 77
<211> LENGTH: 9
<212> TYPE: PRT
<213> ORGANISM: Artificial sequence
<220> FEATURE:
<223> OTHER INFORMATION: Synthetic peptide

<400> SEQUENCE: 77

Val Arg Glu Tyr Tyr Gly Leu Asp Val
1               5

<210> SEQ ID NO 78
<211> LENGTH: 8
<212> TYPE: PRT
<213> ORGANISM: Artificial sequence
<220> FEATURE:
<223> OTHER INFORMATION: Synthetic peptide

<400> SEQUENCE: 78

Gly Tyr Thr Leu Thr Asp Leu Ser
1               5

<210> SEQ ID NO 79
<211> LENGTH: 8
<212> TYPE: PRT
<213> ORGANISM: Artificial sequence
<220> FEATURE:
<223> OTHER INFORMATION: Synthetic peptide

<400> SEQUENCE: 79

Phe Asp Pro Glu Asp Ser Glu Thr
1               5

<210> SEQ ID NO 80
<211> LENGTH: 16
<212> TYPE: PRT
<213> ORGANISM: Artificial sequence
<220> FEATURE:
<223> OTHER INFORMATION: Synthetic peptide

<400> SEQUENCE: 80

Ala Thr Glu Asn Phe Asp Thr Leu Ile Gly His Tyr Lys Phe Asp Phe
1               5                   10                  15

<210> SEQ ID NO 81
<211> LENGTH: 8
<212> TYPE: PRT
<213> ORGANISM: Artificial sequence
<220> FEATURE:
<223> OTHER INFORMATION: Synthetic peptide

<400> SEQUENCE: 81

Gly Phe Thr Phe Asp Asp Tyr Ala
1               5
```

```
<210> SEQ ID NO 82
<211> LENGTH: 8
<212> TYPE: PRT
<213> ORGANISM: Artificial sequence
<220> FEATURE:
<223> OTHER INFORMATION: Synthetic peptide

<400> SEQUENCE: 82

Ile Ser Trp Lys Ser Gly Ser Ile
1               5

<210> SEQ ID NO 83
<211> LENGTH: 28
<212> TYPE: PRT
<213> ORGANISM: Artificial sequence
<220> FEATURE:
<223> OTHER INFORMATION: Synthetic peptide

<400> SEQUENCE: 83

Thr Lys Asp Ala Ile Pro Ser Tyr Cys Asp Ser Ile Ser Cys Tyr Arg
1               5                   10                  15

Ala Asn Gly Asn Tyr Asp Phe Phe Gly Met Asp Ala
            20                  25

<210> SEQ ID NO 84
<211> LENGTH: 8
<212> TYPE: PRT
<213> ORGANISM: Artificial sequence
<220> FEATURE:
<223> OTHER INFORMATION: Synthetic peptide

<400> SEQUENCE: 84

Gly Val Thr Phe Ser Gly Phe Arg
1               5

<210> SEQ ID NO 85
<211> LENGTH: 8
<212> TYPE: PRT
<213> ORGANISM: Artificial sequence
<220> FEATURE:
<223> OTHER INFORMATION: Synthetic peptide

<400> SEQUENCE: 85

Ile Asn Gln Asp Gly Ser Glu Thr
1               5

<210> SEQ ID NO 86
<211> LENGTH: 11
<212> TYPE: PRT
<213> ORGANISM: Artificial sequence
<220> FEATURE:
<223> OTHER INFORMATION: Synthetic peptide

<400> SEQUENCE: 86

Ala Arg Val Val Gly Leu Val Ala Phe Asp Val
1               5                   10

<210> SEQ ID NO 87
<211> LENGTH: 8
<212> TYPE: PRT
<213> ORGANISM: Artificial sequence
<220> FEATURE:
<223> OTHER INFORMATION: Synthetic peptide

<400> SEQUENCE: 87

Gly Phe Met Phe Asp Asp Cys Ala
1               5
```

```
<210> SEQ ID NO 88
<211> LENGTH: 8
<212> TYPE: PRT
<213> ORGANISM: Artificial sequence
<220> FEATURE:
<223> OTHER INFORMATION: Synthetic peptide

<400> SEQUENCE: 88

Ile Asn Trp Asp Ser Ala Arg Ile
1               5

<210> SEQ ID NO 89
<211> LENGTH: 17
<212> TYPE: PRT
<213> ORGANISM: Artificial sequence
<220> FEATURE:
<223> OTHER INFORMATION: Synthetic peptide

<400> SEQUENCE: 89

Val Lys Ala Ser Asp Arg Gly Tyr Thr Gly Tyr Asp Thr Ser Phe Asp
1               5                   10                  15

Tyr

<210> SEQ ID NO 90
<211> LENGTH: 8
<212> TYPE: PRT
<213> ORGANISM: Artificial sequence
<220> FEATURE:
<223> OTHER INFORMATION: Synthetic peptide

<400> SEQUENCE: 90

Gly Phe Ser Phe Ser Asn Phe Ala
1               5

<210> SEQ ID NO 91
<211> LENGTH: 8
<212> TYPE: PRT
<213> ORGANISM: Artificial sequence
<220> FEATURE:
<223> OTHER INFORMATION: Synthetic peptide

<400> SEQUENCE: 91

Ile Ser Gly Ser Gly Ser Ser Thr
1               5

<210> SEQ ID NO 92
<211> LENGTH: 14
<212> TYPE: PRT
<213> ORGANISM: Artificial sequence
<220> FEATURE:
<223> OTHER INFORMATION: Synthetic peptide

<400> SEQUENCE: 92

Thr Lys Asp Ala Glu Asn Gln Leu Leu Tyr Trp Phe Asp Pro
1               5                   10

<210> SEQ ID NO 93
<211> LENGTH: 9
<212> TYPE: PRT
<213> ORGANISM: Artificial sequence
<220> FEATURE:
<223> OTHER INFORMATION: Synthetic peptide

<400> SEQUENCE: 93

Gly Gly Ser Ile Ser Ser Tyr Asp Trp
1               5
```

```
<210> SEQ ID NO 94
<211> LENGTH: 7
<212> TYPE: PRT
<213> ORGANISM: Artificial sequence
<220> FEATURE:
<223> OTHER INFORMATION: Synthetic peptide

<400> SEQUENCE: 94

Ile Tyr His Ser Gly Ser Thr
1               5

<210> SEQ ID NO 95
<211> LENGTH: 16
<212> TYPE: PRT
<213> ORGANISM: Artificial sequence
<220> FEATURE:
<223> OTHER INFORMATION: Synthetic peptide

<400> SEQUENCE: 95

Ala Arg Gly Asn Leu Gln Arg Pro Gly Val Tyr Phe Gly Leu Asp Val
1               5                   10                  15

<210> SEQ ID NO 96
<211> LENGTH: 9
<212> TYPE: PRT
<213> ORGANISM: Artificial sequence
<220> FEATURE:
<223> OTHER INFORMATION: Synthetic peptide

<400> SEQUENCE: 96

Gly Gly Ser Ile Ser Ser Tyr Asp Trp
1               5

<210> SEQ ID NO 97
<211> LENGTH: 7
<212> TYPE: PRT
<213> ORGANISM: Artificial sequence
<220> FEATURE:
<223> OTHER INFORMATION: Synthetic peptide

<400> SEQUENCE: 97

Ile Tyr His Ser Gly Ser Thr
1               5

<210> SEQ ID NO 98
<211> LENGTH: 16
<212> TYPE: PRT
<213> ORGANISM: Artificial sequence
<220> FEATURE:
<223> OTHER INFORMATION: Synthetic peptide

<400> SEQUENCE: 98

Ala Arg Gly Asn Leu Gln Arg Pro Gly Val Tyr Phe Gly Leu Asp Val
1               5                   10                  15

<210> SEQ ID NO 99
<211> LENGTH: 9
<212> TYPE: PRT
<213> ORGANISM: Artificial sequence
<220> FEATURE:
<223> OTHER INFORMATION: Synthetic peptide

<400> SEQUENCE: 99

Gly Gly Ser Ile Ser Ser Ser Ser Trp
1               5
```

```
<210> SEQ ID NO 100
<211> LENGTH: 7
<212> TYPE: PRT
<213> ORGANISM: Artificial sequence
<220> FEATURE:
<223> OTHER INFORMATION: Synthetic peptide

<400> SEQUENCE: 100

Ile Tyr Trp Ser Gly Arg Thr
1               5

<210> SEQ ID NO 101
<211> LENGTH: 15
<212> TYPE: PRT
<213> ORGANISM: Artificial sequence
<220> FEATURE:
<223> OTHER INFORMATION: Synthetic peptide

<400> SEQUENCE: 101

Ala Lys Thr Pro Asp Thr Ala Met Gly Glu Asp Val Phe Asp Ile
1               5                   10                  15

<210> SEQ ID NO 102
<211> LENGTH: 8
<212> TYPE: PRT
<213> ORGANISM: Artificial sequence
<220> FEATURE:
<223> OTHER INFORMATION: Synthetic peptide

<400> SEQUENCE: 102

Gly Phe Thr Phe Arg Asn Tyr Gly
1               5

<210> SEQ ID NO 103
<211> LENGTH: 8
<212> TYPE: PRT
<213> ORGANISM: Artificial sequence
<220> FEATURE:
<223> OTHER INFORMATION: Synthetic peptide

<400> SEQUENCE: 103

Ile Ser Tyr Asp Gly Thr His Lys
1               5

<210> SEQ ID NO 104
<211> LENGTH: 15
<212> TYPE: PRT
<213> ORGANISM: Artificial sequence
<220> FEATURE:
<223> OTHER INFORMATION: Synthetic peptide

<400> SEQUENCE: 104

Ala Lys Glu Leu Ala Thr Ser Gly Val Val Glu Pro Leu Asp Ser
1               5                   10                  15

<210> SEQ ID NO 105
<211> LENGTH: 8
<212> TYPE: PRT
<213> ORGANISM: Artificial sequence
<220> FEATURE:
<223> OTHER INFORMATION: Synthetic peptide

<400> SEQUENCE: 105

Gly Tyr Asn Phe Ile Asp Tyr Ala
1               5
```

```
<210> SEQ ID NO 106
<211> LENGTH: 8
<212> TYPE: PRT
<213> ORGANISM: Artificial sequence
<220> FEATURE:
<223> OTHER INFORMATION: Synthetic peptide

<400> SEQUENCE: 106

Ile Asn Ala Ala Asn Asp Asn Arg
1               5

<210> SEQ ID NO 107
<211> LENGTH: 17
<212> TYPE: PRT
<213> ORGANISM: Artificial sequence
<220> FEATURE:
<223> OTHER INFORMATION: Synthetic peptide

<400> SEQUENCE: 107

Ala Arg Asp Arg Gly Thr Met Val Arg Gly Val Gly Gly Trp Phe Asp
1               5                   10                  15

Pro

<210> SEQ ID NO 108
<211> LENGTH: 8
<212> TYPE: PRT
<213> ORGANISM: Artificial sequence
<220> FEATURE:
<223> OTHER INFORMATION: Synthetic peptide

<400> SEQUENCE: 108

Gly Phe Asn Phe Asp Asp Tyr Thr
1               5

<210> SEQ ID NO 109
<211> LENGTH: 8
<212> TYPE: PRT
<213> ORGANISM: Artificial sequence
<220> FEATURE:
<223> OTHER INFORMATION: Synthetic peptide

<400> SEQUENCE: 109

Ile Thr Trp Asp Gly Leu Ser Thr
1               5

<210> SEQ ID NO 110
<211> LENGTH: 18
<212> TYPE: PRT
<213> ORGANISM: Artificial sequence
<220> FEATURE:
<223> OTHER INFORMATION: Synthetic peptide

<400> SEQUENCE: 110

Val Arg Asp Met Gly Pro Gly Ala Val His Phe Tyr Phe Tyr Gly Met
1               5                   10                  15

Asp Val

<210> SEQ ID NO 111
<211> LENGTH: 8
<212> TYPE: PRT
<213> ORGANISM: Artificial sequence
<220> FEATURE:
<223> OTHER INFORMATION: Synthetic peptide
```

```
<400> SEQUENCE: 111

Gly Phe Thr Phe Ser Asn Tyr Ala
1               5

<210> SEQ ID NO 112
<211> LENGTH: 8
<212> TYPE: PRT
<213> ORGANISM: Artificial sequence
<220> FEATURE:
<223> OTHER INFORMATION: Synthetic peptide

<400> SEQUENCE: 112

Ile Ser Gly Ser Gly Arg Thr Thr
1               5

<210> SEQ ID NO 113
<211> LENGTH: 14
<212> TYPE: PRT
<213> ORGANISM: Artificial sequence
<220> FEATURE:
<223> OTHER INFORMATION: Synthetic peptide

<400> SEQUENCE: 113

Val Lys Asp Arg Ala Gly Trp Phe Gly Asn Tyr Phe Asp Tyr
1               5                   10

<210> SEQ ID NO 114
<211> LENGTH: 8
<212> TYPE: PRT
<213> ORGANISM: Artificial sequence
<220> FEATURE:
<223> OTHER INFORMATION: Synthetic peptide

<400> SEQUENCE: 114

Gly Tyr Thr Phe Thr Thr Phe Ala
1               5

<210> SEQ ID NO 115
<211> LENGTH: 8
<212> TYPE: PRT
<213> ORGANISM: Artificial sequence
<220> FEATURE:
<223> OTHER INFORMATION: Synthetic peptide

<400> SEQUENCE: 115

Ile Asn Thr Ala Asn Gly Tyr Thr
1               5

<210> SEQ ID NO 116
<211> LENGTH: 15
<212> TYPE: PRT
<213> ORGANISM: Artificial sequence
<220> FEATURE:
<223> OTHER INFORMATION: Synthetic peptide

<400> SEQUENCE: 116

Ala Arg Val Gln Asp Phe Gly His Tyr Glu Gly Gly Tyr Gly Tyr
1               5                   10                  15

<210> SEQ ID NO 117
<211> LENGTH: 8
<212> TYPE: PRT
<213> ORGANISM: Artificial sequence
<220> FEATURE:
<223> OTHER INFORMATION: Synthetic peptide
```

```
<400> SEQUENCE: 117

Gly Phe Thr Leu Arg Ser Tyr Val
1               5

<210> SEQ ID NO 118
<211> LENGTH: 8
<212> TYPE: PRT
<213> ORGANISM: Artificial sequence
<220> FEATURE:
<223> OTHER INFORMATION: Synthetic peptide

<400> SEQUENCE: 118

Ile Ser Gly Asp Gly Asp His Thr
1               5

<210> SEQ ID NO 119
<211> LENGTH: 17
<212> TYPE: PRT
<213> ORGANISM: Artificial sequence
<220> FEATURE:
<223> OTHER INFORMATION: Synthetic peptide

<400> SEQUENCE: 119

Val Lys Asp Trp Gly Ile Arg Gly Ile Tyr Tyr Pro Ser Gly Met Asp
1               5                   10                  15

Val

<210> SEQ ID NO 120
<211> LENGTH: 10
<212> TYPE: PRT
<213> ORGANISM: Artificial sequence
<220> FEATURE:
<223> OTHER INFORMATION: Synthetic peptide

<400> SEQUENCE: 120

Gly Gly Ser Ile Ser Ser Gly Gly Tyr Ser
1               5                   10

<210> SEQ ID NO 121
<211> LENGTH: 7
<212> TYPE: PRT
<213> ORGANISM: Artificial sequence
<220> FEATURE:
<223> OTHER INFORMATION: Synthetic peptide

<400> SEQUENCE: 121

Ile Tyr Tyr Ser Gly Ser Thr
1               5

<210> SEQ ID NO 122
<211> LENGTH: 17
<212> TYPE: PRT
<213> ORGANISM: Artificial sequence
<220> FEATURE:
<223> OTHER INFORMATION: Synthetic peptide

<400> SEQUENCE: 122

Ala Thr Asp Tyr Cys Ser Ser Thr Ser Cys Asn Thr Gly Ala Pro Val
1               5                   10                  15

Asn

<210> SEQ ID NO 123
<211> LENGTH: 8
<212> TYPE: PRT
<213> ORGANISM: Artificial sequence
```

```
<220> FEATURE:
<223> OTHER INFORMATION: Synthetic peptide

<400> SEQUENCE: 123

Gly Phe Thr Phe Asp Asp Tyr Ala
1               5

<210> SEQ ID NO 124
<211> LENGTH: 8
<212> TYPE: PRT
<213> ORGANISM: Artificial sequence
<220> FEATURE:
<223> OTHER INFORMATION: Synthetic peptide

<400> SEQUENCE: 124

Ile Ser Trp Asn Ser Gly Phe Ile
1               5

<210> SEQ ID NO 125
<211> LENGTH: 17
<212> TYPE: PRT
<213> ORGANISM: Artificial sequence
<220> FEATURE:
<223> OTHER INFORMATION: Synthetic peptide

<400> SEQUENCE: 125

Ala Lys Asp Leu Gly Arg Ala Tyr Ser Ser Gly Trp Tyr Leu Phe Asp
1               5                   10                  15

Tyr

<210> SEQ ID NO 126
<211> LENGTH: 10
<212> TYPE: PRT
<213> ORGANISM: Artificial sequence
<220> FEATURE:
<223> OTHER INFORMATION: Synthetic peptide

<400> SEQUENCE: 126

Gly Gly Ser Ile Ser Ser Thr Ser His Tyr
1               5                   10

<210> SEQ ID NO 127
<211> LENGTH: 7
<212> TYPE: PRT
<213> ORGANISM: Artificial sequence
<220> FEATURE:
<223> OTHER INFORMATION: Synthetic peptide

<400> SEQUENCE: 127

Ile Tyr Tyr Ser Gly Ser Thr
1               5

<210> SEQ ID NO 128
<211> LENGTH: 27
<212> TYPE: PRT
<213> ORGANISM: Artificial sequence
<220> FEATURE:
<223> OTHER INFORMATION: Synthetic peptide

<400> SEQUENCE: 128

Ala Arg Val Val Val Gly Gly Tyr Tyr Asp Asn Arg Gly Tyr Tyr Arg
1               5                   10                  15

Gly Pro Pro Thr Pro Leu Tyr Tyr Phe Asp Tyr
            20                  25
```

```
<210> SEQ ID NO 129
<211> LENGTH: 6
<212> TYPE: PRT
<213> ORGANISM: Artificial sequence
<220> FEATURE:
<223> OTHER INFORMATION: Synthetic peptide

<400> SEQUENCE: 129

Gln Gly Ile Ser Arg Tyr
1               5

<210> SEQ ID NO 130
<211> LENGTH: 3
<212> TYPE: PRT
<213> ORGANISM: Artificial sequence
<220> FEATURE:
<223> OTHER INFORMATION: Synthetic peptide

<400> SEQUENCE: 130

Val Pro Ser
1

<210> SEQ ID NO 131
<211> LENGTH: 9
<212> TYPE: PRT
<213> ORGANISM: Artificial sequence
<220> FEATURE:
<223> OTHER INFORMATION: Synthetic peptide

<400> SEQUENCE: 131

Gln His Leu Asn Gly Tyr Pro Tyr Ser
1               5

<210> SEQ ID NO 132
<211> LENGTH: 6
<212> TYPE: PRT
<213> ORGANISM: Artificial sequence
<220> FEATURE:
<223> OTHER INFORMATION: Synthetic peptide

<400> SEQUENCE: 132

Gln Asp Ile Ser Asn Tyr
1               5

<210> SEQ ID NO 133
<211> LENGTH: 3
<212> TYPE: PRT
<213> ORGANISM: Artificial sequence
<220> FEATURE:
<223> OTHER INFORMATION: Synthetic peptide

<400> SEQUENCE: 133

Asp Ala Ser
1

<210> SEQ ID NO 134
<211> LENGTH: 9
<212> TYPE: PRT
<213> ORGANISM: Artificial sequence
<220> FEATURE:
<223> OTHER INFORMATION: Synthetic peptide

<400> SEQUENCE: 134

Gln Gln Tyr Asp Asn Leu Pro Arg Thr
1               5
```

```
<210> SEQ ID NO 135
<211> LENGTH: 6
<212> TYPE: PRT
<213> ORGANISM: Artificial sequence
<220> FEATURE:
<223> OTHER INFORMATION: Synthetic peptide

<400> SEQUENCE: 135

Gln Asp Ile Ser Asn Tyr
1               5

<210> SEQ ID NO 136
<211> LENGTH: 3
<212> TYPE: PRT
<213> ORGANISM: Artificial sequence
<220> FEATURE:
<223> OTHER INFORMATION: Synthetic peptide

<400> SEQUENCE: 136

Asp Ala Ser
1

<210> SEQ ID NO 137
<211> LENGTH: 9
<212> TYPE: PRT
<213> ORGANISM: Artificial sequence
<220> FEATURE:
<223> OTHER INFORMATION: Synthetic peptide

<400> SEQUENCE: 137

Gln Gln Tyr Asp Asn Leu Pro Arg Thr
1               5

<210> SEQ ID NO 138
<211> LENGTH: 6
<212> TYPE: PRT
<213> ORGANISM: Artificial sequence
<220> FEATURE:
<223> OTHER INFORMATION: Synthetic peptide

<400> SEQUENCE: 138

Lys Leu Gly Asp Lys Tyr
1               5

<210> SEQ ID NO 139
<211> LENGTH: 3
<212> TYPE: PRT
<213> ORGANISM: Artificial sequence
<220> FEATURE:
<223> OTHER INFORMATION: Synthetic peptide

<400> SEQUENCE: 139

Gln Asp Ser
1

<210> SEQ ID NO 140
<211> LENGTH: 8
<212> TYPE: PRT
<213> ORGANISM: Artificial sequence
<220> FEATURE:
<223> OTHER INFORMATION: Synthetic peptide

<400> SEQUENCE: 140

Gln Ala Trp Asp Ser Ser Val Val
1               5
```

```
<210> SEQ ID NO 141
<211> LENGTH: 6
<212> TYPE: PRT
<213> ORGANISM: Artificial sequence
<220> FEATURE:
<223> OTHER INFORMATION: Synthetic peptide

<400> SEQUENCE: 141

Thr Ile Gly Ser Lys Thr
1               5

<210> SEQ ID NO 142
<211> LENGTH: 3
<212> TYPE: PRT
<213> ORGANISM: Artificial sequence
<220> FEATURE:
<223> OTHER INFORMATION: Synthetic peptide

<400> SEQUENCE: 142

Asp Asp Ser
1

<210> SEQ ID NO 143
<211> LENGTH: 11
<212> TYPE: PRT
<213> ORGANISM: Artificial sequence
<220> FEATURE:
<223> OTHER INFORMATION: Synthetic peptide

<400> SEQUENCE: 143

Gln Val Trp Asp Ser Val Ser Asp His Ala Val
1               5                   10

<210> SEQ ID NO 144
<211> LENGTH: 8
<212> TYPE: PRT
<213> ORGANISM: Artificial sequence
<220> FEATURE:
<223> OTHER INFORMATION: Synthetic peptide

<400> SEQUENCE: 144

Ser Ser Asn Ile Gly Arg Asn Thr
1               5

<210> SEQ ID NO 145
<211> LENGTH: 3
<212> TYPE: PRT
<213> ORGANISM: Artificial sequence
<220> FEATURE:
<223> OTHER INFORMATION: Synthetic peptide

<400> SEQUENCE: 145

Ser Asn Asn
1

<210> SEQ ID NO 146
<211> LENGTH: 11
<212> TYPE: PRT
<213> ORGANISM: Artificial sequence
<220> FEATURE:
<223> OTHER INFORMATION: Synthetic peptide

<400> SEQUENCE: 146

Ala Ala Trp Asp Asp Ser Leu Ser Gly Tyr Val
1               5                   10
```

```
<210> SEQ ID NO 147
<211> LENGTH: 6
<212> TYPE: PRT
<213> ORGANISM: Artificial sequence
<220> FEATURE:
<223> OTHER INFORMATION: Synthetic peptide

<400> SEQUENCE: 147

Arg Ser Ile Ser Met Tyr
1               5

<210> SEQ ID NO 148
<211> LENGTH: 3
<212> TYPE: PRT
<213> ORGANISM: Artificial sequence
<220> FEATURE:
<223> OTHER INFORMATION: Synthetic peptide

<400> SEQUENCE: 148

Ala Ala Ser
1

<210> SEQ ID NO 149
<211> LENGTH: 8
<212> TYPE: PRT
<213> ORGANISM: Artificial sequence
<220> FEATURE:
<223> OTHER INFORMATION: Synthetic peptide

<400> SEQUENCE: 149

Gln Gln Thr Tyr Thr Asn Pro Thr
1               5

<210> SEQ ID NO 150
<211> LENGTH: 9
<212> TYPE: PRT
<213> ORGANISM: Artificial sequence
<220> FEATURE:
<223> OTHER INFORMATION: Synthetic peptide

<400> SEQUENCE: 150

Ser Ser Asp Val Gly Gly Tyr Lys Tyr
1               5

<210> SEQ ID NO 151
<211> LENGTH: 3
<212> TYPE: PRT
<213> ORGANISM: Artificial sequence
<220> FEATURE:
<223> OTHER INFORMATION: Synthetic peptide

<400> SEQUENCE: 151

Glu Val Thr
1

<210> SEQ ID NO 152
<211> LENGTH: 10
<212> TYPE: PRT
<213> ORGANISM: Artificial sequence
<220> FEATURE:
<223> OTHER INFORMATION: Synthetic peptide

<400> SEQUENCE: 152

Ser Ser Tyr Ala Ala Asn Asn Asn Leu Leu
1               5                   10
```

```
<210> SEQ ID NO 153
<211> LENGTH: 8
<212> TYPE: PRT
<213> ORGANISM: Artificial sequence
<220> FEATURE:
<223> OTHER INFORMATION: Synthetic peptide

<400> SEQUENCE: 153

Ser Phe Asn Ile Glu Asn Asn Tyr
1               5

<210> SEQ ID NO 154
<211> LENGTH: 3
<212> TYPE: PRT
<213> ORGANISM: Artificial sequence
<220> FEATURE:
<223> OTHER INFORMATION: Synthetic peptide

<400> SEQUENCE: 154

His Asn Asp
1

<210> SEQ ID NO 155
<211> LENGTH: 11
<212> TYPE: PRT
<213> ORGANISM: Artificial sequence
<220> FEATURE:
<223> OTHER INFORMATION: Synthetic peptide

<400> SEQUENCE: 155

Ala Thr Trp Asp Asp Ser Leu Ser Gly Trp Val
1               5                   10

<210> SEQ ID NO 156
<211> LENGTH: 8
<212> TYPE: PRT
<213> ORGANISM: Artificial sequence
<220> FEATURE:
<223> OTHER INFORMATION: Synthetic peptide

<400> SEQUENCE: 156

Asn Ser Asn Leu Gly Ser Asn Tyr
1               5

<210> SEQ ID NO 157
<211> LENGTH: 3
<212> TYPE: PRT
<213> ORGANISM: Artificial sequence
<220> FEATURE:
<223> OTHER INFORMATION: Synthetic peptide

<400> SEQUENCE: 157

Arg Asn Asn
1

<210> SEQ ID NO 158
<211> LENGTH: 11
<212> TYPE: PRT
<213> ORGANISM: Artificial sequence
<220> FEATURE:
<223> OTHER INFORMATION: Synthetic peptide

<400> SEQUENCE: 158

Ala Thr Trp Asp Asp Ser Leu Ser Gly Arg Val
1               5                   10
```

```
<210> SEQ ID NO 159
<211> LENGTH: 7
<212> TYPE: PRT
<213> ORGANISM: Artificial sequence
<220> FEATURE:
<223> OTHER INFORMATION: Synthetic peptide

<400> SEQUENCE: 159

Gln Ser Leu Val Ser Ser Tyr
1               5

<210> SEQ ID NO 160
<211> LENGTH: 3
<212> TYPE: PRT
<213> ORGANISM: Artificial sequence
<220> FEATURE:
<223> OTHER INFORMATION: Synthetic peptide

<400> SEQUENCE: 160

Ala Ala Ser
1

<210> SEQ ID NO 161
<211> LENGTH: 9
<212> TYPE: PRT
<213> ORGANISM: Artificial sequence
<220> FEATURE:
<223> OTHER INFORMATION: Synthetic peptide

<400> SEQUENCE: 161

Gln Gln Tyr Gly Asn Thr Pro Phe Thr
1               5

<210> SEQ ID NO 162
<211> LENGTH: 6
<212> TYPE: PRT
<213> ORGANISM: Artificial sequence
<220> FEATURE:
<223> OTHER INFORMATION: Synthetic peptide

<400> SEQUENCE: 162

Asn Ile Gly Ser Lys Ser
1               5

<210> SEQ ID NO 163
<211> LENGTH: 3
<212> TYPE: PRT
<213> ORGANISM: Artificial sequence
<220> FEATURE:
<223> OTHER INFORMATION: Synthetic peptide

<400> SEQUENCE: 163

Asp Asp Ser
1

<210> SEQ ID NO 164
<211> LENGTH: 11
<212> TYPE: PRT
<213> ORGANISM: Artificial sequence
<220> FEATURE:
<223> OTHER INFORMATION: Synthetic peptide

<400> SEQUENCE: 164

Gln Val Trp Asp Ser Ser Ser Asn His Pro Val
1               5                   10
```

```
<210> SEQ ID NO 165
<211> LENGTH: 9
<212> TYPE: PRT
<213> ORGANISM: Artificial sequence
<220> FEATURE:
<223> OTHER INFORMATION: Synthetic peptide

<400> SEQUENCE: 165

Ser Ser Asp Val Gly Asn Tyr Asn Leu
1               5

<210> SEQ ID NO 166
<211> LENGTH: 3
<212> TYPE: PRT
<213> ORGANISM: Artificial sequence
<220> FEATURE:
<223> OTHER INFORMATION: Synthetic peptide

<400> SEQUENCE: 166

Glu Val Ser
1

<210> SEQ ID NO 167
<211> LENGTH: 9
<212> TYPE: PRT
<213> ORGANISM: Artificial sequence
<220> FEATURE:
<223> OTHER INFORMATION: Synthetic peptide

<400> SEQUENCE: 167

Cys Ser Tyr Ala Gly Ser Ser Gly Val
1               5

<210> SEQ ID NO 168
<211> LENGTH: 6
<212> TYPE: PRT
<213> ORGANISM: Artificial sequence
<220> FEATURE:
<223> OTHER INFORMATION: Synthetic peptide

<400> SEQUENCE: 168

Gln Gly Ile Ser Asn Tyr
1               5

<210> SEQ ID NO 169
<211> LENGTH: 3
<212> TYPE: PRT
<213> ORGANISM: Artificial sequence
<220> FEATURE:
<223> OTHER INFORMATION: Synthetic peptide

<400> SEQUENCE: 169

Ala Ala Ser
1

<210> SEQ ID NO 170
<211> LENGTH: 9
<212> TYPE: PRT
<213> ORGANISM: Artificial sequence
<220> FEATURE:
<223> OTHER INFORMATION: Synthetic peptide

<400> SEQUENCE: 170

Gln Gln Tyr Asn Thr Tyr Pro Pro Thr
1               5
```

```
<210> SEQ ID NO 171
<211> LENGTH: 9
<212> TYPE: PRT
<213> ORGANISM: Artificial sequence
<220> FEATURE:
<223> OTHER INFORMATION: Synthetic peptide

<400> SEQUENCE: 171

Ser Ser Asn Ile Gly Ala Gly Tyr Asp
1               5

<210> SEQ ID NO 172
<211> LENGTH: 3
<212> TYPE: PRT
<213> ORGANISM: Artificial sequence
<220> FEATURE:
<223> OTHER INFORMATION: Synthetic peptide

<400> SEQUENCE: 172

Gly Asn Ser
1

<210> SEQ ID NO 173
<211> LENGTH: 12
<212> TYPE: PRT
<213> ORGANISM: Artificial sequence
<220> FEATURE:
<223> OTHER INFORMATION: Synthetic peptide

<400> SEQUENCE: 173

Gln Ser His Asp Ser Ser Leu Asn Asp Phe Asn Val
1               5                   10

<210> SEQ ID NO 174
<211> LENGTH: 6
<212> TYPE: PRT
<213> ORGANISM: Artificial sequence
<220> FEATURE:
<223> OTHER INFORMATION: Synthetic peptide

<400> SEQUENCE: 174

Gly Leu Pro Gln Ala Tyr
1               5

<210> SEQ ID NO 175
<211> LENGTH: 3
<212> TYPE: PRT
<213> ORGANISM: Artificial sequence
<220> FEATURE:
<223> OTHER INFORMATION: Synthetic peptide

<400> SEQUENCE: 175

Lys Asp Thr
1

<210> SEQ ID NO 176
<211> LENGTH: 11
<212> TYPE: PRT
<213> ORGANISM: Artificial sequence
<220> FEATURE:
<223> OTHER INFORMATION: Synthetic peptide

<400> SEQUENCE: 176

Gln Ser Ala Asp Ser Ile Gly Thr Asn Val Ile
1               5                   10
```

```
<210> SEQ ID NO 177
<211> LENGTH: 6
<212> TYPE: PRT
<213> ORGANISM: Artificial sequence
<220> FEATURE:
<223> OTHER INFORMATION: Synthetic peptide

<400> SEQUENCE: 177

Gln Gly Ile Ser Ser Tyr
1               5

<210> SEQ ID NO 178
<211> LENGTH: 3
<212> TYPE: PRT
<213> ORGANISM: Artificial sequence
<220> FEATURE:
<223> OTHER INFORMATION: Synthetic peptide

<400> SEQUENCE: 178

Ala Ala Ser
1

<210> SEQ ID NO 179
<211> LENGTH: 9
<212> TYPE: PRT
<213> ORGANISM: Artificial sequence
<220> FEATURE:
<223> OTHER INFORMATION: Synthetic peptide

<400> SEQUENCE: 179

Gln Gln Phe Asn Ala Tyr Pro Tyr Thr
1               5

<210> SEQ ID NO 180
<211> LENGTH: 6
<212> TYPE: PRT
<213> ORGANISM: Artificial sequence
<220> FEATURE:
<223> OTHER INFORMATION: Synthetic peptide

<400> SEQUENCE: 180

Asn Ile Gly Ser Lys Ser
1               5

<210> SEQ ID NO 181
<211> LENGTH: 3
<212> TYPE: PRT
<213> ORGANISM: Artificial sequence
<220> FEATURE:
<223> OTHER INFORMATION: Synthetic peptide

<400> SEQUENCE: 181

Asp Asp Ser
1

<210> SEQ ID NO 182
<211> LENGTH: 12
<212> TYPE: PRT
<213> ORGANISM: Artificial sequence
<220> FEATURE:
<223> OTHER INFORMATION: Synthetic peptide

<400> SEQUENCE: 182

Gln Val Trp Asp Ser Thr Ser Asp His Ala Cys Val
1               5                   10
```

```
<210> SEQ ID NO 183
<211> LENGTH: 6
<212> TYPE: PRT
<213> ORGANISM: Artificial sequence
<220> FEATURE:
<223> OTHER INFORMATION: Synthetic peptide

<400> SEQUENCE: 183

Pro Gly Ile Ser Thr Trp
1               5

<210> SEQ ID NO 184
<211> LENGTH: 3
<212> TYPE: PRT
<213> ORGANISM: Artificial sequence
<220> FEATURE:
<223> OTHER INFORMATION: Synthetic peptide

<400> SEQUENCE: 184

Ala Val Ser
1

<210> SEQ ID NO 185
<211> LENGTH: 9
<212> TYPE: PRT
<213> ORGANISM: Artificial sequence
<220> FEATURE:
<223> OTHER INFORMATION: Synthetic peptide

<400> SEQUENCE: 185

Gln Gln Ala Asn Ser Leu Ser Trp Thr
1               5

<210> SEQ ID NO 186
<211> LENGTH: 11
<212> TYPE: PRT
<213> ORGANISM: Artificial sequence
<220> FEATURE:
<223> OTHER INFORMATION: Synthetic peptide

<400> SEQUENCE: 186

Cys Val Arg Glu Tyr Tyr Gly Leu Asp Val Trp
1               5                   10

<210> SEQ ID NO 187
<211> LENGTH: 15
<212> TYPE: PRT
<213> ORGANISM: Artificial sequence
<220> FEATURE:
<223> OTHER INFORMATION: Synthetic peptide

<400> SEQUENCE: 187

Cys Ala Thr Glu Asn Phe Asp Thr Leu Tyr Lys Phe Asp Phe Trp
1               5                   10                  15

<210> SEQ ID NO 188
<211> LENGTH: 30
<212> TYPE: PRT
<213> ORGANISM: Artificial sequence
<220> FEATURE:
<223> OTHER INFORMATION: Synthetic peptide

<400> SEQUENCE: 188

Cys Thr Lys Asp Ala Ile Pro Ser Tyr Cys Asp Ser Ile Ser Cys Tyr
1               5                   10                  15

Arg Ala Asn Gly Asn Tyr Asp Phe Phe Gly Met Asp Ala Trp
            20                  25                  30
```

```
<210> SEQ ID NO 189
<211> LENGTH: 13
<212> TYPE: PRT
<213> ORGANISM: Artificial sequence
<220> FEATURE:
<223> OTHER INFORMATION: Synthetic peptide

<400> SEQUENCE: 189

Cys Ala Arg Val Val Gly Leu Val Ala Phe Asp Val Trp
1               5                   10

<210> SEQ ID NO 190
<211> LENGTH: 19
<212> TYPE: PRT
<213> ORGANISM: Artificial sequence
<220> FEATURE:
<223> OTHER INFORMATION: Synthetic peptide

<400> SEQUENCE: 190

Cys Val Lys Ala Ser Asp Arg Gly Tyr Thr Gly Tyr Asp Thr Ser Phe
1               5                   10                  15

Asp Tyr Trp

<210> SEQ ID NO 191
<211> LENGTH: 16
<212> TYPE: PRT
<213> ORGANISM: Artificial sequence
<220> FEATURE:
<223> OTHER INFORMATION: Synthetic peptide

<400> SEQUENCE: 191

Cys Thr Lys Asp Ala Glu Asn Gln Leu Leu Tyr Trp Phe Asp Pro Trp
1               5                   10                  15

<210> SEQ ID NO 192
<211> LENGTH: 18
<212> TYPE: PRT
<213> ORGANISM: Artificial sequence
<220> FEATURE:
<223> OTHER INFORMATION: Synthetic peptide

<400> SEQUENCE: 192

Cys Ala Arg Gly Asn Leu Gln Arg Pro Gly Val Tyr Phe Gly Leu Asp
1               5                   10                  15

Val Trp

<210> SEQ ID NO 193
<211> LENGTH: 16
<212> TYPE: PRT
<213> ORGANISM: Artificial sequence
<220> FEATURE:
<223> OTHER INFORMATION: Synthetic peptide

<400> SEQUENCE: 193

Cys Ala Arg Ala Phe Arg Gly Gly Pro Asn Leu Pro Pro Asp Tyr Trp
1               5                   10                  15

<210> SEQ ID NO 194
<211> LENGTH: 17
<212> TYPE: PRT
<213> ORGANISM: Artificial sequence
<220> FEATURE:
<223> OTHER INFORMATION: Synthetic peptide
```

```
<400> SEQUENCE: 194

Cys Ala Lys Thr Pro Asp Thr Ala Met Gly Glu Asp Val Phe Asp Ile
1               5                   10                  15

Trp

<210> SEQ ID NO 195
<211> LENGTH: 17
<212> TYPE: PRT
<213> ORGANISM: Artificial sequence
<220> FEATURE:
<223> OTHER INFORMATION: Synthetic peptide

<400> SEQUENCE: 195

Cys Ala Lys Glu Leu Ala Thr Ser Gly Val Val Glu Pro Leu Asp Ser
1               5                   10                  15

Trp

<210> SEQ ID NO 196

<400> SEQUENCE: 196

000

<210> SEQ ID NO 197
<211> LENGTH: 20
<212> TYPE: PRT
<213> ORGANISM: Artificial sequence
<220> FEATURE:
<223> OTHER INFORMATION: Synthetic peptide

<400> SEQUENCE: 197

Cys Val Arg Asp Met Gly Pro Gly Ala Val His Phe Tyr Phe Tyr Gly
1               5                   10                  15

Met Asp Val Trp
            20

<210> SEQ ID NO 198
<211> LENGTH: 16
<212> TYPE: PRT
<213> ORGANISM: Artificial sequence
<220> FEATURE:
<223> OTHER INFORMATION: Synthetic peptide

<400> SEQUENCE: 198

Cys Val Lys Asp Arg Ala Gly Trp Phe Gly Asn Tyr Phe Asp Tyr Trp
1               5                   10                  15

<210> SEQ ID NO 199
<211> LENGTH: 17
<212> TYPE: PRT
<213> ORGANISM: Artificial sequence
<220> FEATURE:
<223> OTHER INFORMATION: Synthetic peptide

<400> SEQUENCE: 199

Cys Ala Arg Val Gln Asp Phe Gly His Tyr Glu Gly Gly Tyr Gly Tyr
1               5                   10                  15

Trp

<210> SEQ ID NO 200
<211> LENGTH: 19
<212> TYPE: PRT
<213> ORGANISM: Artificial sequence
```

```
<220> FEATURE:
<223> OTHER INFORMATION: Synthetic peptide

<400> SEQUENCE: 200

Cys Val Lys Asp Trp Gly Ile Arg Gly Ile Tyr Tyr Pro Ser Gly Met
1               5                   10                  15

Asp Val Trp

<210> SEQ ID NO 201
<211> LENGTH: 19
<212> TYPE: PRT
<213> ORGANISM: Artificial sequence
<220> FEATURE:
<223> OTHER INFORMATION: Synthetic peptide

<400> SEQUENCE: 201

Cys Ala Thr Asp Tyr Cys Ser Ser Thr Ser Cys Asn Thr Gly Ala Pro
1               5                   10                  15

Val Asn Trp

<210> SEQ ID NO 202
<211> LENGTH: 19
<212> TYPE: PRT
<213> ORGANISM: Artificial sequence
<220> FEATURE:
<223> OTHER INFORMATION: Synthetic peptide

<400> SEQUENCE: 202

Cys Ala Lys Asp Leu Gly Arg Ala Tyr Ser Ser Gly Trp Tyr Leu Phe
1               5                   10                  15

Asp Tyr Trp

<210> SEQ ID NO 203
<211> LENGTH: 29
<212> TYPE: PRT
<213> ORGANISM: Artificial sequence
<220> FEATURE:
<223> OTHER INFORMATION: Synthetic peptide

<400> SEQUENCE: 203

Cys Ala Arg Val Val Gly Gly Tyr Tyr Asp Asn Arg Gly Tyr Tyr
1               5                   10                  15

Arg Gly Pro Pro Thr Pro Leu Tyr Tyr Phe Asp Tyr Trp
                20                  25

<210> SEQ ID NO 204
<211> LENGTH: 11
<212> TYPE: PRT
<213> ORGANISM: Artificial sequence
<220> FEATURE:
<223> OTHER INFORMATION: Synthetic peptide

<400> SEQUENCE: 204

Cys Gln His Leu Asn Gly Tyr Pro Tyr Ser Phe
1               5                   10

<210> SEQ ID NO 205
<211> LENGTH: 11
<212> TYPE: PRT
<213> ORGANISM: Artificial sequence
<220> FEATURE:
<223> OTHER INFORMATION: Synthetic peptide
```

```
<400> SEQUENCE: 205

Cys Gln Gln Tyr Asp Asn Leu Pro Arg Thr Phe
1               5                   10

<210> SEQ ID NO 206
<211> LENGTH: 11
<212> TYPE: PRT
<213> ORGANISM: Artificial sequence
<220> FEATURE:
<223> OTHER INFORMATION: Synthetic peptide

<400> SEQUENCE: 206

Cys Gln Gln Tyr Asp Asn Leu Pro Arg Thr Phe
1               5                   10

<210> SEQ ID NO 207
<211> LENGTH: 13
<212> TYPE: PRT
<213> ORGANISM: Artificial sequence
<220> FEATURE:
<223> OTHER INFORMATION: Synthetic peptide

<400> SEQUENCE: 207

Cys Ala Ala Trp Asp Asp Ser Leu Ser Gly Tyr Val Phe
1               5                   10

<210> SEQ ID NO 208
<211> LENGTH: 10
<212> TYPE: PRT
<213> ORGANISM: Artificial sequence
<220> FEATURE:
<223> OTHER INFORMATION: Synthetic peptide

<400> SEQUENCE: 208

Cys Gln Gln Thr Tyr Thr Asn Pro Thr Phe
1               5                   10

<210> SEQ ID NO 209
<211> LENGTH: 12
<212> TYPE: PRT
<213> ORGANISM: Artificial sequence
<220> FEATURE:
<223> OTHER INFORMATION: Synthetic peptide

<400> SEQUENCE: 209

Cys Ser Ser Tyr Ala Ala Asn Asn Asn Leu Leu Phe
1               5                   10

<210> SEQ ID NO 210
<211> LENGTH: 13
<212> TYPE: PRT
<213> ORGANISM: Artificial sequence
<220> FEATURE:
<223> OTHER INFORMATION: Synthetic peptide

<400> SEQUENCE: 210

Cys Ala Thr Trp Asp Asp Ser Leu Ser Gly Trp Val Phe
1               5                   10

<210> SEQ ID NO 211
<211> LENGTH: 13
<212> TYPE: PRT
<213> ORGANISM: Artificial sequence
<220> FEATURE:
<223> OTHER INFORMATION: Synthetic peptide
```

```
<400> SEQUENCE: 211

Cys Ala Thr Trp Asp Asp Ser Leu Ser Gly Arg Val Phe
1               5                   10

<210> SEQ ID NO 212
<211> LENGTH: 11
<212> TYPE: PRT
<213> ORGANISM: Artificial sequence
<220> FEATURE:
<223> OTHER INFORMATION: Synthetic peptide

<400> SEQUENCE: 212

Cys Gln Gln Tyr Gly Asn Thr Pro Phe Thr Phe
1               5                   10

<210> SEQ ID NO 213
<211> LENGTH: 13
<212> TYPE: PRT
<213> ORGANISM: Artificial sequence
<220> FEATURE:
<223> OTHER INFORMATION: Synthetic peptide

<400> SEQUENCE: 213

Cys Gln Val Trp Asp Ser Ser Ser Asn His Pro Val Phe
1               5                   10

<210> SEQ ID NO 214
<211> LENGTH: 11
<212> TYPE: PRT
<213> ORGANISM: Artificial sequence
<220> FEATURE:
<223> OTHER INFORMATION: Synthetic peptide

<400> SEQUENCE: 214

Cys Cys Ser Tyr Ala Gly Ser Ser Gly Val Phe
1               5                   10

<210> SEQ ID NO 215
<211> LENGTH: 11
<212> TYPE: PRT
<213> ORGANISM: Artificial sequence
<220> FEATURE:
<223> OTHER INFORMATION: Synthetic peptide

<400> SEQUENCE: 215

Cys Gln Gln Tyr Asn Thr Tyr Pro Pro Thr Phe
1               5                   10

<210> SEQ ID NO 216
<211> LENGTH: 14
<212> TYPE: PRT
<213> ORGANISM: Artificial sequence
<220> FEATURE:
<223> OTHER INFORMATION: Synthetic peptide

<400> SEQUENCE: 216

Cys Gln Ser His Asp Ser Ser Leu Asn Asp Phe Asn Val Phe
1               5                   10

<210> SEQ ID NO 217
<211> LENGTH: 11
<212> TYPE: PRT
<213> ORGANISM: Artificial sequence
<220> FEATURE:
<223> OTHER INFORMATION: Synthetic peptide
```

```
<400> SEQUENCE: 217

Cys Gln Gln Tyr Asp Asn Leu Pro Arg Thr Phe
1               5                   10

<210> SEQ ID NO 218
<211> LENGTH: 11
<212> TYPE: PRT
<213> ORGANISM: Artificial sequence
<220> FEATURE:
<223> OTHER INFORMATION: Synthetic peptide

<400> SEQUENCE: 218

Cys Gln Gln Phe Asn Ala Tyr Pro Tyr Thr Phe
1               5                   10

<210> SEQ ID NO 219
<211> LENGTH: 14
<212> TYPE: PRT
<213> ORGANISM: Artificial sequence
<220> FEATURE:
<223> OTHER INFORMATION: Synthetic peptide

<400> SEQUENCE: 219

Cys Gln Val Trp Asp Ser Thr Ser Asp His Ala Cys Val Phe
1               5                   10

<210> SEQ ID NO 220
<211> LENGTH: 11
<212> TYPE: PRT
<213> ORGANISM: Artificial sequence
<220> FEATURE:
<223> OTHER INFORMATION: Synthetic peptide

<400> SEQUENCE: 220

Cys Gln Gln Ala Asn Ser Leu Ser Trp Thr Phe
1               5                   10
```

ANTIBODY-MEDIATED NEUTRALIZATION OF CHIKUNGUNYA VIRUS

PRIORITY CLAIM

This application is a national phase application under 35 U.S.C. § 371 of International Application No. PCT/US2019/012313, filed Jan. 4, 2019, which claims benefit of priority to U.S. Provisional Application Serial No. 62/614,010, filed Jan. 5, 2018, the entire contents of each of which are hereby incorporated by reference.

FEDERAL FUNDING

This invention was made with government support under grant numbers R01 AI114816, HHSN272201400018C, W31P4Q-13-1-0003 and W911NF-13-1-0417 awarded by the National Institutes of Health and the Defense Advanced Projects Research Agency. The government has certain rights in the invention.

BACKGROUND

1. Field of the Disclosure

The present disclosure relates generally to the fields of medicine, infectious disease, and immunology. More particular, the disclosure relates to antibodies that neutralize Chikungunya virus.

2. Background

Chikungunya virus (CHIKV) is an enveloped, positive-sense RNA virus in the Alphavirus genus of the Togaviridae family and is transmitted by *Aedes* mosquitoes. The mature CHIKV virion contains two glycoproteins, E1 and E2, which are generated from a precursor polyprotein, p62-E1, by proteolytic cleavage. E2 functions in viral attachment, whereas E1 mediates membrane fusion to allow viral entry (Kielian et al., 2010). In humans, CHIKV infection causes fever and joint pain, which may be severe and last in some cases for years (Schilte et al., 2013; Sissoko et al., 2009; Staples et al., 2009). CHIKV has caused outbreaks in most regions of sub-Saharan Africa and also in parts of Asia, Europe, and the Indian and Pacific Oceans. In December 2013, the first transmission of CHIKV in the Western Hemisphere occurred, with autochthonous cases identified in St. Martin (CDC 2013). The virus spread rapidly to virtually all islands in the Caribbean as well as Central, South, and North America. In less than one year, over a million suspected CHIKV cases in the Western Hemisphere were reported, and endemic transmission in more than 40 countries, including the United States was documented (CDC, 2014). At present, there is no licensed vaccine or antiviral therapy to prevent or treat CHIKV infection.

Although mechanisms of protective immunity to CHIKV infection in humans are not fully understood, the humoral response controls infection and limits tissue injury (Chu et al., 2013; Hallengard et al., 2014; Hawman et al., 2013; Kam et al., 2012b; Lum et al., 2013; Pal et al., 2013). Immune human γ-globulin neutralizes infectivity in cultured cells and prevents morbidity in mice when administered up to 24 hours after viral inoculation (Couderc et al., 2009). Several murine monoclonal antibodies (mAbs) that neutralize CHIKV infection have been described (Brehin et al., 2008; Goh et al., 2013; Masrinoul et al., 2014; Pal et al., 2013; Pal et al., 2014), including some with efficacy when used in combination to treat mice or nonhuman primates following CHIKV challenge (Pal et al., 2013; Pal et al., 2014). In comparison, a limited number of human CHIKV mAbs have been reported, the vast majority of which exhibit modest neutralizing activity (Fong et al., 2014; Fric et al., 2013; Lee et al., 2011; Selvarajah et al., 2013; Warter et al., 2011).

SUMMARY

Thus, in accordance with the present disclosure, there is provided a method of a method of detecting a Chikungunya virus infection in a subject comprising (a) contacting a sample from said subject with an antibody or antibody fragment having clone-paired heavy and light chain CDR sequences from Tables 3 and 4, respectively; and (b) detecting Chikungunya virus in said sample by binding of said antibody or antibody fragment to a Chikungunya virus antigen in said sample. The sample may be a body fluid, such as blood, sputum, tears, saliva, mucous or serum, urine or feces. Detection may comprise ELISA, RIA or Western blot. The method may further comprise performing steps (a) and (b) a second time and determining a change in the Chikungunya virus antigen levels as compared to the first assay.

The antibody or antibody fragment may be encoded by clone-paired variable sequences as set forth in Table 1, or encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, $F(ab')_2$ fragment, or Fv fragment.

Also provided is a method of treating a subject infected with Chikungunya virus or reducing the likelihood of infection of a subject at risk of contracting Chikungunya virus comprising treating said subject with an antibody or antibody fragment having clone-paired heavy and light chain CDR sequences from Tables 3 and 4, respectively. By treating, the inventors contemplate administration of an antibody or antibody fragment, or in vivo synthesis of an antibody or antibody fragment following delivery of a nucleic acid coding therefor, such as an RNA sequence, RNA sequences, DNA sequence, DNA sequences, vector, or vectors encoding the antibody or antibody fragment. The antibody or antibody fragment may be encoded by clone-paired variable sequences as set forth in Table 1, or encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, and/or may be a chimeric antibody. The antibody or antibody fragment may be administered prior to infection, or administered after infection. Delivering may comprise antibody or antibody fragment administration, or genetic delivery with an RNA or DNA sequence or vector encoding the antibody or antibody fragment.

In yet another embodiment, there is provided a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1, or encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be a chimeric antibody, or is bispecific antibody that targets a Chikungunya virus antigen other than glycoprotein. The antibody may be an IgG. The antibody or antibody fragment may further comprise a cell penetrating peptide and/or is an intrabody.

In still yet another embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired variable sequences as set forth in Table 1, or encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be a chimeric antibody and/or an IgG. The antibody or antibody fragment may further comprise a cell penetrating peptide and/or is an intrabody.

In a further embodiment, there is provided a method of determining the antigenic integrity of an antigen comprising (a) contacting a sample comprising said antigen with a first antibody or antibody fragment having clone-paired heavy and light chain CDR sequences from Tables 3 and 4, respectively; and (b) determining antigenic integrity of said antigen by detectable binding of said antibody or antibody fragment to said antigen. The sample may comprise recombinantly produced antigen. The sample may comprise a vaccine formulation or vaccine production batch. Detection may comprise ELISA, RIA, western blot, a biosensor using surface plasmon resonance or biolayer interferometry, or flow cytometric staining. The antibody or antibody fragment may be encoded by clone-paired variable sequences as set forth in Table 1, or encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The method may further comprise performing steps (a) and (b) a second time to determine the antigenic stability of the antigen over time.

The method may further comprise (c) contacting a sample comprising said antigen with a second antibody or antibody fragment having clone-paired heavy and light chain CDR sequences from Tables 3 and 4, respectively; and (d) determining antigenic integrity of said antigen by detectable binding of said antibody or antibody fragment to said antigen. The second antibody or antibody fragment may be encoded by clone-paired variable sequences as set forth in Table 1, or encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. The second antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The second antibody fragment may be a recombinant scFv (single chain fragment variable) antibody, Fab fragment, F(ab')$_2$ fragment, or Fv fragment. The method may further comprise performing steps (c) and (d) a second time to determine the antigenic stability of the antigen over time.

In still yet a further embodiment, there is provided a pharmaceutical composition comprising:
  a first polynucleotide comprising a first nucleic acid sequence encoding a first polypeptide comprising a heavy chain variable region comprising three heavy chain CDR sequences from an antibody clone identified in Table 3;
  a second polynucleotide comprising a second nucleic acid sequence encoding a second polypeptide comprising a light chain variable region comprising three light chain CDR sequences from an antibody clone identified in Table 4,
  wherein the light chain CDR sequences are cloned-paired with the heavy chain CDR sequences from Table 3,
wherein the first polypeptide when paired with the second polypeptide forms an anti-Chikungunya virus antibody or an anti-Chikungunya virus antibody fragment. The antibody or antibody fragment may comprise light and heavy chain variable sequences according to clone-paired sequences from Table 2. The antibody may be an IgG. The pharmaceutical composition may comprise a delivery vehicle. The first polynucleotide and the second polynucleotide may each be DNA sequences or may each be mRNA sequences. The first polynucleotide and the second polynucleotide may each comprise non-natural, modified nucleotides. The first polynucleotide and the second polynucleotide may each comprise a heterologous 5' UTR sequence. The first polynucleotide and the second polynucleotide may each comprise a heterologous 3' UTR sequence. The first polynucleotide and the second polynucleotide may each comprise a heterologous 5' UTR sequence and a heterologous 3' UTR sequence. A "heterologous" UTR sequence is a UTR sequence other than a naturally occurring UTR sequence present in a naturally occurring mRNA that encodes an antibody heavy or light chain comprising a variable region depicted in Table 2. Also provided is a method of treating a subject infected with Chikungunya virus or reducing the likelihood of infection of a subject at risk of contracting Chikungunya virus, comprising administering to the subject an effective amount of the pharmaceutical composition of this paragraph.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 2. ELISA (OD) results of plates are shown for CHKV screen.

FIG. 3. ELISA (OD) result of plates are shown for Mayaro virus screen.

FIG. 4. ELISA (OD) result of plates are shown for Ross River virus screen.

FIG. 5. EBV lines selected for electrofusion.

FIG. 7. Neutralization curves for two additional clones, CHKV-48 neutralizes.

FIG. 9. Summary of activity of chikungunya clones recovered and not recovered.

DESCRIPTION OF ILLUSTRATIVE EMBODIMENTS

Figure 1:
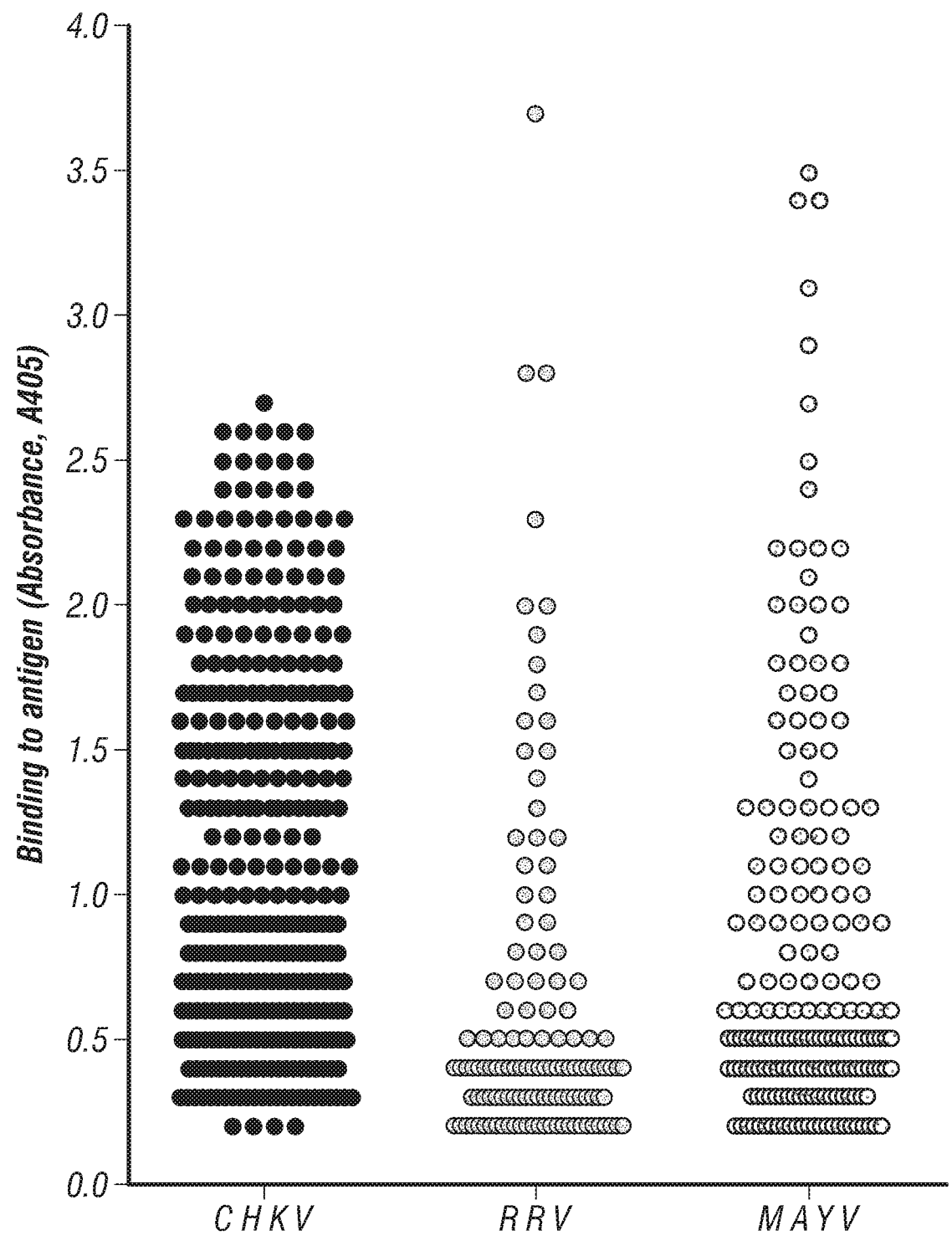
FIG. 1. Screening B cell culture supernatants by virus capture ELISA.
Figure 6:
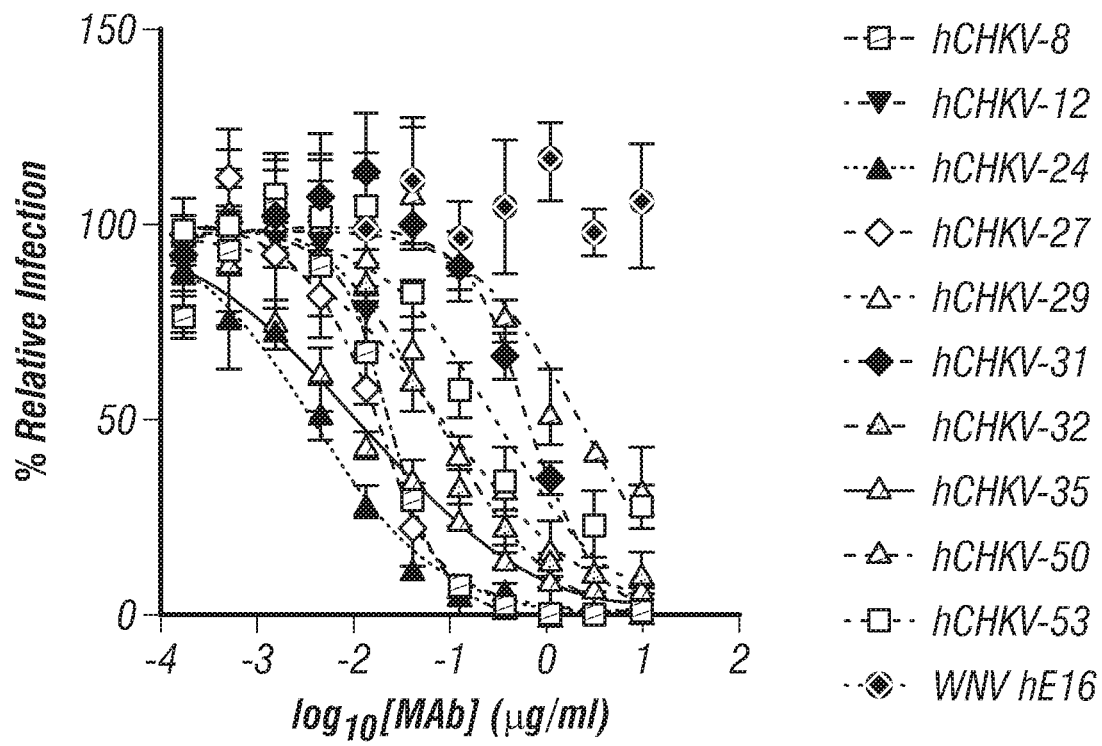
FIG. 6. Neutralization curves. Top panel shows the most potent clones. Middle panel shows poorly neutralizing clones. Bottom panel clones show no apparent neutralization of Mayaro.
Figure 6:
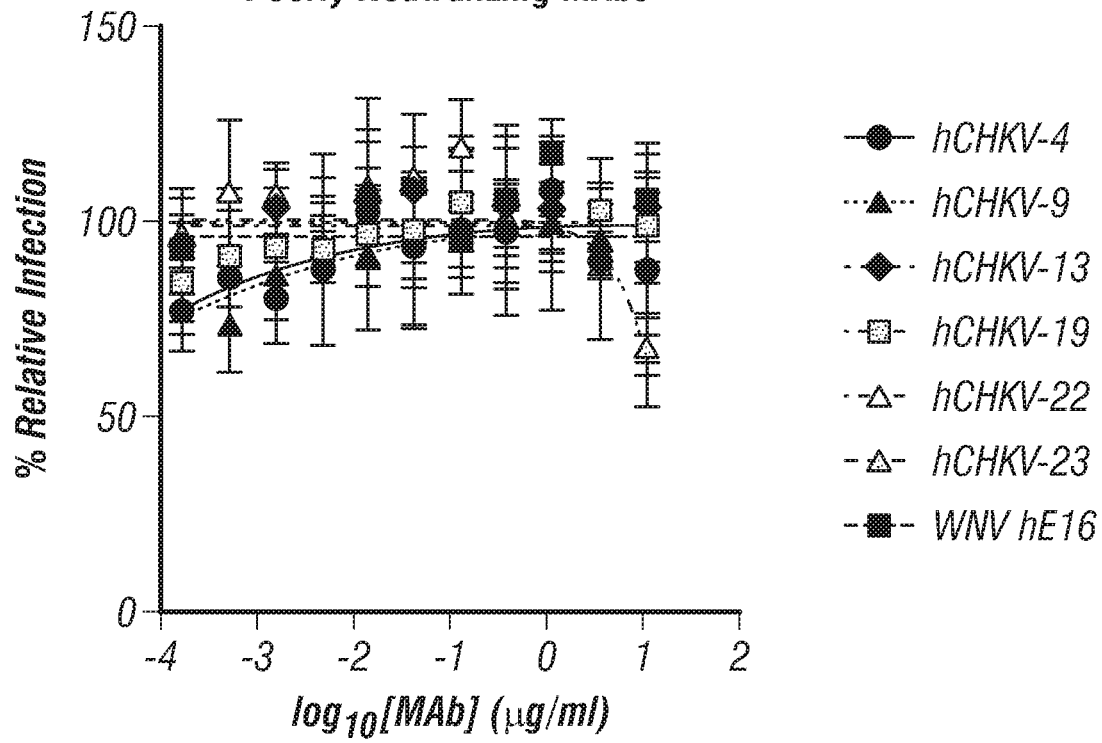
Figure 8:
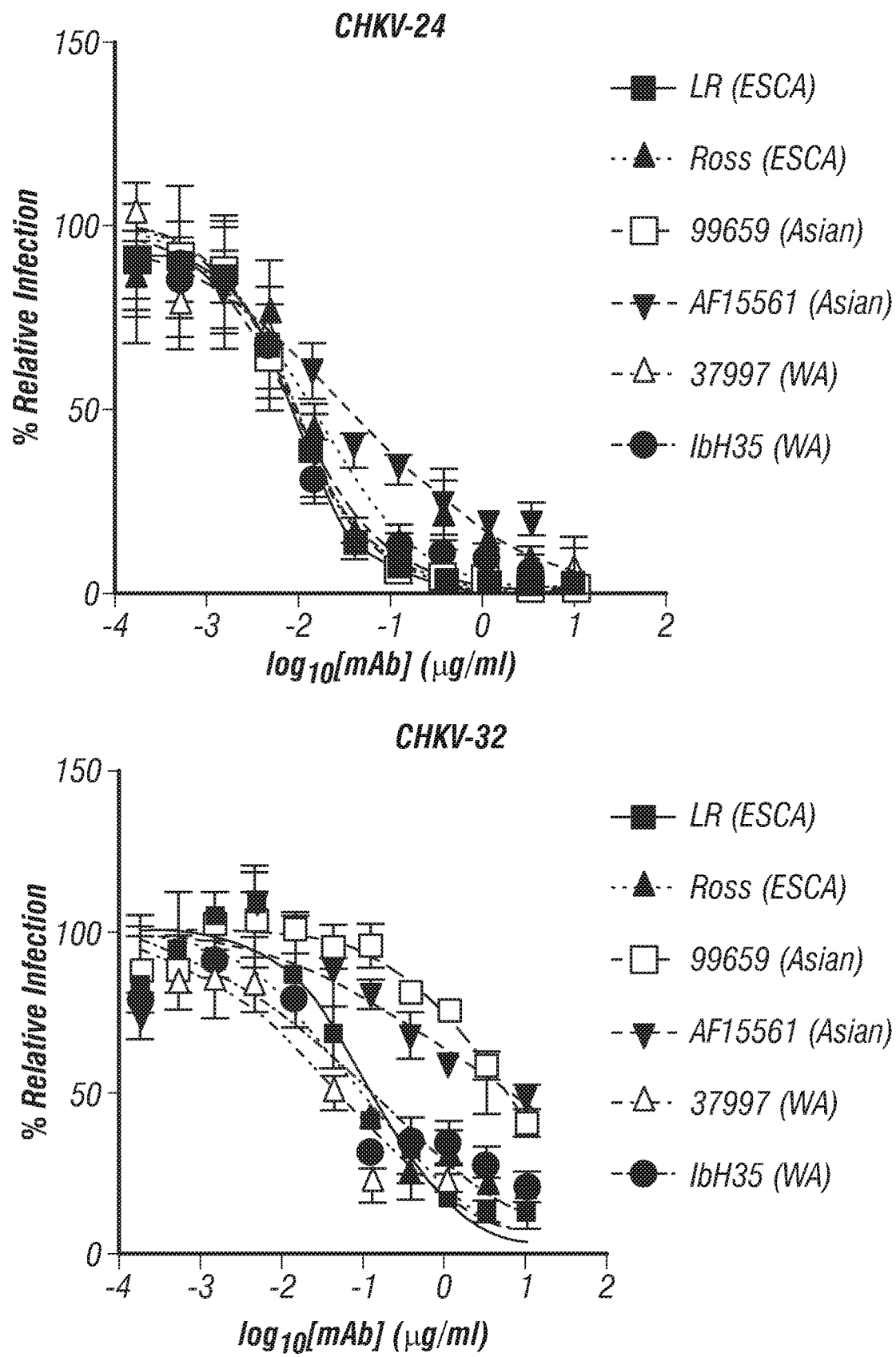
FIG. 8. Neutralization of diverse viruses (breadth). Top panel: CHKV-24. Middle panel: CHKV-32. Bottom panel: WNV negative control.

The inventors isolated a large panel of human mAbs that bind to and neutralize CHKV. These and other aspects of the disclosure are described in detail below.

I. Chikungunya and Chikungunya Virus

Chikungunya is an infection caused by the chikungunya virus. It features sudden onset fever usually lasting two to seven days, and joint pains typically lasting weeks or months but sometimes years. The mortality rate is a little less than 1 in 1000, with the elderly most likely to die. The virus is passed to humans by two species of mosquito of the genus Aedes: *A. albopictus* and *A. aegypti*. Animal reservoirs of the virus include monkeys, birds, cattle, and rodents. This is in contrast to dengue, for which only primates are hosts.

The best means of prevention is overall mosquito control and the avoidance of bites by any infected mosquitoes. No specific treatment is known, but medications can be used to reduce symptoms. Rest and fluids may also be useful.

The incubation period of chikungunya disease ranges from two to twelve days, typically three to seven. Between 72 and 97% of those infected will develop symptoms. Symptoms include sudden onset, sometimes biphasic fever typically lasting from a few days to a week, sometimes up to ten days, usually above 39° C. (102° F.) and sometimes reaching 41° C. (104° F.), and strong joint pain or stiffness usually lasting weeks or months but sometimes lasting years. Rash (usually maculopapular), muscle pain, headache, fatigue, nausea or vomiting may also be present. Inflammation of the eyes may present as iridocyclitis, or uveitis, and retina lesions may occur. Typically, the fever lasts for two days and then ends abruptly. However, headache, insomnia and an extreme degree of prostration last for a variable period, usually about five to seven days.

Observations during recent epidemics have suggested chikungunya may cause long-term symptoms following acute infection. During the La Reunion outbreak in 2006, more than 50% of subjects over the age of 45 reported long-term musculoskeletal pain with up to 60% of people reporting prolonged painful joints three years following initial infection. A study of imported cases in France reported that 59% of people still suffered from arthralgia two years after acute infection. Following a local epidemic of chikungunya in Italy, 66% of people reported muscle pains, joint pains, or asthenia at one year after acute infection. Long-term symptoms are not an entirely new observation; long-term arthritis was observed following an outbreak in 1979. Common predictors of prolonged symptoms are increased age and prior rheumatological disease. The cause of these chronic symptoms is currently not fully known. Markers of autoimmune or rheumatoid disease have not been found in people reporting chronic symptoms. However, some evidence from humans and animal models suggests chikungunya may be able to establish chronic infections within the host. Viral antigen was detected in a muscle biopsy of a people suffering a recurrent episode of disease three months after initial onset. Additionally, viral antigen and RNA were found in synovial macrophages of a person during a relapse of musculoskeletal disease 18 months after initial infection. Several animal models have also suggested chikungunya virus may establish persistent infections. In a mouse model, viral RNA was detected specifically in joint-associated tissue for at least 16 weeks after inoculation, and was associated with chronic synovitis. Similarly, another study reported detection of a viral reporter gene in joint tissue of mice for weeks after inoculation. In a nonhuman primate model, chikungunya virus was found to persist in the spleen for at least six weeks.

Chikungunya virus is an alphavirus with a positive-sense single-stranded RNA genome of about 11.6 kb. It is a member of the Semliki Forest virus complex and is closely related to Ross River virus, O'nyong'nyong virus, and Semliki Forest virus. In the United States, it is classified as a category C priority pathogen and work requires biosafety level III precautions. Human epithelial and endothelial cells, primary fibroblasts, and monocyte-derived macrophages are permissive for chikungunya virus in vitro, and viral replication is highly cytopathic, but susceptible to type-I and -II interferon. In vivo, chikungunya virus appears to replicate in fibroblasts, skeletal muscle progenitor cells, and myofibers.

Chikungunya virus is an alphavirus, as are the viruses that cause eastern equine encephalitis and western equine encephalitis. Chikungunya is generally spread through bites from *A. aegypti* mosquitoes, but recent research by the Pasteur Institute in Paris has suggested chikungunya virus strains in the 2005-2006 Reunion Island outbreak incurred a mutation that facilitated transmission by the Asian tiger mosquito (*A. albopictus*).

Chikungunya virus infection of *A. albopictus* was caused by a point mutation in one of the viral envelope genes (E1). Enhanced transmission of chikungunya virus by *A. albopictus* could mean an increased risk for outbreaks in other areas where the Asian tiger mosquito is present. A recent epidemic in Italy was likely perpetuated by *A. albopictus*. In Africa, chikungunya is spread by a sylvatic cycle in which the virus largely resides in other primates between human outbreaks.

Upon infection with chikungunya, the host's fibroblasts produce type-1 (alpha and beta) interferon. Mice that lack the interferon alpha receptor die in two to three days upon being exposed to $10^2$ chikungunya PFUs, while wild-type mice survive even when exposed to as many as $10^6$ PFUs of the virus. At the same time, mice that are partially type-1 deficient (IFN $\alpha/\beta+/-$) are mildly affected and experience symptoms such as muscle weakness and lethargy. Partidos et al. (2011) saw similar results with the live attenuated strain CHIKV181/25. However, rather than dying, the type-1 interferon-deficient (IFN $\alpha/\beta^{-/-}$) mice were temporarily disabled and the partially type-1 interferon-deficient mice did not have any problems.

Several studies have attempted to find the upstream components of the type-1 interferon pathway involved in the host's response to chikungunya infection. So far, no one knows the chikungunya-specific pathogen associated molecular pattern. Nonetheless, IPS-1—also known as Cardif, MAVS, and VISA—has been found to be an important factor. In 2011, White et al. found that interfering with IPS-1 decreased the phosphorylation of interferon regulatory factor 3 (IRF3) and the production of IFN-β. Other studies have found that IRF3 and IRF7 are important in an age-dependent manner. Adult mice that lack both of these regulatory factors die upon infection with chikungunya. Neonates, on the other hand, succumb to the virus if they are deficient in one of these factors.

Chikungunya counters the type-I interferon response by producing NS2, a nonstructural protein that degrades RBP1 and turns off the host cell's ability to transcribe DNA. NS2 interferes with the JAK-STAT signaling pathway and prevents STAT from becoming phosphorylated.

Common laboratory tests for chikungunya include RT-PCR, virus isolation, and serological tests. Virus isolation provides the most definitive diagnosis, but takes one to two weeks for completion and must be carried out in biosafety level III laboratories. The technique involves exposing specific cell lines to samples from whole blood and identifying chikungunya virus-specific responses. RT-PCR using nested primer pairs is used to amplify several chikungunya-specific genes from whole blood. Results can be determined in one to two days.

Serological diagnosis requires a larger amount of blood than the other methods, and uses an ELISA assay to measure chikungunya-specific IgM levels. Results require two to three days, and false positives can occur with infection via other related viruses, such as o'nyong'nyong virus and Semliki Forest virus.

The differential diagnosis may include infection with other mosquito-borne viruses, such as dengue, and influenza. Chronic recurrent polyarthralgia occurs in at least 20% of chikungunya patients one year after infection, whereas such symptoms are uncommon in dengue.

Currently, no specific treatment is available. Attempts to relieve the symptoms include the use of NSAIDs such as naproxen or paracetamol (acetaminophen) and fluids. Aspirin is not recommended. In those who have more than two weeks of arthritis, ribavirin may be useful. The effect of chloroquine is not clear. It does not appear to help acute disease, but tentative evidence indicates it might help those with chronic arthritis. Steroids do not appear useful, either.

Chikungunya is mostly present in the developing world. The epidemiology of chikungunya is related to mosquitoes, their environments, and human behavior. The adaptation of mosquitoes to the changing climate of North Africa around 5,000 years ago made them seek out environments where humans stored water. Human habitation and the mosquitoes' environments were then very closely connected. During periods of epidemics humans are the reservoir of the virus. During other times, monkey, birds and other vertebrates have served as reservoirs.

Three genotypes of this virus have been described: West African, East/Central/South African, and Asian genotypes. Explosive epidemics in Indian Ocean in 2005 and Pacific Islands in 2011, as well as now in the Americas, continue to change the distribution of genotypes.

On 28 May 2009 in Changwat Trang of Thailand, where the virus is endemic, the provincial hospital decided to deliver by Caesarean section a male baby from his chikungunya-infected mother, Khwanruethai Sutmueang, 28, a Trang native, to prevent mother-fetus virus transmission. However, after delivering the baby, the physicians discovered the baby was already infected with the virus, and put him into intensive care because the infection had left the baby unable to breathe by himself or to drink milk. The physicians presumed the virus might be able to be transmitted from a mother to her fetus, but without laboratory confirmation.

In December 2013, chikungunya was confirmed on the Caribbean island of St. Martin with 66 confirmed cases and suspected cases of around 181. This outbreak is the first time in the Western Hemisphere that the disease has spread to humans from a population of infected mosquitoes. By January 2014, the Public Health Agency of Canada reported that cases were confirmed on the British Virgin Islands, Saint-Barthelemy, Guadeloupe, Dominica, Martinique, and French Guyana. In April 2014, chikungunya was also confirmed in the Dominican Republic by the Centers for Disease Control and Prevention (CDC). By the end of April, it had spread to 14 countries in all, including Jamaica, St. Lucia, St. Kitts and Nevis, and Haiti where an epidemic was declared.

By the end of May 2014, over ten imported cases of the virus had been reported in the United States by people traveling to Florida from areas where the virus is endemic. The strain of chikungunya spreading to the U.S. from the Caribbean is most easily spread by *A. aegypti*. Concern exists that this strain of chikungunya could mutate to make the *A. albopictus* vector more efficient. If this mutation were to occur, chikungunya would be more of a public health concern to the US because the *A. albopictus* or Asian tiger mosquito is more widespread in the U.S. and is more aggressive than the *A. aegypti*.

On June 2014 six cases of the virus were confirmed in Brazil, two in the city of Campinas in the state of Sao Paulo. The six cases are Brazilian army soldiers who had recently returned from Haiti, where they were participating in the reconstruction efforts as members of the United Nations Stabilisation Mission in Haiti. The information was officially released by Campinas municipality, which considers that it has taken the appropriate actions.

On 16 Jun. 2014, Florida had a cumulative total of 42 cases. As of 11 Sep. 2014, the number of reported cases in Puerto Rico for the year was 1,636. By 28 October, that number had increased to 2,974 confirmed cases with over 10,000 cases suspected. On 17 Jun. 2014, Department of Health officials in the U.S. state of Mississippi confirmed they are investigating the first potential case in a Mississippi resident who recently travelled to Haiti. On 19 Jun. 2014, the virus had spread to Georgia, USA. On 24 Jun. 2014, a case was reported in Poinciana, Polk County, Florida, USA. On 25 Jun. 2014, the Health Department of the U.S. state of Arkansas confirmed that one person from that state is carrying chikungunya. On 26 Jun. 2014, a case was reported in the Mexican state of Jalisco.

On 17 Jul. 2014, the first chikungunya case acquired in the United States was reported in Florida by the Centers for Disease Control and Prevention. Since 2006, over 200 cases have been reported in the United States, but only in people who had traveled to other countries. This is the first time the virus was passed by mosquitoes to a person on the U.S. mainland. On 2 Sep. 2014, the Centers for Disease Control and Prevention reported that there had been seven confirmed cases of chikungunya in the United States in people who had acquired the disease locally.

On 25 Sep. 2014, official authorities in El Salvador report over 30,000 confirmed cases of this new epidemy. The new epidemic is also on the rise in Jamaica and in Barbados. There is a risk that tourists to those countries may bring the virus to their own countries. November 2014: Brazil has reported a local transmission of a different strain (genotype) of chikungunya that has never been documented in the Americas. This is an African genotype, but oddly fails to explain if it is South African or West African. The new genotype (in the Americas) is more severe than the Asian genotype which is currently spreading through the Americas, and immunity to one genotype does not confer immunity to others. French Polynesia is among other regions experiencing ongoing outbreaks.

On 7 Nov. 2014 Mexico reported an outbreak of chikungunya, acquired by local transmission, in southern state of Chiapas. The outbreak extends across the coastline from the Guatemala border to the neighboring state of Oaxaca. Health authorities have reported a cumulative load of 39 laboratory-confirmed cases (by the end of week 48). No suspect cases have been reported. In January 2015, there were 90,481 reported cases of chikungunya in Colombia.

II. Monoclonal Antibodies and Production Thereof

A. General Methods

It will be understood that monoclonal antibodies binding to Chikungunya virus will have several applications. These include the production of diagnostic kits for use in detecting and diagnosing Chikungunya virus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately 104 times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity, which in this case is for Chikungunya virus glycoprotein (GP). Those of skill in the art, by assessing the binding specificity/affinity of a given antibody using techniques well known to those of skill in the art, can determine whether such antibodies fall within the scope of the instant claims. In one aspect, there are provided monoclonal antibodies having clone-paired CDR's from the heavy and light chains as illustrated in Tables 3 and 4, respectively. Such antibodies may be produced by the clones discussed below in the Examples section using methods described herein.

In a second aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies were generated by subcloning heavy and light chain Fv DNAs from the cloning vector into an IgG plasmid vector, transfected into 293 Freestyle cells or CHO cells, and antibodies were collected an purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), $F(ab')_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within 2 is preferred, those that are within ±1 are particularly preferred, and those within 0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. 5×10$^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the V$_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

F. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. Active/Passive Immunization and Treatment/Prevention of Chikungunya Infection A. Formulation and Administration The present disclosure provides pharmaceutical compositions comprising anti-Chikungunya virus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Active vaccines are also envisioned where antibodies like those that are disclosed are produced in vivo in a subject at risk of Chikungunya virus infection. Sequences for the E1 and E2 are listed as SEQ ID NOS: 253-276 in the appended sequence listing. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, or by nebulizer. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

IV. Antibody Conjugates

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium $^{111}$, $^{59}$iron, $^{32}$ phosphorus, rhenium$^{186}$ rhenium$^{88}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugate contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouri-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. Immunodetection Methods

In still further embodiments, the present disclosure concerns immunodetection methods for binding, purifying, removing, quantifying and otherwise generally detecting Chikungunya virus and its associated antigens. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of Chikungunya virus antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing Chikungunya virus and contacting the sample with a first antibody in accordance with the present disclosure, as the case may be, under conditions effective to allow the formation of immunocomplexes.

These methods include methods for purifying Chikungunya virus or related antigens from a sample. The antibody will preferably be linked to a solid support, such as in the form of a column matrix, and the sample suspected of containing the Chikungunya virus or antigenic component will be applied to the immobilized antibody. The unwanted components will be washed from the column, leaving the Chikungunya virus antigen immunocomplexed to the immobilized antibody, which is then collected by removing the organism or antigen from the column.

The immunobinding methods also include methods for detecting and quantifying the amount of Chikungunya virus or related components in a sample and the detection and quantification of any immune complexes formed during the binding process. Here, one would obtain a sample suspected of containing Chikungunya virus or its antigens and contact the sample with an antibody that binds Chikungunya virus or components thereof, followed by detecting and quantifying the amount of immune complexes formed under the specific conditions. In terms of antigen detection, the biological sample analyzed may be any sample that is suspected of containing Chikungunya virus or Chikungunya virus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to Chikungunya virus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the Chikungunya virus or Chikungunya virus antigen is added to the wells. After binding and washing to remove non-specifically bound immune complexes, the bound antigen may be detected. Detection may be achieved by the addition of another anti-Chikungunya virus antibody that is linked to a detectable label. This type of ELISA is a simple "sandwich ELISA." Detection may also be achieved by the addition of a second anti-Chikungunya virus antibody, followed by the addition of a third antibody that has binding affinity for the second antibody, with the third antibody being linked to a detectable label.

In another exemplary ELISA, the samples suspected of containing the Chikungunya virus or Chikungunya virus antigen are immobilized onto the well surface and then contacted with the anti-Chikungunya virus antibodies of the disclosure. After binding and washing to remove non-specifically bound immune complexes, the bound anti-Chikungunya virus antibodies are detected. Where the initial anti-Chikungunya virus antibodies are linked to a detectable label, the immune complexes may be detected directly. Again, the immune complexes may be detected using a second antibody that has binding affinity for the first anti-Chikungunya virus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of Chikungunya virus antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventors propose the use of labeled Chikungunya virus monoclonal antibodies to determine the amount of Chikungunya virus antibodies in a sample. The basic format would include contacting a known amount of Chikungunya virus monoclonal antibody (linked to a detectable label) with Chikungunya virus antigen or particle. The Chikungunya virus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, the present disclosure concerns immunodetection kits for use with the immunodetection methods described above. As the antibodies may be used to detect Chikungunya virus or Chikungunya virus antigens, the antibodies may be included in the kit. The immunodetection kits will thus comprise, in suitable container means, a first antibody that binds to Chikungunya virus or Chikungunya virus antigen, and optionally an immunodetection reagent.

In certain embodiments, the Chikungunya virus antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the Chikungunya virus or Chikungunya virus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

E. Antigen Quality Control

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against our oldest public health threats, as well as new ones—malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

VI. Examples

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Isolation of human mAbs. PBMCs were obtained from a human ~5 years after documented symptomatic CHKV infection in an endemic area. B cells were transformed in 384-well plates with EBV in the presence of CpG. The supernatants from the resulting B cell lymphoblastic cells lines were screened for the presence of human CHKV-specific binding antibodies by ELISA using live CHIKV vaccine strain 181/25 virus as antigen. Transformed B cells were collected and fused to a myeloma cell line, distributed into culture plates and expansion, and selected by growth in hypoxanthine-aminopterin-thymidine medium containing ouabain. Hybridomas were cloned by single-cell sorting. Supernatants from cloned hybridomas growing in serum-free medium were collected, purified and concentrated from clarified medium by protein G chromatography.

Neutralization assays. Purified IgG mAb proteins were tested for neutralizing activity using CHKV virus replicon particles (VRPs) or each of 4 live chikungunya viruses representing diverse genetic and geographic profile. A CHIKV VRP that encoded GFP was generated by development of a three-plasmid CHIKV replicon helper system based on a plasmid containing the full-length cDNA of the CHIKV strain SL15649 (GenBank: GU189061.1) genome sequence, using PCR-based cloning methodologies. VRP were incubated with mAb in dilutions then inoculated onto Vero 81 cell monolayers for 18 hrs; infected cells and total cells (identified with a nuclear marker) were identified with a fluorescence imaging system. To determine mAb breadth and neutralization potency, the inventors used four representative live virus strains with at least one representative from each CHIKV genotype, including one prototype virus from each of the three genotypes and also a strain from the current Caribbean outbreak. Neutralizing activity was determined in a focus reduction neutralization test. Serial dilutions of purified human mAbs were incubated with 100 focus-forming units of CHIKV at 37° C. for 1 hour. MAb-virus complexes were added to Vero cells in 96-well plates, and then plaques were detected after cell fixation using immunoperoxidase detection and quantified using an ImmunoSpot 5.0.37 macroanalyzer (Cellular Technologies Ltd). $EC_{50}$ values were calculated using nonlinear regression analysis after comparison to wells inoculated with CHIKV in the absence of antibody.

E2 ELISA. Recombinant CHIKV E2 ectodomain protein (corresponding to the CHIKV-LR2006 strain) was generated in *E. coli* and adsorbed to microtiter plates. Human mAbs were applied, then bound CHKV-specific mAbs were detected with biotin-conjugated goat anti-human IgG.

Competition binding assay. The inventors identified groups of antibodies binding to the same major antigenic site by competing pairs of antibodies for binding to CHIKV-LR2006 E2 ectodomain protein containing a polyhistidine-tag attached to an Anti-Penta-His biosensor tip (ForteBio #18-5077) in an Octet Red biosensor (ForteBio).

Alanine scanning mutagenesis for epitope mapping. A CHIKV envelope protein expression construct (strain S27, Uniprot Reference #Q8JUX5) with a C-terminal V5 tag was subjected to alanine-scanning mutagenesis to generate a comprehensive mutation library. Primers were designed to mutate each residue within the E2, 6K, and E regions of the envelope proteins (residues Y326 to H1248 in the structural polyprotein) to alanine; alanine codons were mutated to serine. In total, 910 CHIKV envelope protein mutants were generated. Loss of binding of mAbs to each construct was tested using an immunofluorescence binding assay, using cellular fluorescence detected with a high-throughput flow cytometer.

Mechanism of neutralization. MAbs were interacted with VRPs before or after attachment to Vero 81 cells, and then cells were stained, imaged, and analyzed as described for VRP neutralization assays to determine at what stage mAbs exerted the antiviral effect. Fusion from within and fusion from without assays were performed as detailed in Supplemental Experimental Procedures.

In vivo protection studies in mice. Ifnar$^{-/-}$ mice were bred in pathogen-free animal facilities and infection experiments were performed in A-BSL3 facilities. Footpad injections were performed under anesthesia. For prophylaxis studies, human mAbs were administered by intraperitoneal injection to 6 week-old Ifnar$^{-/-\ mice}$ 1 day prior to subcutaneous inoculation in the footpad with 10 FFU of CHIKV-LR. For therapeutic studies, 10 FFU of CHIKV-LR was delivered 24, 48, or 60 hours prior to administration of a single dose of individual or combinations of human mAbs at specified doses.

Human subject and peripheral blood cell isolation. An otherwise healthy adult subject presented in October of 2006 with CHIKV infection. The symptoms of CHIKV infection coincided with return from a one-year visit to Sri Lanka, during which the patient spent time in urban areas (primarily Colombo), and rural settings, including rainforests and coastal areas. The patient experienced multiple insect bites over the course of the visit but remained in good health throughout the stay. On return to the U.S., the subject presented to the primary care physician with a fever (102° F.) of three days duration. The patient reported the concurrent development of bilateral joint pain in elbows and fingers, and a raised, non-pruritic rash on the back and abdomen, accompanied by general "body ache" and headache. On presentation, he appeared to be well, and in no acute distress. A mild, blanching, papular rash extended across the back, chest and abdomen (see FIG. 4). A mild conjunctivitis was noted. The skeletal exam was remarkable for tender swollen fingers, knees and elbows, which were without erythema or effusions. Muscle strength and range of motion of the affected joints were intact, but joint movement elicited pain.

Blood was drawn for a CBC, serologies and malaria smears, and the patient was discharged. The white blood cell count was $4.0 \times 10^4$ cells/mm$^3$, the hematocrit was 41% and platelet count was 180,000/mm$^3$. The total lymphocyte count was $1.0 \times 10^4$ cells/mm$^3$. Malaria smears and serologies were negative, and the patient was diagnosed tentatively as having a viral illness of unknown etiology.

The patient returned to the clinic two weeks later, afebrile, but with persistent arthralgia, most prominent in the fingers. The patient described the pain and stiffness as no better, and perhaps worse, than during his previous visit. The patient reported that an outbreak of chikungunya was occurring in the area of previous travel. Blood was drawn and serum separated and sent to CDC for PCR and serological testing, which confirmed the diagnosis of chikungunya infection.

In April 2012, five and a half years after the index infection, peripheral blood mononuclear cells (PBMCs) were isolated by density gradient separation on Ficoll without known exposure to CHIKV or other arthritogenic alphaviruses in the intervening period while living in the United States. The cells were cryopreserved and stored in liquid nitrogen until study. The protocol for recruiting and collecting blood samples from subjects was approved by the Institutional Review Boards of the University of North Carolina at Chapel Hill and the Vanderbilt University Medical Center.

Generation of human hybridomas. Cryopreserved PBMC samples were thawed rapidly at 37° C. and washed prior to transformation with Epstein-Barr virus, as described (Smith et al., 2012). Cultures were incubated at 37° C. with 5% $CO_2$ for 10 days and screened for the presence of cells secreting CHIKV-specific antibodies in the supernatant using VRP neutralizing assays and an ELISA. The inventors performed two independent transformations using separate aliquots of the same blood sample.

In the first transformation, the inventors established 3,840 cultures (10×384-well plates) containing an average of 42 transformed B cell colonies per culture, for an estimated total of about 161,000 individual B cell colonies. To screen for antibodies that display neutralizing activity against CHIKV under BSL2 conditions, the inventors developed a high-throughput fluorescence reduction neutralization assay using CHIKV replicon particles (VRPs) that express green fluorescent protein as a reporter. VRPs are virions that display the native viral glycoproteins but lack the full-length viral genome and thus are incapable of generating infectious progeny (Vander Veen et al., 2012). The inventors used VRPs derived from strain SL15649 (Morrison et al., 2011), which was isolated from Sri Lanka in 2006. SL15649 is contemporaneous to the strain that infected the donor and is likely very similar in sequence. From this experiment, the inventors identified 160 B cell cultures with supernatants that mediated neutralization at 90% inhibition, suggesting a frequency of 0.099% virus-specific B cells per total B cells (~1 in 1,000). A total of 60 of these lines inhibited at a level of >98%, and in the secondary screen, supernatants from 58 of the 60 lines contained antibodies that bound in ELISA to cell-culture-produced CHIKV (strain 181/25) captured on an immunoassay plate. The inventors selected 35 of the 58 lines with the highest neutralizing and binding activity for hybridoma fusion, identified 22 hybridomas with virus-binding supernatants after fusion and plating, and successfully isolated 14 clones for further study. In the second transformation, the inventors established 1,536 cultures (4×384-well plates) containing an average of 38 transformed B cell colonies per culture, for an estimated total of about 58,000 individual B cell colonies tested, suggesting a virus-specific B cell frequency of 0.1% (again, 1 in 1,000). In this experiment, they used a primary screen of ELISA binding to CHIKV strain 181/25 without a prior neutralizing test. The inventors identified 60 lines with ELISA optical density signal greater than four times the background level, selected the 30 B cell lines with the highest optical density signal in ELISA for fusion, identified 18 hybridomas with virus-binding supernatants after fusion and plating, and successfully isolated 16 clones for further study.

Fusion with myeloma cells. Cells from wells with supernatants capable of neutralizing CHIKV infectivity were fused with HMMA2.5 non-secreting myeloma cells as described (Smith et al., 2012). Resultant hybridomas were selected by growth in hypoxanthine-aminopterin-thymidine (HAT) medium containing ouabain, biologically cloned by single-cell FACS using a FACSAria III cell sorter (BD Biosciences) and expanded.

Human mAb production and purification. Wells containing hybridomas producing CHIKV-specific antibodies were cloned by three rounds of limiting dilution or with a ClonePix device (Molecular Devices) according to the manufacturer's instructions. Once individual clones were obtained, each hybridoma was expanded until 50% confluent in 75 cm$^2$ flasks. For antibody expression, cells were collected with a cell scraper, washed in serum-free medium (GIBCO Hybridoma-SFM from Invitrogen, 12045084), and divided equally into four 225 cm$^2$ flasks (Corning, 431082) containing 250 mL serum-free medium. Cells were incubated for 21 days before medium was clarified by centrifugation and passed through a 0.2 m sterile filter. Antibodies were purified from clarified medium by protein G chromatography (GE Life Sciences, Protein G HP Columns).

Cells. BHK-21 cells (ATCC CCL-10) were maintained in alpha minimal essential medium (uMEM; Gibco) supplemented to contain 10% fetal bovine serum (FBS) and 10% tryptose phosphate (Sigma). Vero 81 cells (ATCC CCL-81) were maintained in UMEM supplemented to contain 5% FBS. Medium for all cells was supplemented to contain 0.29 mg/mL L-glutamine (Gibco), 100 U/mL penicillin (Gibco), 100 µg/mL streptomycin (Gibco), and 500 ng/mL amphotericin B. Cells were maintained at 37° C. in a humidified atmosphere of 5% $CO_2$.

Generation of CHIKV VRP plasmid constructs. A three-plasmid CHIKV replicon helper system was derived from a plasmid containing the full-length cDNA of the CHIKV strain SL15649 (GenBank: GU189061.1) genome sequence using PCR-based cloning methodologies. A CHIKV replicon genome was constructed using a two-step process that involved the generation of an intermediate cloning vector with the CHIKV full-length structural cassette substituted with a multiple cloning site (MCS). Enhanced green fluorescent protein (eGFP) was subcloned into the multiple cloning site of this plasmid to generate pMH41 (CHIKV SL15649 eGFP replicon). The construction of a two-plasmid helper system included a multi-step cloning process that first involved the generation of a full-length structural gene helper plasmid via removal of the majority (6,891 nt) of the CHIKV non-structural cassette. The full-length structural cassette was further subdivided into two constructs, pMH38 (CHIKV SL15649 capsid helper), which is comprised of the capsid gene sequence followed by a unique AvrII restriction site, and pMH39 (CHIKV SL15649 glycoprotein helper), which contains an in-frame deletion of the capsid RNA-binding domain followed by the intact envelope glycoprotein (E3-E1) coding sequence.

Recombinant CHIKV p62-E1 production. A plasmid containing CHIKV p62 (i.e., E3 [aa S1-R64]-E2 [aa S1-E361]-16 amino acid linker-E1 [aa Y1-Q411] followed by a His tag) (Voss et al., 2010) was transfected into 293F cells using 293fectin reagent (Invitrogen). After 72 hours incubation, the supernatant was removed, and the cells were cultured for an additional 72 hours. The pooled supernatants were loaded onto a nickel agarose bead column (GoldBio) and eluted with imidazole. The protein was further purified using a Superdex S200 gel filtration column (GE Life Sciences). Fractions containing the CHIKV p62-E1 protein were pooled, frozen, and stored at −80° C.

Generation of CHIKV strain SL15649-derived VRP stocks. VRP stocks were recovered from recombinant CHIKV plasmids in a certified biological safety level 3 (BSL3) facility in biological safety cabinets in accordance with protocols approved by the Vanderbilt University Department of Environment, Health, and Safety and the Vanderbilt Institutional Biosafety Committee. The three SL15649 replicon system plasmids were linearized by digestion with NotI-HF, purified by phenol-chloroform extraction, and used as templates in transcription reactions using an mMessage mMachine SP6 transcription kit (Life Technologies) to produce capped, full-length RNA transcripts in vitro. Viral RNA transcripts were introduced into BHK21 cells by electroporation using a GenePulser electroporator. Culture supernatants containing VRPs were collected 24 hours after electroporation; supernatants were clarified by centrifugation at 855×g for 20 min, aliquoted, and stored at −80° C. VRP stocks were evaluated for propagation-competent recombinant virus by serial passage of 20% of the stock and 10% of passage 1 culture supernatant using Vero81 cells, which were examined for cytopathic effect (CPE) 72 hours after infection. Stocks were considered to have passed this safety test when CPE was not detected in the final passage. Stocks were then removed from the BSL3 laboratory.

VRP neutralization and GFP reporter assay. Vero 81 cells ($2.25 \times 10^3$ cells/well) were seeded into wells of 384-well plates and incubated at 37° C. for 24 hours. Neat hybridoma supernatant or serial dilutions of purified mAbs were incubated with VRPs at an MOI of 5 infectious units/cell in virus dilution buffer (VDB; RPMI medium containing 20 mM HEPES supplemented to contain 1% FBS) at 37° C. for 1 hour and then adsorbed to cells. Cells were incubated at 37° C. for 18 hours, stained with Hoechst stain to label nuclei, and imaged using an ImageXpress Micro XL imaging system (Molecular Devices) at the Vanderbilt High-Throughput Screening Facility. Total and CHIKV-infected cells (marked by GFP expression) were quantified using MetaXpress software (Molecular Devices) in two fields of view per well. For each antibody, $EC_{50}$ values with 95% confidence intervals were determined using nonlinear regression to fit separate logistic growth curves using the R statistics program (R.C. Team, 2014).

Virus stocks prepared as antigen for ELISA. The infectious clone plasmid for CHIKV vaccine strain 181/25 (Levitt et al., 1986 and Mainou et al., 2013) was linearized with NotI-HF and transcribed in vitro using an mMessage mMachine SP6 transcription kit (Life Technologies). Viral RNA was introduced into BHK21 cells by electroporation. Culture supernatants were harvested 24 hours later, clarified by centrifugation at 855×g for 20 min, aliquoted, and stored at −80° C.

Virus capture ELISA for hybridoma screening. Antibody binding to virus particles was performed by coating assay plates with purified mouse mAb CHK-187 (Pal et al., 2013), prepared at 1 µg/mL in 0.1 M $Na_2CO_3$ and 0.1 M $NaHCO_3$ pH 9.3 binding buffer, was used to coat ELISA plates (Nunc 242757) and incubated at 4° C. overnight. After incubating plates for 1 hour with blocking buffer (1% powdered milk and 2% goat serum in PBS with Tween 20 [PBS-T]), plates were washed five times with PBS-T and incubated with 25 µL of culture supernatant from BHK21 cell monolayers infected with CHIKV vaccine strain 181/25. After incubation at room temperature for 1 hour, plates were washed ten times with PBS, and 10 µL of B cell culture supernatant was added into 25 µL/well of blocking buffer. Plates were incubated at room temperature for 1 hour prior to washing five times with PBS-T. A secondary antibody conjugated to alkaline phosphatase (goat anti-human Fc; Meridian Life Science, W99008A) was applied at a 1:5,000 dilution in 25 L/well of blocking buffer, and plates were incubated at room temperature for 1 hour. Following five washes with PBS-T, phosphatase substrate solution (1 mg/mL phosphatase substrate in 1 M Tris aminomethane [Sigma, S0942]) was added at 25 L/well, and plates were incubated at room temperature for 2 hours before determining the optical density at 405 nm using a Biotek plate reader.

CHIKV-specific control human mAbs. In some assays, two previously described human CHIKV-specific mAbs, 5F10 and 8B10 (Warter et al., 2011), were used as positive controls. These mAbs were expressed in 293F cells (Invitrogen) following transfection with an IgG1 expression plasmid (Lonza) containing a sequence-optimized cDNA of the 5F10 and 8B10 antibody variable gene regions based on sequences provided by Cheng-I Wang and Alessandra Nardin (Singapore Immunology Network, A*STAR, Singapore).

ELISA for mAb binding to E2 protein. Recombinant CHIKV E2 ectodomain protein (corresponding to the CHIKV-LR2006 strain) was generated in E. coli as described (Pal et al., 2013) and adsorbed to microtiter plates (100 µL of a 2 µg/mL E2 protein solution in 0.1 M $Na_2CO_3$, 0.1 M $NaHCO_3$, and 0.1% $NaN_3$ [pH 9.3]) at 4° C. overnight. Plates were rinsed three times with PBS containing 0.05% Tween-20 and incubated at 37° C. for 1 hour with blocking buffer (PBS, 0.05% Tween-20, and 2% [w/v] of BSA). Primary human mAb (diluted to 10 µg/mL in blocking buffer) was added to wells at room temperature for 1 hour. Plates were rinsed three times with PBS containing 0.05% Tween-20, and secondary antibody (biotin-conjugated goat anti-human IgG (H and L chains) with minimal cross-reactivity to mouse serum proteins (Jackson ImmunoResearch Laboratories) diluted 1/20,000 in blocking buffer) and streptavidin-conjugated horseradish peroxidase (diluted in PBS with 0.05% Tween-20; Vector Laboratories) were added sequentially, each at room temperature for 1 hour with plate rinsing in between steps. After four rinses with PBS, plates were incubated at room temperature with 100 µL of TMB (3,3',5,5'-tetramethylbenzidine) chromogenic substrate solution (Dako) for 5 min, and the reaction was stopped by addition of 2 N $H2SO_4$. Product intensity was determined using an ELISA plate reader at an optical density of 450 nm.

Affinity measurements by surface plasmon resonance. Interactions of purified human mAbs and CHIKV proteins were analyzed kinetically using a Biacore T100 instrument as described (Austin et al., 2012). For the intact IgG with soluble CHIKV p62-E1, anti-human IgG antibodies (GE Life Sciences) were immobilized onto a Series S CM5 chip and used to capture anti-CHIKV or control (hu-WNV E16) antibodies. The CHIKV p62-E1 was injected over the surface at 65 µL/min for 180 sec and allowed to dissociate for 1000 sec before regeneration with 3 M $MgCl_2$ between cycles. Some antibodies did not bind to the monomeric E1 protein, therefore the inventors tested them for binding to VLPs. For the kinetic measurements with the CHIKV VLP, anti-mouse IgG antibodies (GE Life Sciences) were immobilized to capture a set of murine anti-CHIKV antibodies with sub-nanomolar affinities, which were in turn used to capture the CHIKV VLPs. Anti-CHIKV IgG or Fab was injected over the chip surface at 65 µL/min for 180 sec and allowed to dissociate for 1000 sec before regeneration with 10 mM glycine pH 1.7 between cycles. All data were processed using the Biacore Evaluation Software (Version 1.1.1) and a global 1.1 Langmuir fit of the curves. Results were obtained from at least three independent experiments.

Virus strains used in focus reduction neutralization tests. To determine mAb breadth and neutralization potency, the inventors used four representative strains with at least one representative from each CHIKV genotype, including one prototype virus from each of the three genotypes and also a strain from the current Caribbean outbreak. Strain LR2006_OPY1 (LR) (CHIKV East/Central/South African [ECSA] genotype) was provided by Stephen Higgs (Manhattan, Kans.). Strain NI 64 IbH 35 (West African genotype) and strains RSU1 and 99659 (Asian genotype; isolated in 2014 from a subject in the British Virgin Islands (Lanciotti & Valadere, 2014)) were provided by Robert Tesh (World Reference Center for Emerging Viruses and Arboviruses, Galveston, TX).

Focus reduction neutralization test (FRNT) with infectious CHIKV. Serial dilutions of purified human mAbs were incubated with 100 focus-forming units (FFU) of CHIKV at 37° C. for 1 hour. MAb-virus complexes were added to Vero cells in 96-well plates. After 90 min incubation, cells were overlaid with 1% (w/v) methylcellulose in Modified Eagle Media (MEM) supplemented to contain 2% FBS. Cells were incubated for 18 hours and fixed with 1% paraformaldehyde in PBS. Cells were incubated sequentially with 500 ng/mL of murine CHK-11 (Pal et al., 2013) and horseradish peroxidase (HRP)-conjugated goat anti-mouse IgG in PBS supplemented to contain 0.1% saponin and 0.1% bovine serum albumin (BSA). CHIKV-infected foci were visualized using TrueBlue peroxidase substrate (KPL) and quantified using an ImmunoSpot 5.0.37 macroanalyzer (Cellular Technologies Ltd). $EC_{50}$ values were calculated using nonlinear regression analysis after comparison to wells inoculated with CHIKV in the absence of antibody.

Biolayer interferometry competition binding assay. CHIKV-LR2006 E2 ectodomain protein containing a polyhistidine-tag (20 µg/mL) was immobilized onto Anti-Penta-His biosensor tips (ForteBio #18-5077) for 2 min. After determining the baseline signal in kinetics buffer (KB, 1×PBS, 0.01% BSA and 0.002% Tween 20) for 1 min, biosensor tips were immersed into wells containing primary antibody at a concentration of 100 µg/mL for 5 min and then immersed into wells containing competing mAbs at a concentration of 100 µg/mL for 5 min. The percent binding of the competing mAb in the presence of the first mAb was determined by comparing the maximal signal of the competing mAb applied after the initial mAb complex to the maximal signal of competing mAb alone. Antibodies were judged to compete for binding to the same site if maximum binding of the competing mAb was reduced to <30% binding affinity alone. Antibodies were considered non-competing if maximum binding of the competing mAb was >70% of non-competed binding. A level of 30-70% of non-competed binding was considered intermediate competition.

Mutagenesis epitope mapping. A CHIKV envelope protein expression construct (strain S27, Uniprot Reference #Q8JUX5) with a C-terminal V5 tag was subjected to alanine-scanning mutagenesis to generate a comprehensive mutation library. Primers were designed to mutate each residue within the E2, 6K, and E1 regions of the envelope proteins (residues Y326 to H1248 in the structural polyprotein) to alanine; alanine codons were mutated to serine (Fong et al., 2014). In total, 910 CHIKV envelope protein mutants were generated (98.5% coverage), sequence confirmed, and arrayed into 384-well plates. HEK-293T cells were transfected with the CHIKV mutation library in 384-well plates and incubated for 22 hours. Cells were fixed in 4% paraformaldehyde (Electron Microscopy Sciences) in PBS plus calcium and magnesium (PBS+/+) and stained with purified mAbs at 0.25 to 1.0 µg/mL or purified Fab fragments at 2.5 µg/mL diluted in 10% normal goat serum (NGS; Sigma). Primary antibody concentrations were determined using an independent immunofluorescence titration curve against wild-type CHIKV envelope proteins to ensure that signals were within the linear range of detection. Antibodies were detected using 3.75 µg/mL AlexaFluor488-conjugated secondary antibody (Jackson ImmunoResearch Laboratories) in 10% NGS. Cells were washed twice with PBS without magnesium and calcium (PBS −/−) and resuspended in Cellstripper (Cellgro) with 0.1% BSA (Sigma). Mean cellular fluorescence was detected using a high-throughput flow cytometer (HTFC, Intellicyt). Antibody reactivity against each mutant clone was calculated relative to wild-type protein reactivity by subtracting the signal from mock-transfected controls and normalizing to the signal from wild-type-transfected controls. Amino acids were identified as required for mAb binding if the corresponding alanine mutant did not react with the test mAb but did react with other CHIKV antibodies. This counter-screen strategy facilitates the exclusion of mutants that are misfolded or have an expression defect (Christian et al., 2013, Paes et al., 2009 and Selvarajah et al., 2013). Amino acids required for antibody binding were visualized on the CHIKV envelope protein crystal structure (monomer PDB ID #3N41 and trimer PDB ID #2XFB) using PyMol software.

Pre- and post-attachment neutralization assays. Vero 81 cells (ATCC CCL-81; ~7.5×10$^3$ cells/well) were seeded into wells of 96-well plates and incubated at 37° C. for ~24 hours. For pre-attachment assays, dilutions of mAb were prepared at 4° C. in virus dilution buffer (VDB) and pre-incubated with VRPs at 4° C. for 1 hour. Antibody-virus complexes were added to pre-chilled Vero 81 cells at 4° C. for 1 hour. Non-adsorbed virus was removed by three washes with VDB, and cells were incubated in complete medium at 37° C. for 18 hours. The post-attachment assay was performed similarly, except that an equivalent MOI of VRPs was first adsorbed to Vero 81 cells at 4° C. for 1 hour, unbound VRPs were removed by three washes with virus dilution buffer, and cells were incubated with pre-chilled VDB containing serial dilutions of mAb at 4° C. for 1 hour. Unbound mAbs were removed by three washes with VDB, and cells were incubated in complete medium at 37° C. for 18 hours. Cells were stained, imaged, and analyzed as described for VRP neutralization assays, with four fields of view per well, yielding a total of ~800 to 1,000 cells analyzed for GFP expression per sample.

Fusion inhibition assays. Virus fusion with the plasma membrane was assessed using an FFWO assay (Edwards & Brown, 1986). Vero 81 cells (~3.75×10$^3$ cells/well) were seeded into wells of 96-well plates and incubated at 37° C. for 24 hours. Cells were washed once with binding medium (RPMI 1640 supplemented to contain 1% FBS, 25 mM HEPES [pH 7.4] and 20 mM NH$_4$Cl to prevent infection through endosomal fusion) and incubated in binding medium at 4° C. for 15 min. Inoculum containing VRPs was diluted in binding medium and incubated with cells at 4° C. for 1 hour. Unbound VRPs were removed by two washes with binding medium. Serial dilutions of mAbs in VDB were incubated with cells at 4° C. for 1 hour, and unbound mAb was removed by two washes with VDB. FFWO was induced by the addition of pre-warmed fusion medium (RPMI 1640, 1% FBS, 25 mM HEPES, and 30 mM succinic acid at pH 5.5) at 37° C. for 2 min. In parallel wells, control medium (RPMI 1640, 1% FBS, 25 mM HEPES at pH 7.4) was added at 37° C. for two min. The medium was removed and cells were incubated in DMEM supplemented to contain 5% FBS, 20 mM NH$_4$Cl (to ensure that infection occurred only through pH-dependent plasma membrane fusion), and 25 mM HEPES [pH 7.4]). At 18 hours post infection, cells were stained, imaged, and analyzed as described, with four fields of view per well, yielding a total of 800-1,000 cells analyzed for GFP expression per sample.

In vivo protection studies in mice. This study was carried out in strict accordance with the recommendations in the Guide for the Care and Use of Laboratory Animals of the National Institutes of Health. The protocols were approved by the Institutional Animal Care and Use Committee at Washington University School of Medicine (Assurance Number: A3381-01). Ifnar$^{-/-}$ mice were bred in pathogen-free animal facilities at Washington University School of Medicine, and infection experiments were performed in A-BSL3 facilities with the approval of the Washington University Animal Studies Committee. Footpad injections were performed under anesthesia that was induced and maintained with ketamine hydrochloride and xylazine. For prophylaxis studies, human mAbs were administered by intraperitoneal injection to 6 week-old Ifnar$^{-/-}$ $^{mice}$ 1 day prior to subcutaneous inoculation in the footpad with 10 FFU of CHIKV-LR diluted in HBSS with 1% heat-inactivated FBS. For therapeutic studies, 10 FFU of CHIKV-LR was delivered 24, 48, or 60 hours prior to administration of a single dose of individual or combinations of human mAbs at specified doses.

Figure 10:
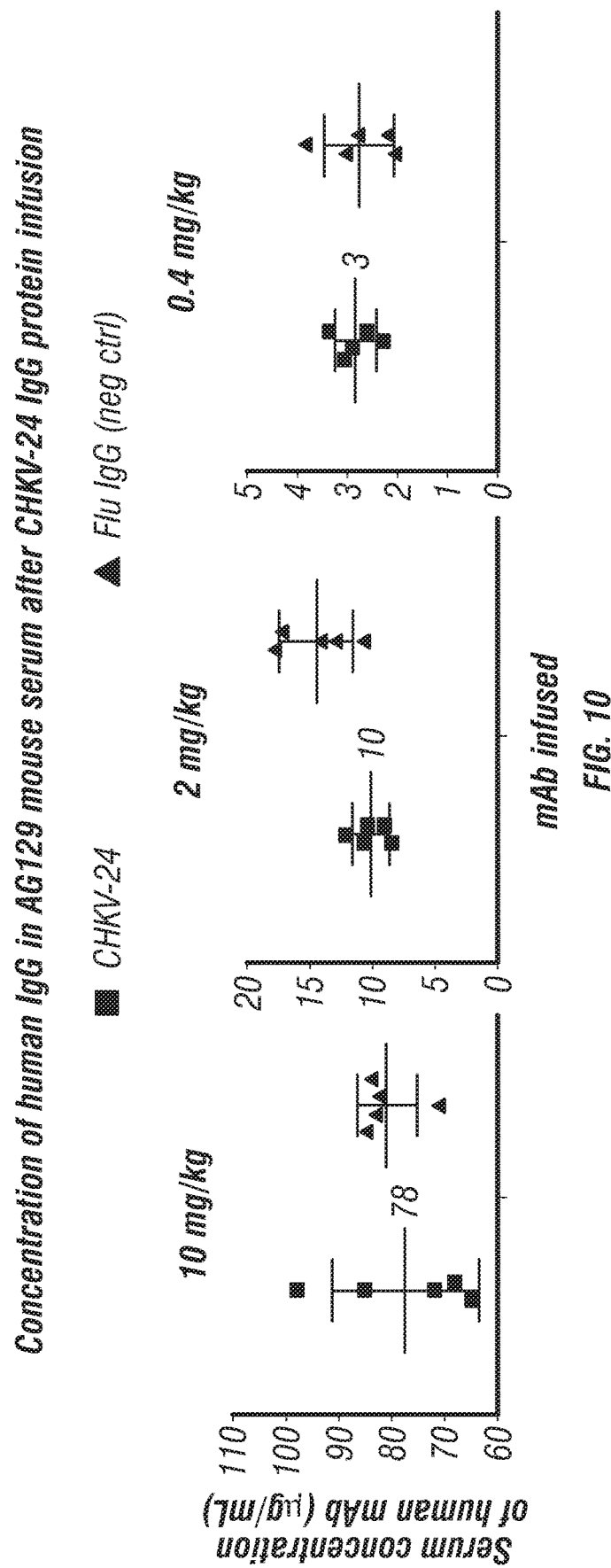
FIG. 10. Concentration of human IgG in AG129 mouse serum after CHKV-24 IgG protein infusion. Total human IgG levels were measured 24 h after infusion of purified human mAb IgG protein for CHKV-24 (red) or an irrelevant control mAb to influenza (flu; green). Animals receiving 10 mg/kg (200 µg), 2 mg/kg (40 µg) or 0.4 mg/kg (8 µg) of recombinant CHKV-24 IgG protein had mean systemic IgG concentrations of CHKV-24 of 78 µg/mL, 10 µg/mL or 3 µg/mL, respectively. The serum concentration of the influenza control antibody was similar. Five animals were tested.
Figure 11:
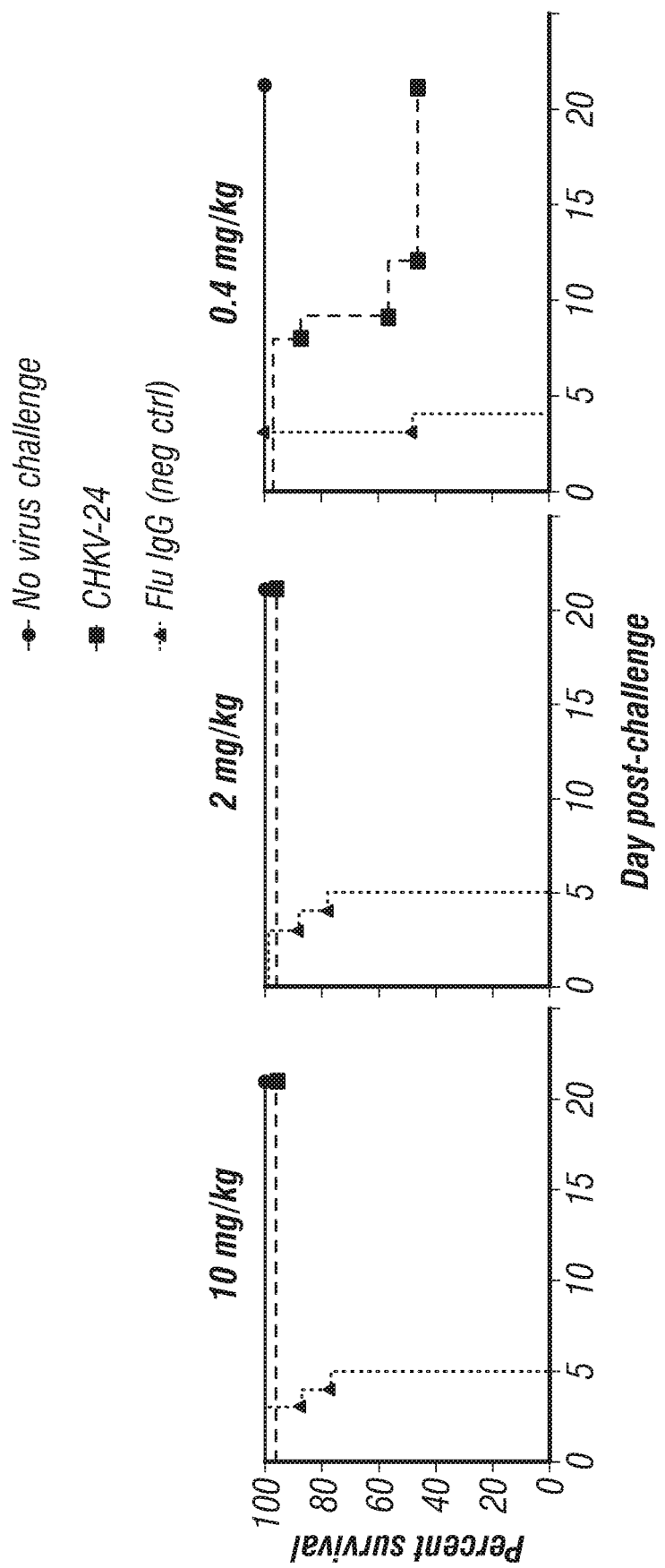
FIG. 11. Survival of AG129 mice treated with mAb CHKV-24 IgG protein and challenged with CHKV. Mice were treated with a single intravenous injection of 10 mg/kg (left), 2 mg/kg (middle), or 0.4 mg/kg (right) of mAb CHKV-24 (red) or an irrelevant human IgG to influenza A virus (flu; green) 24 h prior to virus challenge with $10^{2.5}$ $TCID_{50}$ of CHKV-LR06. The group shown in blue contained animals that were neither treated nor challenged. Challenged animals were anesthetized with isoflurane prior to subcutaneous injection in the footpad and hock of the right leg with a total volume of 0.1 mL of the diluted virus (0.05 mL each site). Kaplan-Meier survival plot is shown. Survival data were analyzed using the Wilcoxon log-rank survival analysis. ** indicates P<0.01, as compared with control. The number of animals in each group was 10. Animals receiving 2 or 10 mg/kg of CHKV-24 were completely protected (100% survival) from lethal challenge. Animals receiving 0.4 mg/kg of chikungunya IgG were partially protected (50% survival). All animals receiving the flu IgG at 10, 2 or 0.4 mg/kg succumbed (0% survival) to infection by day 5.

Protection of mice by delivery of CHKV24 mAb. AG129 mice that lack receptors for interferon-α/β and -γ are highly vulnerable to infection with CHIKV (38) and thus, this is a highly stringent model for testing antiviral compounds (39-41) or the protective efficacy of CHKV-24 mAb. Mice were treated by the intravenous route with a single administration of purified IgG for CHKV-24 mAb at doses of 10, 2 or 0.4 mg/kg. A dose-dependent concentration of human IgG in mouse serum was observed, as expected (FIG. 10). At 24 hours, mice were challenged by subcutaneous injection in the footpad and hock of the right leg with a total volume of 0.1 mL of the diluted virus (0.05 mL each site) with a lethal dose of CHIKV (10$^{2.5}$ TCID$_{50}$). All mice survived after prior infusion with the dose of 10 mg/kg or 2 mg/kg of the CHKV-24 mAb (FIG. 11). Half (50%) of animals treated with 0.4 mg/kg of mAb survived (FIG. 11). All animals treated with a control antibody mAb against influenza A virus died, whereas all unchallenged (naïve) animals survived (FIG. 11). Comparison of the survival experiments and the level of serum human IgG levels achieved suggested that the CHKV-24 IgG could protect AG129 mice in a lethal challenge model at systemic levels of 10 μg/mL of antibody at the time of challenge.

TABLE 1

NUCLEOTIDE SEQUENCES FOR ANTIBODY VARIABLE REGIONS

| Clone | Variable Sequence Region | SEQ ID NO: |
|---|---|---|
| ChikV-1_VH | CAGGTGCAGCTGGTGGAGTCGGGGGGAGGCGTGGTCCAGCCTGGGAGGTC CCTGAGACTCTCCTGTGCAGCCTCAGAATCCACCTTCAGCGGCTATGCTATGC ACTGGGTCCGCCAGGCTCCAGGCAAGGGGCTGGAGTGGGTGGCAGTCACAT CATATGATGGAAGTAGTAACTACTACGCAGACTCCGTGAGGGGCCGATTCAC CATTTTGAGAGACATTTCCAAGAACACGCTGTTTCTGCAAATGAACAGCCTGA GAGCTGAGGACACGGCTGTCTATTACTGTGTGAGGGAATATTACGGTCTGGA TGTCTGGGGCCGAGGGACCCTGGTCACCGTCTCCTCA | 2 |

TABLE 1-continued

NUCLEOTIDE SEQUENCES FOR ANTIBODY VARIABLE REGIONS

| Clone | Variable Sequence Region | SEQ ID NO: |
|---|---|---|
| ChikV-1_VL | GACATCCAGATGACCCAGTCTCCATCCTTCCTGTCTGCATCTGTAGGAGACAG<br>AGTCACCATCACTTGCCGGGCAGTCAGGGCATTAGCCGTTATTTAGCCTGGT<br>ATCAGCAAAAACCAGGGAAAGCCCCTAAACTCCTGATGTCTGTTCCATCCACT<br>TTACAAAGTGGGGTCCCATCAAGGTTCAGCGGCAGTGGATCTGGGACAGAAT<br>TCACTCTCACAATCAGCAGCCTACAGCCTGAAGATTTTGCAACTTATTACTGTC<br>AACACCTTAATGGTTACCCGTACTCTTTCGGCGGAGGGACCAAGGTGGAGAT<br>CAAA | 3 |
| ChikV-4_VH | CAGGTCCAGCTGGTACAGTCTGGGGCTGAGGTGAAGAAGCCTGGGGCCTCA<br>GTGAAGGTCTCCTGCAAGGTTTCCGGATACACCCTCACTGACTTATCCATGCA<br>CTGGGTGCGACAGGCCCCTGGAAAAGGGCTTGAGTGGATGGGAGGTTTTGA<br>TCCTGAAGATAGTGAAACAATCTACGCACAGAAGTTCCAGGGCAGAGTCACC<br>ATGACCGAGGACACATCTACAGATACAGCCTACATGGAGCTGAGCAGCCTGA<br>GATCTGACGACACGGCCGTCTATTACTGTGCAACAGAAAATTTCGATACTTTA<br>ATTGGTCATTATAAATTTGACTTCTGGGGCCAGGGAACCCTGGTCACCGTCTC<br>CTCA | 4 |
| ChikV-4_VL | GACATCCAGATGACCCAGTCTCCATCGTCCCTGTCTGCATCTGTAGGAGACAG<br>AGTCACCATCACTTGCCAGGCGAGTCAAGACATTAGCAACTATTTAAATTGGT<br>ATCAGCAGAAACCAGGGAAAGCCCCTAACCTCCTGATCCACGATGCATCCAA<br>TTTGGAAACAGGGGTCCCATCCAGGTTCAGTGGAAGTGGATCTGGGACACAT<br>TTTACTCTCACCATCAGCAGCCTGCAGCCTGAAGATATTGCAACATATTACTGT<br>CAACAGTATGATAATCTCCCTCGAACTTTCGGCCCTGGGACCAAAGTGGATAT<br>CAAA | 5 |
| ChikV-8_VH | GAAGTGCAGCTGGTGGAGTCTGGGGGAGGCTTGGTACAGCCTGGCAGGTCC<br>CTGAGACTCTCCTGTGCAGCCTCTGGATTCACCTTTGATGATTATGCCATGCAC<br>TGGGTCCGGCAAGGTCAGGGAAGGGCCTGGAGTGGGTCTCAGGAATTAGT<br>TGGAAAAGTGGCAGTATAGGCTATGCGGACTCTGTGAAGGGTCGATTCACCA<br>TCACCAGAGACAACGCCAAAAAGTCCCTATATCTGCAAATGAACAGTCTGAG<br>AGCTGAGGACACGGCCTTGTATTACTGTACAAAAGACGCGATCCCGTCATATT<br>GTGATAGTATCAGCTGCTATAGGGCGAATGGGAACTACGACTTTTTCGGTAT<br>GGACGCCTGGGGCCAAGGGACCCTGGTCACCGTCTCCTCA | 6 |
| ChikV-8_VL1 | GACATCCAGATGACCCAGTCTCCATCGTCCCTGTCTGCATCTGTAGGAGACAG<br>AGTCACCATCACTTGCCAGGCGAGTCAAGACATTAGCAACTATTTAAATTGGT<br>ATCAGCAGAAACCAGGGAAAGCCCCTAACCTCCTGATCCACGATGCATCCAA<br>TTTGGAAACAGGGGTCCCATCCAGGTTCAGTGGAAGTGGATCTGGGACACAT<br>TTTACTCTCACCATCAGCAGCCTGCAGCCTGAAGATATTGCAACATATTACTGT<br>CAACAGTATGATAATCTCCCTCGAACTTTCGGCCCTGGGACCAAAGTGGATAT<br>CAAA | 7 |
| ChikV-8_VL2 | TCCTATGAGCTGACTCAGCCACCCTCAGTGTCCGTGTCTGCAGGACAGACAGC<br>CACCATCACCTGCTCTGGAGATAAATTGGGGGATAAATATGCTTGCTGGTATC<br>AGCAGAAGCCAGGCCAGTCCCCTGTGCTGGTCATCTATCAAGATAGCCAACG<br>GCCCTCAGGGATCCCTGAGCGATTCTCTGGCTCCAACTCTGGGAACACAGCC<br>ACTCTGACCATCAGCGGGACCCAGGCTATGGATGAGGCTGACTATTACTGTC<br>AGGCGTGGGACAGCAGCGTGGTATTCGGCGGAGGGACCAAGCTGACCGTCC<br>TA | 1 |
| ChikV-9_VH | GAGGTGCAGCTGGTGGAGTCCGGGGGAGGCTTGGTCCAGCCGGGGAAGTC<br>CCTGAGACTCTCCTGTGCAGCCTCTGGAGTCACCTTTAGTGGTTTTCGGATGA<br>GCTGGGTCCGCCAGGCTCCCGGGAAGGGGCTGGAGTGGGTGGCCGACATTA<br>ACCAAGATGGAAGTGAGACGTACTATGTGGACTCTGTGAAGGGCCGATTCAC<br>CATCTCCAGAGACAACGCCAAGAACTCAGTGTTTCTGCTACTGAACAGTCTGA<br>GAGCCGTGGACACGGCTGTTTATTACTGTGCGAGAGTGGTGGGCCTTGTTGC<br>TTTTGATGTCTGGGGCCAAGGGACCCTGGTCACCGTCTCCTCA | 8 |
| ChikV-9_VL | NA | 9 |
| ChikV-12_VH | GAAGTGCAGCTGGTGGAGTCTGGGGGAGGCTTGGTTCAGCCTGGCAGGTCC<br>CTGAGACTCTCCTGTGCAGCCTCTGGATTCATGTTTGATGATTGTGCCATGCA<br>CTGGGTCCGGCAAGCTCCAGGGAAGGGCCTGGAGTGGGTCTCAGGTATTAA<br>TTGGGATAGTGCTAGAATAGACTATGCGGCCTCTCTGAAGGGCCGATTCACC<br>ATATCCAGAGACAACGCCAGGAACTCCCTATATCTGCAAATGAACAGTCTGC<br>GACCTGAGGACACGGCCTTGTATTACTGTGTAAAAGCCTCGGACCGTGGATA<br>TACTGGCTACGACACCTCTTTTGACTACTGGGGCCAGGGAACCCTGGTCACCG<br>TCTCCTCA | 10 |

TABLE 1-continued

NUCLEOTIDE SEQUENCES FOR ANTIBODY VARIABLE REGIONS

| Clone | Variable Sequence Region | SEQ ID NO: |
|---|---|---|
| ChikV-12_VL | CAGTCTGTGCTGACTCAGCCACCCTCAGCGTCTGGGACCCCCGGGCAGAGGG<br>TCACCATCTCTTGTTCTGGAAGCAGCTCCAACATCGGAAGGAATACTGTAAAC<br>TGGTACCAGCAACTCCCAGGAACGCCCCCCAAACTCCTCACCTATAGTAATAA<br>TCAGCGGCCCTCAGGGGTCCCTGACCGATTCTCTGGCTCCAAGTCTGGCACCT<br>CAGCCTCCCTGGCCATCAGTGGGCTGCAGTCTGAGGATGAGGCTGATTATTA<br>CTGTGCAGCATGGGATGACAGCCTGAGTGGGTATGTCTTCGGAACTGGGACC<br>AAGGTCACCGTCCTA | 11 |
| ChikV-13_VH | GAGGTGCAGCTGGTGGAGTCTGGGGGAGACCTGGTACAGCCGGGGGGGTC<br>CCTGAGACTCTCCTGTGTAGCCTCTGGATTCAGTTTTAGTAACTTTGCCATGAG<br>CTGGGTCCGCCAGGCTCCAGGGAAGGGGCTGGAGTGGGTCGCAGGAATTAG<br>TGGTAGTGGATCTAGCACATACCATGCGGCCGCCGTGCAGGGCCGGTTCACC<br>ATCTCCAGAGACAATTCCAAGAATACACTGTATCTGCAAATGGACAGCCTGA<br>GAGTCGACGACATGGCCATATATTATTGTACGAAAGATGCAGAGAATCAGTT<br>GCTATATTGGTTCGACCCCTGGGGCCAGGGAACCCTGGTCACCGTCTCCTCA | 12 |
| ChikV-13_VL | GACATCCAGATGACCCAGTCTCCATCCTCCCTGTCTTCATCTGTAGGAGACAG<br>AATCACAATCACTTGCCGGGCAAGTCGGAGCATCAGTATGTATGTAAATTGG<br>TATGTCCAGAGACCAGGGCACGCCCCAAAGCTCCTCATCTATGCTGCATCCAC<br>TTTGCAAACTGGAGTCCCGTCAAGGTTCAGTGGCAGTGGATCTGGGACAGAT<br>TTCACTCTCACCATCAGCAGTCTGCAACCTGAAGATTTTGCAATTTACTACTGT<br>CAACAGACTTACACTAACCCGACGTTCGGCCAGGGGACCAAGGTGGAAATCA<br>AA | 13 |
| ChikV-19_VH | CAGGTGCAGCTGCAGGAGTCGGGCCCAGGACTGGTGAAGCCTTCGGGGACT<br>CTGTCCCTCAGCTGCGCTGTCTCTGGTGGCTCCATCAGTAGTTATGACTGGTG<br>GAGTTGGGTCCGCCAGTTCCCAGGAAAGGGGCTGGAGTGGATTGGGGAAAT<br>CTATCATAGTGGGAGCACCAATTACAACCCGTCCCTCAAGAGTCGAGTCACCA<br>TTTCAGTAGACAAGTCCAACAACCAGTTCTCCCTGAACCTGACCTCTGTGACC<br>GCCGCGGACACGGCCGTCTATTACTGTGCGAGAGGCAATTTACAACGCCCCG<br>GGGTCTACTTCGGTTTGGACGTCTGGGGCCCAGGGACCCTGGTCACCGTCTC<br>CTCA | 14 |
| ChikV-19_VL | CAGTCTGCCCTGACTCAGCCTCCCTCCGCGTCCGGGTCTCCTGGACAGTCAGT<br>CACCATCTCCTGCACTGGAACCAGCAGTGACGTTGGTGGTTATAAATATGTCT<br>CCTGGTACCAACAGTACCCAGGCAAAGCCCCCACACTCATAATTTATGAGGTC<br>ACTGAACGGCCCTCAGGGGTCCCTGATCGCTTCTCTGGCTCCAAGTCTGGCAA<br>CACGGCCTCCCTGACCGTCTCTGGGCTCCAGGCTGAGGATGAGGCTGATTAT<br>TACTGCAGCTCCTATGCCGCCAACAACAATTTGCTTTTCGGCGGAGGGACCAA<br>GCTGACCGTCCTA | 15 |
| ChikV-22B_VH | CAGGTGCAGCTGCAGGAGTCGGGCCCAGGACTGGTGAAGCCTTCGGGGACT<br>CTGTCCCTCAGCTGCGCTGTCTCTGGTGGCTCCATCAGTAGTTATGACTGGTG<br>GAGTTGGGTCCGCCAGTTCCCAGGAAAGGGGCTGGAGTGGATTGGGGAAAT<br>CTATCATAGTGGGAGCACCAATTACAACCCGTCCCTCAAGAGTCGAGTCACCA<br>TTTCAGTAGACAAGTCCAACAACCAGTTCTCCCTGAACCTGACCTCTGTGACC<br>GCCGCGGACACGGCCGTCTATTACTGTGCGAGAGGCAATTTACAACGCCCCG<br>GGGTCTACTTCGGTTTGGACGTCTGGGGCCCAGGGACCCTGGTCACCGTCTC<br>CTCA | 16 |
| ChikV-22B_VL | CAGTCTGTGCTGACTCAGCCACCCTCAGCGTCTGGGACCCCCGGGCAGAGAG<br>TCAGCATTGCTTGTTCTGGAGGCAGCTTCAACATCGAAAATAACTATCTTTCCT<br>GGTACCAACAAGTCCCAGGAACGGCCCCCAAACTCCTCATCTATCACAATGAT<br>CAGCGGCCCTCAGAAGTCCCTGACCGATTCTCTGCCTCCAGGTCTGGCCCCTC<br>AGCCTCCCTGGCCATCAGTGGGCTCCGGTCCGAGGATGAGGCTCATTATTACT<br>GTGCAACATGGGATGACAGTCTGAGTGGTTGGGTGTTCGGCGGAGGGACCA<br>AGTTGACCGTCCTG | 17 |
| ChikV-23_VH | CAGGTGCAGCTGCAGGAGTCGGGCCCAGGACTGGTGAAGCCTTCGGGGACC<br>CTGTCCCTCACCTGCGCTGTCTCTGGTGGCTCCATCAGTAGTAGTTCGTGGTG<br>GAGTTGGGTCCGCCAGCCCCCAGGGAAGGGGCTGGAATGGATTGGAGAAAT<br>CTATTGGAGTGGGAGAACCAACTACAACCCGTCCCTCAGGAGTCGAGTCACC<br>ATATCAGTAGACAAGTCCAAGAACCAGTTCTCCCTGACGCTGATCTCTGTGAC<br>CGCCGCGGACACGGCCGTGTATTACTGTGCAAAAACTCCGGATACTGCTATG<br>GGCGAGGATGTTTTTGATATCTGGGGCCAAGGGACCCTGGTCACCGTCTCCT<br>CA | 18 |
| ChikV-23_VL | CAGTCTGTGCTGACTCAGCCACCCTCAGCGTCTGGGACCCCCGGGCAGACAG<br>TCACCATCTCTTGTTCTGGAAGCAACTCCAACCTCGGAAGTAATTATGTAGTCT<br>GGTACCAGCAGGTCCCAGGAACGGCCCCCAAACTCCTCATCTATAGGAATAA<br>TCAGCGCCCCTCCGGGGTCTCTGACCGATTCTCTGGCTCCAAGTCTGGCACCT<br>CAGCCTCCCTGGCCATCAGTGGGCTCCGGTCCGAGGATGAGGCTGATTATCA<br>CTGTGCAACATGGGATGACAGCCTGAGTGGTCGGGTGTTCGGCGGAGGAAC<br>CAAACTGACCGTCCTA | 19 |

TABLE 1-continued

NUCLEOTIDE SEQUENCES FOR ANTIBODY VARIABLE REGIONS

| Clone | Variable Sequence Region | SEQ ID NO: |
|---|---|---|
| ChikV-24_VH | CAGGTGCAGCTGGTGGAGTCTGGGGGAGGCGTGGTCCAGCCTGGGAAGTCC CTGAGACTCTCCTGTGCAGCCTCTGGATTCACCTTCCGTAACTATGGCATGCA CTGGGTCCGCCAGGCTCCAGGCAAGGGGCTGGACTGGGTGGCACTTATATCA TATGATGGAACTCATAAGTACTATAAAGACTCCCTGAAGGGCCGATTCACCAT CTCCAGAGACAATTTCCAGAACACAGTAGATCTGCAAATCAACAGCCTGAGA CCTGACGACACGGCTGTCTATTACTGTGCGAAAGAACTTGCGACTTCCGGAG TGGTTGAACCTCTTGACTCCTGGGGCCAGGGAACCCTGGTCACCGTCTCCTCA | 20 |
| ChikV-24_VL | GAAATTGTGTTGACGCAGTCTCCAGGCACCCTGTCTTTGTCTCCAGGGGAAA GAGCCACCCTCTCCTGCAGGGCCAGTCAGAGTCTTGTCAGCAGCTACTTCGGC TGGTACCAACAGAAGCGTGGCCAGTCTCCCAGGCCTCCTCATCTATGCTGCATC CACCAGGGCCACTGGCATCCCAGACAGGTTCAGTGGCAGTGGGTCTGGGAC AGACTTCACTCTCACCATCAGCAGACTGGAGCCTGAAGATTTTGCAGTGTATT ACTGTCAGCAGTATGGTAACACACCTTTCACTTTCGGCGGAGGGACCAAGGT GGAGATCAAA | 21 |
| ChikV-27_VH | CAGGTCCAACTTGTGCAGTCTGGGGCTGAGGTGAAGAAGCCTGGGGCCTCA GTGAAGGTTTCCTGCAAGCCTTCTGGATACAACTTCATTGACTATGCTATGCA TTGGGTGCGCCAGGCCCCCGGACAAAGGCTTGAGTGGATGGGATGGATCAA CGCCGCCAATGATAATAGAGAATATTCACAGAAGTTTCAGGGCAGAGTCACC CTTACTCGGGACACATCCGCGACCACAGCCTACATGGAGCTGAGCAGCCTGA CATTTGAAGACACGGCTGTGTATTACTGTGCGAGAGATCGGGTACTATGGT TCGGGGAGTCGGCGGCTGGTTCGACCCCTGGGGCCAGGGAACCCTGGTCAC CGTCTCCTCA | 22 |
| ChikV-27_VL | TCCTATGTGCTGACTCAGCCACCCTCGGTGTCAGTGGCCCCAGGAGAGACGG CCAGGATTACCTGTGGGGGAAACAACATTGGAAGTAAAAGTGTGCACTGGT ACCAGCAGAAGCCAGTCCAGGCCCCTGTGGTGGTCGTCTATGATGATAGCGA CCGGCCCCTCAGGGATCCCTGAGCGATTCTCTGGCTCCAACTCTGGGAACACG GCCACCCTGACCATCAGCAGGGTCGAAGCCGGGGATGAGGCCGACTATTACT GTCAGGTGTGGGATAGTAGTAGTAATCATCCGGTGTTCGGCGGAGGGACCA AGGTGGCCGTCCTA | 23 |
| ChikV-29_VH | GAAGTGCAGCTGGTGGAGTCTGGGGGAGTCGTGGTACAGCCTGGGGGGTCC CTGAGACTCTCCTGTGCAGCCTCTGGATTCAACTTTGATGATTATACCATGCAC TGGGTCCGTCAAGCTCCGGGGAAGGGCCTGGAGTGGGTCTCTCTTATTACTT GGGATGGTCTCAGCACATACTATGCAGACTCTATGAAGGGCCGATTCACCAT CTCCAGAGACAACAGCAAGGACTCCCTGTATCTGCAAATGGACAGTCTGAGA ACTGAGGACACCGCCTTCTATTATTGTGTAAGAGATATGGGCCCGGGGCAG TCCACTTCTACTTCTACGGTATGGACGTCTGGGGCCAAGGGACCCTGGTCACC GTCTCCTCA | 24 |
| ChikV-29_VL | CAGTCTGCCCTGACTCAGCCTGCCTCCGTGTCTGGGTCTCCTGGACAGTCGAT CACCATCTCCTGCACTGGAACCAGCAGTGATGTTGGGAATTATAACCTTGTCT CCTGGTACCAACAACACCCAGGCAAAGTCCCCAAACTCATCATTTATGAGGTC AGTAAGCGGCCCTCAGGGATTTCTAAGCGCTTCTCTGCCTCCAAGTCTGGCAA CACGGCCTCCCTGACAATCTCTGGGCTCCAGGCTGAGGACGAGGCTGATTAT TACTGCTGCTCATATGCTGGTAGTAGCGGGGTGTTCGGCGCAGGGACCAAGC TGACCGTCCTC | 25 |
| ChikV-31_VH | GAGGTGCAGCTGGTGGAGTCTGGGGGAGGCTTGGTACAGCCTGGGGGGTCC CTGAGACTCTCCTGTGCAGCCTCTGGATTCACCTTTAGCAATTATGCCATGAG CTGGGTCCGCCAGGCTCCAGGGAAGGGGCTGGAGTGGGTCTCAGGCATCAG TGGAAGTGGTAGAACCACATACTACAGACTCCGTGAAGGGCCGGTTCAAC ATCTCCAGAGACAACACCAAGAACACGCTGTTTCTGCAAATGAACAGCCTGA GAGCCGAGGACACGGCCGTATATTATTGTGTGAAAGATAGAGCTGGCTGGTT CGGGAACTACTTTGACTACTGGGGCCAGGGAACCCTGGTCACCGTCTCCTCA | 26 |
| ChikV-31_VL | GACATCCAGATGACCCAGTCTCCATCCTCACTGTCTGCATCTGTAGGAGACAG AGTCACCATCACTTGTCGGGCGAGTCAGGGCATTAGCAATTATTTAGCCTGGT TTCAGCAGAAACCAGGGAAAGCCCCTAAGTCCCTGATCTATGCTGCATCCAGT TTGCAAAGTGGGGTCCCATCAAAGTTCAGCGGCAGTAGATCTGGGACAAATT TCACTCTCACCATCAGCAGCCTGCAGCCTGAAGATTTTGCAACTTATTACTGCC AACAATATAATACTTACCCTCCGACGTTCGGCCAAGGGACCACGGTGGAAAT CAAA | 27 |
| ChikV-32_VH | CAGGTCCAGCTGGTGCAGTCTGGGGCTGAGGTGAAGAAGCCTGGGGCCTCA GTGAAGGTTTCCTGCAAGGCTTCTGGATACACCTTCACTACCTTTGCTATGCAT TGGGTGCGCCAGGCCCCCGGACAAGGGCTTGAGTGCATGGGATGGATCAAC ACTGCCAATGGTTACAAAATATTCACAGAAGTTCCAGGGCAGGGTCACCA TTACCAGCGACACATCCGCGAGCACAGCCTCCATGGAGCTGAGCAGCCTGAC ATCTAAAGACACGGCTGTTTATTACTGTGCGAGAGTTCAAGATTTCGGTCACT ACGAAGGGGATACGGCTACTGGGGCCAGGGAACCCTGGTCACCGTCTCCT CA | 28 |

TABLE 1-continued

NUCLEOTIDE SEQUENCES FOR ANTIBODY VARIABLE REGIONS

| Clone | Variable Sequence Region | SEQ ID NO: |
|---|---|---|
| ChikV-32_VL | CAGTCTGTGCTGACGCAGCCGCCCTCAGTGTCTGGGGCCCCAGGGCAGAGG GTCATCATCTCCTGCACTGGGAGCAGCTCCAACATCGGGGCAGGTTATGATG TACACTGGTACCAGCAACTTCCAGGAACAGCCCCCAAACTCCTCATCTATGGT AACAGCTATCGGCCCTCAGGGGTCCCTGACCGATTCTCTGGCTCCAGGTCTGG CACCTCAGCCTCCCTGGCCATCACTGGGCTCCAGGCTGAGGATGAGGCTGAT TATTACTGCCAGTCCCACGACAGCCTGAATGATTTTAATGTGTTCGGCAG TGGCACCAAGGTGACCGTCCTC | 29 |
| ChikV-35_VH | GAGGTGCAGCTGGTGGAGTCTGGGGGAGGCTTGGTACCGCCGGGGGGGTC CCTGAGAGTCTCCTGTGCAGCCTCTGGATTCACTTTAAGAAGTTATGTCATGG CCTGGGTCCGCCAGGCTCCAGGGAAGGGGCTGGAGTGGGTCTCAGGTATTA GTGGTGATGGTGATCACACATACTACGCAGACTCCGTGAAGGGCCGGTTCAC CATCTCCAGAGACAATTCCAAGAACACACTGTATCTGCAAATGCACAGCCTGA GAGCCGAGGACACGGCCCTGTATTACTGTGTGAAAGATTGGGGGATACGTG GGATCTACTACCCCTCCGGTATGGACGTCTGGGGCCAAGGGACCACGGTCAT CGTCTCCTCA | 30 |
| ChikV-35_VL | TCCCTTGAGCTGGCACAGCCACCCTCGGTGTCAGTGTCCCCAGGACAGACGG CCAGGATCACCTGCTCTGGAGATGGATTGCCACAGGCATATGCTTATTGGTAC CAAAAGAAGCCAGGCCAGGCCCCTGTGCCGTTAATATATAAAGACACTGAGA GGCCCTCAGGGATCCCTGAGCGATTCTCTGGCTCCAGCTCAGGGACAACAGT CACGTTGACCATCAGTGGAGTCCAGGCAGAAGACGAGGCTGACTATTACTGT CAATCTGCAGACAGCATTGGTACTAATGTTATATTCGGCGGAGGGACCAAGC TGACCGTCCTA | 31 |
| ChikV-48_VH | CAGGTGCAGCTGCAGGAGTCGGGCCCAGGACTGGTGAAGCCTTCACAGACC CTGTCCCTCACCTGCGCTGTCTCCGGTGGCTCCATCAGCAGTGGTGGTTACTC CTGGAGCTGGATCCGGCAGCCACCAGGGAAGGGACTGGAGTGGATTGGGTA TATCTATTACAGTGGGAGCACCTACTACAACCCGTCCCTCAAGAGTCGACTTA CCATATCTATGGACACGTCGAAGAACCACTTCTCCCTGAAGCTGAGCTCTGTG ACCGCCGCGGACACGGCCGTGTATTACTGTGCCACCGACTATTGTAGTAGTA CCAGCTGCAATACAGGGGCCCCTGTCAACTGGGGCCAGGGAACCCTGGTCAC CGTCTCCTCA | 32 |
| ChikV-48_VL | GACATCCAGTTGACCCAGTCTCCATCCTTCCTGTCTGCATCTGTAGGAGACAG AGTCACCATCACTTGCCGGGCCAGTCAGGGCATTAGCAGTTATTTAGCCTGGT ATCAGCAAAAACCAGGGAAAGCCCCTAAGCTCCTGATCAATGCTGCATCCACT TTGCAAAGTGGGGTCCCGTCAAGATTCAGCGGCAGTGGATCTGGGACAGAA TTCACTCTCACAATCAGCAGCCTGCAGCCTGAAGATTTTGCAACTTATTACTGT CAACAGTTTAATGCTTACCCGTACACTTTTGGCCAGGGGACCAAGCTGGAGA TCAAA | 33 |
| ChikV-50_VH | GAAGTGCAGCTGGTGGAGTCTGGGGGAGGCTTGGTACAGCCTGGCAGGTCC CTGAGACTCTCCTGTGCAGCCTCTGGATTTACCTTTGATGATTATGCCATGCAC TGGGTCCGGCAAGCTCCAGGGAAGGGCCTGGAGTGGGTCTCAGGTATTAGT TGGAATAGTGGTTTCATAGGCTATGCGGACTCTGTGAAGGGCCGATTCACCA TCTCCAGAGACAACGCCAAGAACTCCCTGTATCTGCAAATGAACAGTCTGAG AGCTGAGGACACGGCCTTGTATTACTGTGCAAAGGATTTGGGACGGGCGTAT AGCAGTGGCTGGTACCTCTTTGACTACTGGGGCCAGGGAACCCTGGTCACCG TCTCCTCA | 34 |
| ChikV-50_VL | TCCTATGTGCTGACTCAGCCACCCTCAGTGTCAGTGGCCCCAGGAAAGACGG CCAGGATTACCTGTGGGGGAAACAACATTGGAAGTAAAAGTGTGCACTGGT ATCAGCAGCTGCCAGGCCAGGCCCCTGTGCTGGTCGTCTATGATGATAGCGA CCGGCCCTCAGGGATCCCTGAGCGATTCTCTGGCTCCAACTCTGGGTACACG GCCACCCTGATTATCAGCAGGGTCGAAGCCGGGGATGAGGCCGACTATTACT GTCAGGTGTGGGATAGTACTAGTGATCATGCTTGTGTCTTCGGACCTGGAAC CAAGGTCACCGTCCTA | 35 |
| ChikV-53_VH | CAGCTGCAGCTGCAGGAGTCGGGCCCAGGACTGGTGAAGCCTTCGGAGACC CTGTCCCTCACCTGCACTGTCTCTGGTGGCTCCATCAGCAGTACTAGTCACTAC TGGGGCTGGATCCGCCAGCCCCAGGGAAGGGGCTGGAGTGGATTGGCAAT ATTTATTATAGTGGGAGCACCTACTACAAATCGTCCCTCAAGAGTCGAGTCGC CATATCAGTAGACACGTCCAAGAACCAGTTCTCCCTGAAGCTGAGCTCTGTGA CCGCCGCGGACACGGCCGTGTATTTCTGTGCGAGAGTAGTTGTAGGGGGGT ACTATGATAATAGAGGTTATTATAGAGGTCCCCCCACCCCTCTGTACTACTTTG ACTACTGGGGCCAGGGAACCCTGGTCACCGTCTCCTCA | 36 |

TABLE 1-continued

NUCLEOTIDE SEQUENCES FOR ANTIBODY VARIABLE REGIONS

| Clone | Variable Sequence Region | SEQ ID NO: |
|---|---|---|
| ChikV-53_VL | GACATCCAGATGACCCAGTCTCCATCTTCCGTGTCTGCATCTGTAGGAGACAG AGTCACCATCTCTTGTCGGGCGAGTCCGGGTATTAGCACCTGGTTAGCCTGGT ATCAGCAGAAACCAGGGAAAGCCCCTAAGCTCCTGATCTATGCTGTATCCAG TTTGCAAAGTGGGGTCCCATCAAGGTTCAGCGGCAGTGGATCTGGGACAGAT TTCACTCTCACCATCAGCAGCCTGCAGCCTGAGGATTTTGCAACTTACTATTGT CAACAGGCTAACAGTCTCTCGTGGACGTTCGGCCAAGGGACCAAGGTGGAA ATCAAA | 37 |

TABLE 2

PROTEIN SEQUENCES FOR ANTIBODY VARIABLE REGIONS

| Clone | Variable Sequence | SEQ ID NO: |
|---|---|---|
| ChikV-1_VH | QVQLVESGGGVVQPGRSLRLSCAASESTFSGYAMHWVRQAPGKGLEWVAVTSY DGSSNYYADSVRGRFTILRDISKNTLFLQMNSLRAEDTAVYYCVREYYGLDWGR GTLVTVSS | 38 |
| ChikV-1_VL | DIQMTQSPSFLSASVGDRVTITCRASQGISRYLAWYQQKPGKAPKLLMSVPSTLQ SGVPSRFSGSGSGTEFTLTISSLQPEDFATYYCQHLNGYPYSFGGGTKVEIK | 39 |
| ChikV-4_VH | QVQLVQSGAEVKKPGASVKVSCKVSGYTLTDLSMHWVRQAPGKGLEWMGGFD PEDSETIYAQKFQGRVTMTEDTSTDTAYMELSSLRSDDTAVYYCATENFDTLIGHY KFDFWGQGTLVTVSS | 40 |
| ChikV-4_VL | DIQMTQSPSSLSASVGDRVTITCQASQDISNYLNWYQQKPGKAPNLLIHDASNLE TGVPSRFSGSGSGTHFTLTISSLQPEDIATYYCQQYDNLPRTFGPGTKVDIK | 41 |
| ChikV-8_VH | EVQLVESGGGLVQPGRSLRLSCAASGFTFDDYAMHWVRQGPGKGLEWVSGISW KSGSIGYADSVKGRFTITRDNAKKSLYLQMNSLRAEDTALYYCTKDAIPSYCDSIS CYRANGNYDFFGMDAWGQGTLVTVSS | 42 |
| ChikV-8_VL1 | DIQMTQSPSSLSASVGDRVTITCQASQDISNYLNWYQQKPGKAPNLLIHDASNLE TGVPSRFSGSGSGTHFTLTISSLQPEDIATYYCQQYDNLPRTFGPGTKVDIK | 43 |
| ChikV-8_VL2 | SYELTQPPSVSVSAGQTATITCSGDKLGDKYACWYQQKPGQSPVLVIYQDSQRPS GIPERFSGSNSGNTATLTISGTQAMDEADYYCQAWDSSVVFGGGTKLTVL | 44 |
| ChikV-9_VH | EVQLVESGGGLVQPGKSLRLSCAASGVTFSGFRMSWVRQAPGKGLEWVADINQ DGSETYYVDSVKGRFTISRDNAKNSVFLLLNSLRAVDTAVYYCARVVGLVAFDVW GQGTLVTVSS | 45 |
| ChikV-9_VL | NA | 46 |
| ChikV-12_VH | EVQLVESGGGLVQPGRSLRLSCAASGFMFDDCAMHWVRQAPGKGLEWVSGIN WDSARIDYAASLKGRFTISRDNARNSLYLQMNSLRPEDTALYYCVKASDRGYTGY DTSFDYWGQGTLVTVSS | 47 |
| ChikV-12_VL | QSVLTQPPSASGTPGQRVTISCSGSSSNIGRNTVNWYQQLPGTPPKLLTYSNNQR PSGVPDRFSGSKSGTSASLAISGLQSEDEADYYCAAWDDSLSGYVFGTGTKVTVL | 48 |
| ChikV-13_VH | EVQLVESGGDLVQPGGSLRLSCVASGFSFSNFAMSWVRQAPGKGLEWVAGISGS GSSTYHAAAVQGRFTISRDNSKNTLYLQMDSLRVDDMAIYYCTKDAENQLLYWF DPWGQGTLVTVSS | 49 |
| ChikV-13_VL | DIQMTQSPSSLSSSVGDRITITCRASRSISMYVNWYVQRPGHAPKLLIYAASTLQT GVPSRFSGSGSGTDFTLTISSLQPEDFAIYYCQQTYTNPTFGQGTKVEIK | 50 |
| ChikV-19_VH | QVQLQESGPGLVKPSGTLSLSCAVSGGSISSYDWWSWVRQFPGKGLEWIGEIYH SGSTNYNPSLKSRVTISVDKSNNQFSLNLTSVTAADTAVYYCARGNLQRPGVYFGL DVWGPGTLVTVSS | 51 |
| ChikV-19_VL | QSALTQPPSASGSPGQSVTISCTGTSSDVGGYKYVSWYQQYPGKAPTLIIYEVTER PSGVPDRFSGSKSGNTASLTVSGLQAEDEADYYCSSYAANNNLLFGGGTKLTVL | 52 |
| ChikV-22B_VH | QVQLQESGPGLVKPSGTLSLSCAVSGGSISSYDWWSWVRQFPGKGLEWIGEIYH SGSTNYNPSLKSRVTISVDKSNNQFSLNLTSVTAADTAVYYCARGNLQRPGVYFGL DVWGPGTLVTVSS | 53 |

TABLE 2-continued

PROTEIN SEQUENCES FOR ANTIBODY VARIABLE REGIONS

| Clone | Variable Sequence | SEQ ID NO: |
|---|---|---|
| ChikV-22B_VL | QSVLTQPPSASGTPGQRVSIACSGGSFNIENNYLSWYQQVPGTAPKLLIYHNDQR PSEVPDRFSASRSGPSASLAISGLRSEDEAHYYCATWDDSLSGWVFGGGTKLTVL | 54 |
| ChikV-23_VH | QVQLQESGPGLVKPSGTLSLTCAVSGGSISSSSWWSWVRQPPGKGLEWIGEIYW SGRTNYNPSLRSRVTISVDKSKNQFSLTLISVTAADTAVYYCAKTPDTAMGEDVFDI WGQGTLVTVSS | 55 |
| ChikV-23_VL | QSVLTQPPSASGTPGQTVTISCSGSNSNLGSNYVVWYQQVPGTAPKLLIYRNNQR PSGVSDRFSGSKSGTSASLAISGLRSEDEADYHCATWDDSLSGRVFGGGTKLTVL | 56 |
| ChikV-24_VH | QVQLVESGGGVVQPGKSLRLSCAASGFTFRNYGMHWVRQAPGKGLDWVALISY DGTHKYYKDSLKGRFTISRDNFQNTVDLQINSLRPDDTAVYYCAKELATSGVVEPL DSWGQGTLVTVSS | 57 |
| ChikV-24_VL | EIVLTQSPGTLSLSPGERATLSCRASQSLVSSYFGWYQQKRGQSPRLLIYAASTRA TGIPDRFSGSGSGTDFTLTISRLEPEDFAVYYCQQYGNTPFTFGGGTKVEIK | 58 |
| ChikV-27_VH | QVQLVQSGAEVKKPGASVKVSCKPSGYNFIDYAMHWVRQAPGQRLEWMGWI NAANDNREYSQKFQGRVTLTRDTSATTAYMELSSLTFEDTAVYYCARDRGTMVR GVGGWFDPWGQGTLVTVSS | 59 |
| ChikV-27_VL | SYVLTQPPSVSVAPGETARITCGGNNIGSKSVHWYQQKPVQAPVVVVYDDSDRP SGIPERFSGSNSGNTATLTISRVEAGDEADYYCQVWDSSSNHPVFGGGTKVAVL | 60 |
| ChikV-29_VH | EVQLVESGGVVVQPGGSLRLSCAASGFNFDDYTMHWVRQAPGKGLEWVSLITW DGLSTYYADSMKGRFTISRDNSKDSLYLQMDSLRTEDTAFYYCVRDMGPGAVHF YFYGMDVWGQGTLVTVSS | 61 |
| ChikV-29_VL | QSALTQPASVSGSPGQSITISCTGTSSDVGNYNLVSWYQQHPGKVPKLIIYEVSKR PSGISKRFSASKSGNTASLTISGLQAEDEADYYCCSYAGSSGVFGAGTKLTVL | 62 |
| ChikV-31_VH | EVQLVESGGGLVQPGGSLRLSCAASGFTFSNYAMSWVRQAPGKGLEWVSGISGS GRTTYYTDSVKGRFNISRDNTKNTLFLQMNSLRAEDTAVYYCVKDRAGWFGNYF DYWGQGTLVTVSS | 63 |
| ChikV-31_VL | DIQMTQSPSSLSASVGDRVTITCRASQGISNYLAWFQQKPGKAPKSLIYAASSLQS GVPSKFSGSRSGTNFTLTISSLQPEDFATYYCQQYNTYPPTFGQGTTVEIK | 64 |
| ChikV-32_VH | QVQLVQSGAEVKKPGASVKVSCKASGYTFTTFAMHWVRQAPGQGLECMGWIN TANGYTKYSQKFQGRVTITSDTSASTASMELSSLTSKDTAVYYCARVQDFGHYEG GYGYWGQGTLVTVSS | 65 |
| ChikV-32_VL | QSVLTQPPSVSGAPGQRVIISCTGSSSNIGAGYDVHWYQQLPGTAPKLLIYGNSY RPSGVPDRFSGSRSGTSASLAITGLQAEDEADYYCQSHDSSLNDFNVFGSGTKVT VL | 66 |
| ChikV-35_VH | EVQLVESGGGLVPPGGSLRVSCAASGFTLRSYVMAWVRQAPGKGLEWVSGISG DGDHTYYADSVKGRFTISRDNSKNTLYLQMHSLRAEDTALYYCVKDWGIRGIYYP SGMDVWGQGTTVIVSS | 67 |
| ChikV-35_VL | SLELAQPPSVSVSPGQTARITCSGDGLPQAYAYWYQKKPGQAPVPLIYKDTERPS GIPERFSGSSSGTTVTLTISGVQAEDEADYYCQSADSIGTNVIFGGGTKLTVL | 68 |
| ChikV-48_VH | QVQLQESGPGLVKPSQTLSLTCAVSGGSISSGGYSWSWIRQPPGKGLEWIGYIYY SGSTYYNPSLKSRLTISMDTSKNHFSLKLSSVTAADTAVYYCATDYCSSTSCNTGA PVNWGQGTLVTVSS | 69 |
| ChikV-48_VL | DIQLTQSPSFLSASVGDRVTITCRASQGISSYLAWYQQKPGKAPKLLINAASTLQS GVPSRFSGSGSGTEFTLTISSLQPEDFATYYCQQFNAYPYTFGQGTKLEIK | 70 |
| ChikV-50_VH | EVQLVESGGGLVQPGRSLRLSCAASGFTFDDYAMHWVRQAPGKGLEWVSGIS WNSGFIGYADSVKGRFTISRDNAKNSLYLQMNSLRAEDTALYYCAKDLGRAYSS GWYLFDYWGQGTLVTVSS | 71 |
| ChikV-50_VL | SYVLTQPPSVSVAPGKTARITCGGNNIGSKSVHWYQQLPGQAPVLVVYDDSDRP SGIPERFSGSNSGYTATLIISRVEAGDEADYYCQVWDSTSDHACVFGPGTKVTVL | 72 |
| ChikV-53_VH | QLQLQESGPGLVKPSETLSLTCTVSGGSISSTSHYWGWIRQPPGKGLEWIGNIYY SGSTYYKSSLKSRVAISVDTSKNQFSLKLSSVTAADTAVYFCARVVVGGYYDNRGY YRGPPTPLYYFDYWGQGTLVTVSS | 73 |
| ChikV-53_VL | DIQMTQSPSSVSASVGDRVTISCRASPGISTWLAWYQQKPGKAPKLLIYAVSSLQ SGVPSRFSGSGSGTDFTLTISSLQPEDFATYYCQQANSLSWTFGQGTKVEIK | 74 |

TABLE 3

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| ChikV-1_VH | ESTFSGYA (75) | TSYDGSSN (76) | VREYYGLDV (77) |
| ChikV-4_VH | GYTLTDLS (78) | FDPEDSET (79) | ATENFDTLIGHYKFDF (80) |
| ChikV-8_VH | GFTFDDYA (81) | ISWKSGSI (82) | TKDAIPSYCDSISCYRANGNYDFFGMDA (83) |
| ChikV-9_VH | GVTFSGFR (84) | INQDGSET (85) | ARVVGLVAFDV (86) |
| ChikV-12_VH | GFMFDDCA (87) | INWDSARI (88) | VKASDRGYTGYDTSFDY (89) |
| ChikV-13_VH | GFSFSNFA (90) | ISGSGSST (91) | TKDAENQLLYWFDP (92) |
| ChikV-19_VH | GGSISSYDW (93) | IYHSGST (94) | ARGNLQRPGVYFGLDV (95) |
| ChikV-22B_VH | GGSISSYDW (96) | IYHSGST (97) | ARGNLQRPGVYFGLDV (98) |
| ChikV-23_VH | GGSISSSSW (99) | IYWSGRT (100) | AKTPDTAMGEDVFDI (101) |
| ChikV-24_VH | GFTFRNYG (102) | ISYDGTHK (103) | AKELATSGVVEPLDS (104) |
| CHKV-27_VH | GYNFIDYA (105) | INAANDNR (106) | ARDRGTMVRGVGGWFDP (107) |
| CHKV-29_VH | GFNFDDYT (108) | ITWDGLST (109) | VRDMGPGAVHFYFYGMDV (110) |
| CHKV-31_VH | GFTFSNYA (111) | ISGSGRTT (112) | VKDRAGWFGNYFDY (113) |
| CHKV-32_VH | GYTFTTFA (114) | INTANGYT (115) | ARVQDFGHYEGGYGY (116) |
| CHKV-35_VH | GFTLRSYV (117) | ISGDGDHT (118) | VKDWGIRGIYYPSGMDV (119) |
| CHKV-48_VH | GGSISSGGYS (120) | IYYSGST (121) | ATDYCSSTSCNTGAPVN (122) |
| CHKV-50_VH | GFTFDDYA (123) | ISWNSGFI (124) | AKDLGRAYSSGWYLFDY (125) |
| CHKV-53_VH | GGSISSTSHY (126) | IYYSGST (127) | ARVVGGYYDNRGYYRGPPTPLYYFDY (128) |

TABLE 4

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| ChiKV-1_VL | QGISRY (129) | VPS (130) | QHLNGYPYS (131) |
| ChiKV-4_VL | QDISNY (132) | DAS (133) | QQYDNLPRT (134) |
| ChiKV-8_VL-1 | QDISNY (135) | DAS (136) | QQYDNLPRT (137) |
| ChiKV-8_VL-2 | KLGDKY (138) | QDS (139) | QAWDSSVV (140) |
| ChikV-9_VL | TIGSKT (141) | DDS (142) | QVWDSVSDHAV (143) |
| ChikV-12_VL | SSNIGRNT (144) | SNN (145) | AAWDDSLSGYV (146) |
| ChikV-13_VL | RSISMY (147) | AAS (148) | QQTYTNPT (149) |
| ChikV-19_VL | SSDVGGYKY (150) | EVT (151) | SSYAANNNLL (152) |
| ChikV-22B_VL | SFNIENNY (153) | HND (154) | ATWDDSLSGWV (155) |
| ChikV-23_VL | NSNLGSNY (156) | RNN (157) | ATWDDSLSGRV (158) |
| ChikV-24_VL | QSLVSSY (159) | AAS (160) | QQYGNTPFT (161) |
| CHKV-27_VL | NIGSKS (162) | DDS (163) | QVWDSSNHPV (164) |
| CHKV-29_VL | SSDVGNYNL (165) | EVS (166) | CSYAGSSGV (167) |
| CHKV-31_VL | QGISNY (168) | AAS (169) | QQYNTYPPT (170) |
| CHKV-32_VL | SSNIGAGYD (171) | GNS (172) | QSHDSSLNDFNV (173) |

TABLE 4-continued

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| CHKV-35_VL | GLPQAY (174) | KDT (175) | QSADSIGTNVI (176) |
| CHKV-48_VL | QGISSY (177) | AAS (178) | QQFNAYPYT (179) |
| CHKV-50_VL | NIGSKS (180) | DDS (181) | QVWDSTSDHACV (182) |
| CHKV-53_VL | PGISTW (183) | AVS (184) | QQANSLSWT (185) |

TABLE 5

Antibody Characteristics

Genetic features of monoclonal antibodies

| | | Heavy chain genetic features | | | | | Light chain genetic features | | | | |
|---|---|---|---|---|---|---|---|---|---|---|---|
| Sl. No | Clone | V gene | % germ-line iden-tity | J gene | D gene | CDR-IMGT lengths | HCDR3 AA junction (SEQ ID NO:) | V gene | % germ-line iden-tity | J gene | CDR-IMGT lengths | LCDR3 AA junction (SEQ ID NO:) |
| 1 | CHKV-1 | V3-30*04 | 94 | J6*02 | D5-12*01 | 8.8.9 | CVREYYG LDVW (186) | VK1-9*01 | 95 | JK4*01 | 6.3.9 | CQHLNG YPYSF (204) |
| 2 | CHKV-4 | V1-24*01 | 97 | J4*02 | D3-9*01 | 8.8.16 | CATENFDTLY KFDFW (187) | VK1-33*01 | 96 | JK3*01 | 6.3.9 | CQQYDNL PRTF (205) |
| 3 | CHKV-8 | V3-9*01 | 97 | J6*02 | D2-2*02 | 8.8.28 | CTKDAIPSYCDS ISCYRANGNYD FFGMDAW (188) | VK1-33*01 | 98 | JK3*01 | 6.3.9 | CQQYDNL PRTF (206) |
| 4 | CHKV-9 | V3-7*01 | 92 | J3*01 | D2-15*01 | 8.8.11 | CARVVGLVA FDVW (189) | nd despite repeated attempts | | | | |
| 5 | CHKV-12 | V3-9*01 | 94 | J4*02 | D5-12*01 | 8.8.17 | CVKASDRGYTG YDTSFDYW (190) | VL1-44*01 | 98 | JL1*01 | 8.3.11 | CAAWDDSL SGYVF (207) |
| 6 | CHKV-13 | V3-23*04 | 90 | J5*02 | D2-2*02 | 8.8.14 | CTKDAENQLLY WFDPW (191) | VK1-39*01 | 90 | JK1*01 | 6.3.8 | CQQTYT NPTF (208) |
| 7 | CHKV-19 | V4-4*02 | 94 | J6*02 | D3-16*01 | 9.7.16 | CARGNLQRPGV YFGLDVW (192) | VL2-8*01 | 96 | JL2*01 | 9.3.10 | CSSYAANN NLLF (209) |
| 8 | CHKV-22 | V1-18*01 | 91 | J4*02 | D3-16*01 | 8.8.14 | CARAFRGGPNL PPDYW (193) | VL1-47*01 | 91 | JL3*02 | 8.3.11 | CATWDDSL SGWVF (210) |
| 9 | CHKV-23 | V4-4*02 | 95 | J3*02 | D5-18*01 | 9.7.15 | CAKTPDTAMGE DVFDIW (194) | VL1-47*01 | 96 | JL3*02 | 8.3.11 | CATWDDSL SGRVF (211) |
| 10 | CHKV-24 | V3-30*03 | 93 | J4*02 | D3-3*01 | 8.8.15 | CAKELATSGVVE PLDSW (195) | VK3-20*01 | 95 | JK4*01 | 7.3.9 | CQQYGNT PFTF (212) |
| 11 | CHKV-27 | V1-38-4*01 | 95 | J4*02 | D4-17*01 | 8.8.13 | We have a sequence and are in the process of confirming it. (196) | VL3-21*02 | 97 | JL3*02 | 6.3.11 | CQVWDSSS NHPVF (213) |
| 12 | CHKV-29 | V3-43*01 | 96 | J6*02 | D3-16*01 | 8.8.18 | CVRDMGPG AVHFYFYGM DVW (197) | VL2-23*02 | 97 | JL3*02 | 9.3.9 | CCSYAG SSGVF (214) |
| 13 | CHKV-31 | V3-23*04 | 95 | J4*02 | D6-19*01 | 8.8.14 | CVKDRAGWFGN YFDYW (198) | VK1-16*02 | 97 | JK1*01 | 6.3.9 | CQQYNTY PPTF (215) |
| 14 | CHKV-32 | V1-3*01 | 95 | J4*02 | D4-17*01 | 8.8.15 | CARVQDFGFIY EGGYGYW (199) | VL1-40*01 | 97 | JL6*01 | 9.3.12 | CQSHDSSLN DFNVF (216) |
| 15 | CHKV-35 | V3-23*04 | 93 | J6*02 | D1-26*01 | 8.8.17 | CVKDWGIRGIYY PSGMDVW (200) | VK1-33*01 | 98 | JK3*01 | 6.3.9 | CQQYDNL PRTF (217) |
| 16 | CHKV-48 | V4-30-4*07 | 97 | J4*02 | D2-2*02 | 10.7.17 | CATDYCSSTSCN TGAPVNW (201) | VK1-9*01 | 96 | JK2*01 | 6.3.9 | CQQFNA YPYTF (218) |
| 17 | CHKV-50 | V3-9*01 | 99 | J4*02 | D6-19*01 | 8.8.17 | CAKDLGRAYSSG WYLFDYW (202) | VL3-21*03 | 95 | JL1*01 | 6.3.12 | CQVWDS TSDHA CVF (219) |
| 18 | CHKV-53 | V4-39*07 | 96 | J4*02 | D3-22*01 | 10.7.27 | CARVVVGGYY DNRGYYRGPPT PLYYFDYW (203) | VK1-12*01 | 97 | JK1*01 | 6.3.9 | CQQANSL SWTF (220) |

TABLE 6

Neutralizing activity of CHKV-specific human mAbs

| MAb clone (CHKV-) | IC$_{50}$ FRNT* (ng/mL) against CHKV |
|---|---|
| 24 | 4 |
| 35 | 11 |
| 27 | 17 |
| 8 | 24 |
| 12 | 25 |
| 48 | 37 |
| 29 | 86 |
| 32 | 81 |
| 53 | 319 |
| 31 | 684 |
| 50 | 2,266 |
| 1 | > |
| 4 | > |
| 9 | > |
| 13 | > |
| 19 | > |
| 22 | > |
| 23 | > |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

"Antibodies: A Laboratory Manual," Cold Spring Harbor Press, Cold Spring Harbor, NY, 1988.
Abbondanzo et al., Am. J. Pediatr. Hematol. Oncol., 12(4), 480-489, 1990.
Allred et al., Arch. Surg., 125(1), 107-113, 1990.
Atherton et al., Biol. of Reproduction, 32, 155-171, 1985.
Austin et al., PLoS Pathog 8, e1002930, 2012.
Brehin, et al., Virology 371:185-195, 2008.
Brown et al., J Immunol. Meth., 12; 130(1); 111-121, 1990.
Campbell, In: Monoclonal Antibody Technology, Laboratory Techniques in Biochemistry and Molecular Biology, Vol. 13, Burden and Von Knippenberg, Eds. pp. 75-83, Amsterdam, Elsevier, 1984.
Capaldi et al., Biochem. Biophys. Res. Comm., 74(2):425-433, 1977.
CDC, Chikungunya in the Americas. (Atlanta, Ga.: US Department of Health and Human Services). world-wide-web at cdc.gov/chikungunya/geo/americas.html, 2014.
CDC, Chikungunya virus (Atlanta, GA: US Department of Health and Human Services). world-wide-web at cdc.gov/media/releases/2013/p1218-chikungunyas.html, 2013.
Christian et al., Proc Natl Acad Sci USA, 110:18662-18667, 2013.
Chu et al., Deciphering the protective role of adaptive immunity to CHIKV/IRES a novel candidate vaccine against Chikungunya in the A129 mouse model. Vaccine 31:3353-3360,2013.
Couderc et al., J. Infect. Dis. 200, 516-523, 2009.
De Jager et al., Semin. Nucl. Med. 23(2), 165-179, 1993.
Dholakia et al., J Biol. Chem., 264, 20638-20642, 1989.
Doolittle and Ben-Zeev, Methods Mol. Biol., 109; 215-237, 1999.
Edwards & Brown, J. Gen. Virol. 67 (Pt 2), 377-380, 1986.
Edwards et al., J. Gen. Virol. 67 (Pt 2), 377-380, 1986.
Fong et al., J. Virol. 88:14364-14379, 2014.
Fric et al., J. Infect. Dis. 207:319-322, 2013.
Gefter et al., Somatic Cell Genet., 3:231-236, 1977.
Goh et al., Clin. Immunol. 149:487-497, 2013.
Gulbis and Galand, Hum. Pathol. 24(12), 1271-1285, 1993.
Guo et al., Sci. Transl. Med. 3:99 ra85, 2001.
Hallengard, et al., J. Virol. 88:13333-13343, 2014.
Hawman et al., J. Virol. 87, 13878-13888, 2013.
Hong et al., J. Virol. 87:12471-12480, 2013.
Kam et al., EMBO Mol. Med. 4, 330-343, 2012b.
Kam et al., J. Virol. 86, 13005-13015, 2012a.
Kam et al., PLoS One 9, e95647, 2014.
Khatoon et al., Ann. of Neurology, 26, 210-219, 1989.
Kielian et al., Viruses 2:796-825, 2010.
King et al., J Biol. Chem., 269, 10210-10218, 1989.
Kohler and Milstein, Eur. J Immunol., 6, 511-519, 1976.
Kohler and Milstein, Nature, 256, 495-497, 1975.
Krause et al., J. Immunol. 187:3704-3711, 2011b.
Krause et al., J. Virol. 84:3127-3130, 2010.
Krause et al., J. Virol. 85:10905-10908, 2011a.
Krause et al., J. Virol. 86:6334-6340, 2012.
Kyte and Doolittle, J. Mol. Biol., 157(1):105-132, 1982.
Lanciotti & Valadere, Emerg Infect Dis 20, 2014.
Lee et al., PLoS Pathog. 7:e1002390, 2011.
Levitt et al., Vaccine 4, 157-162, 1986.
Lum et al., J. Immunol. 190:6295-6302, 2013.
Mainou et al., MBio 4, 2013.
Masrinoul et al., Virology 464-465, 111-117, 2014.
Messer et al., Proc. Natl. Acad. Sci. U.S.A 111:1939-1944, 2014.
Morrison et al., Am J Pathol, 178:32-40, 2011.
Nakamura et al., In: Enzyme Immunoassays: Heterogeneous and Homogeneous Systems, Chapter 27, 1987.
O'Shannessy et al., J Immun. Meth., 99, 153-161, 1987.
Paes et al., J. Am. Chem. Soc., 131:6952-6954, 2009.
Pal et al., J. Virol. 88:8213-8226, 2014.
Pal et al., PLoS Pathog 9, e1003312, 2013.
Persic et al., Gene 187:1, 1997
Potter and Haley, Meth. Enzymol., 91, 613-633, 1983.
Remington's Pharmaceutical Sciences, 15th Ed., 3:624-652, 1990.
R. C. Team, R Foundation for Statistical Computing, Vienna, Austria, 2014.
Schilte et al., PLoS Negl. Trop. Dis. 7:e2137, 2013.
Selvarajah et al., PLoS Negl. Trop. Dis. 7:e2423, 2013.
Sissoko et al., PLoS Negl. Trop. Dis. 3:e389, 2009.
Smith et al., J. Virol. 86, 2665-2675, 2012.
Smith et al., J. Virol. 88, 12233-12241, 2014.
Smith et al., J. Virol., 86:2665-2675, 2012.
Smith et al., MBio 4, e00873-00813, 2013a.
Smith et al., J. Infect. Dis. 207, 1898-1908, 2013b.
Staples et al., Clin. Infect. Dis., 49, 942-948, 2009.
Sun et al., Elife, 2:e00435, 2013.
Sun et al., J Steroid Biochem., 26(1):83-92, 1987.
Sun et al., J. Virol., 88:2035-2046, 2014.
Tang et al., J Biol. Chem., 271:28324-28330, 1996.
Thornburg et al., J. Clin. Invest., 123:4405-4409, 2013.
U.S. Pat. No. 3,817,837
U.S. Pat. No. 3,850,752

U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
Vander Veen et al., Anim Health Res Rev, 13:1-9, 2012.
Voss et al., Nature, 468:709-712, 2010.
Voss et al., Nature, 468:709-712, 2010.
Warter et al., J. Immunol., 186:3258-3264, 2011.
Warter et al., J. Immunol., 186:3258-3264, 2011.
Wawrzynczak & Thorpe, In: *Immunoconjugates, Antibody Conjugates In Radioimaging And Therapy Of Cancer*, Vogel (Ed.), NY, Oxford University Press, 28, 1987.
Yu et al., Nature 455:532-536, 2008.

What is claimed is:

1. A method of detecting a Chikungunya virus infection in a subject comprising:
   (a) contacting a sample from said subject with an antibody or antibody fragment comprising paired heavy and light chain CDR1-3 sequences set out below:
   SEQ ID NOS: 81-83 (heavy chain) and SEQ ID NOS: 135-137 (light chain);
   SEQ ID NOS: 81-83 (heavy chain) and SEQ ID NOS: 138-140 (light chain);
   SEQ ID NOS: 87-89 (heavy chain) and SEQ ID NOS: 144-146 (light chain);
   SEQ ID NOS: 102-104 (heavy chain) and SEQ ID NOS: 159-161 (light chain);
   SEQ ID NOS: 105-107 (heavy chain) and SEQ ID NOS: 162-164 (light chain);
   SEQ ID NOS: 108-110 (heavy chain) and SEQ ID NOS: 165-167 (light chain);
   SEQ ID NOS: 114-116 (heavy chain) and SEQ ID NOS: 171-173 (light chain);
   SEQ ID NOS: 117-119 (heavy chain) and SEQ ID NOS: 174-176 (light chain); or
   SEQ ID NOS: 120-122 (heavy chain) and SEQ ID NOS: 177-179 (light chain); and
   (b) detecting Chikungunya virus in said sample by binding of said antibody or antibody fragment to a Chikungunya virus antigen in said sample.

2. A method of treating a subject infected with Chikungunya virus or reducing the likelihood of infection of a subject at risk of contracting Chikungunya virus, comprising treating said subject with an antibody or antibody fragment comprising paired heavy and light chain CDR1-3 sequences set out below:
   SEQ ID NOS: 81-83 (heavy chain) and SEQ ID NOS: 135-137 (light chain);
   SEQ ID NOS: 81-83 (heavy chain) and SEQ ID NOS: 138-140 (light chain);
   SEQ ID NOS: 87-89 (heavy chain) and SEQ ID NOS: 144-146 (light chain);
   SEQ ID NOS: 102-104 (heavy chain) and SEQ ID NOS: 159-161 (light chain);
   SEQ ID NOS: 105-107 (heavy chain) and SEQ ID NOS: 162-164 (light chain);
   SEQ ID NOS: 108-110 (heavy chain) and SEQ ID NOS: 165-167 (light chain);
   SEQ ID NOS: 114-116 (heavy chain) and SEQ ID NOS: 171-173 (light chain);
   SEQ ID NOS: 117-119 (heavy chain) and SEQ ID NOS: 174-176 (light chain); or
   SEQ ID NOS: 120-122 (heavy chain) and SEQ ID NOS: 177-179 (light chain).

3. The method of claim 2, wherein the antibody or antibody fragment is encoded by paired light and heavy chain variable sequences as set forth below:

SEQ ID NOS: 1 or 7 and 6; SEQ ID NOS: 11 and 10; SEQ ID NOS: 21 and 20; SEQ ID NOS: 23 and 22; SEQ ID NOS: 25 and 24; SEQ ID NOS: 29 and 28; SEQ ID NOS: 31 and 30; or SEQ ID NOS: 33 and 32.

4. The method of claim 2, wherein the antibody or antibody fragment is encoded by light and heavy chain variable sequences having 95% identify to paired sequences at set out below:
SEQ ID NOS: 1 or 7 and 6; SEQ ID NOS: 11 and 10; SEQ ID NOS: 21 and 20; SEQ ID NOS: 23 and 22; SEQ ID NOS: 25 and 24; SEQ ID NOS: 29 and 28; SEQ ID NOS: 31 and 30; or SEQ ID NOS: 33 and 32.

5. The method of claim 2, wherein said antibody or antibody fragment comprises paired light and heavy chain variable sequences as set out below:
SEQ ID NOS: 44 or 43 and 42; SEQ ID NOS: 48 and 47; SEQ ID NOS: 58 and 57; SEQ ID NOS: 60 and 59; SEQ ID NOS: 62 and 61; SEQ ID NOS: SEQ ID NOS: 66 and 65; SEQ ID NOS: 68 and 67; or SEQ ID NOS: 70 and 69.

6. The method of claim 2, wherein said antibody or antibody fragment comprises light and heavy chain variable sequences having 95% identity to paired sequences as set out below:
SEQ ID NOS: 44 or 43 and 42; SEQ ID NOS: 48 and 47; SEQ ID NOS: 58 and 57; SEQ ID NOS: 60 and 59; SEQ ID NOS: 62 and 61; SEQ ID NOS: SEQ ID NOS: 66 and 65; SEQ ID NOS: 68 and 67; or SEQ ID NOS: 70 and 69.

7. The method of claim 2, wherein the antibody fragment is a recombinant scFv (single chain fragment variable) antibody, Fab fragment, F(ab')$_2$ fragment, or Fv fragment.

8. The method of claim 2, wherein said antibody is an IgG.

9. The method of claim 2, wherein said antibody is a chimeric antibody.

10. The method of claim 2, wherein said antibody or antibody fragment is administered prior to infection.

11. The method of claim 2, wherein said antibody or antibody fragment is administered after infection.

12. The method of claim 2, wherein delivering comprises antibody or antibody fragment administration, or genetic delivery with an RNA or DNA sequence or vector encoding the antibody or antibody fragment.

13. A hybridoma or engineered cell encoding an antibody or antibody fragment comprising paired heavy and light chain CDR1-3 sequences as set out below:
SEQ ID NOS: 81-83 (heavy chain) and SEQ ID NOS: 135-137 (light chain);
SEQ ID NOS: 81-83 (heavy chain) and SEQ ID NOS: 138-140 (light chain);
SEQ ID NOS: 87-89 (heavy chain) and SEQ ID NOS: 144-146 (light chain);
SEQ ID NOS: 102-104 (heavy chain) and SEQ ID NOS: 159-161 (light chain);
SEQ ID NOS: 105-107 (heavy chain) and SEQ ID NOS: 162-164 (light chain);
SEQ ID NOS: 108-110 (heavy chain) and SEQ ID NOS: 165-167 (light chain);
SEQ ID NOS: 114-116 (heavy chain) and SEQ ID NOS: 171-173 (light chain);
SEQ ID NOS: 117-119 (heavy chain) and SEQ ID NOS: 174-176 (light chain); or
SEQ ID NOS: 120-122 (heavy chain) and SEQ ID NOS: 177-179 (light chain).

14. The hybridoma or engineered cell of claim 13, wherein said antibody or antibody fragment is encoded by paired light and heavy chain variable sequences as set out below:
SEQ ID NOS: 1 or 7 and 6; SEQ ID NOS: 11 and 10; SEQ ID NOS: 21 and 20; SEQ ID NOS: 23 and 22; SEQ ID NOS: 25 and 24; SEQ ID NOS: 29 and 28; SEQ ID NOS: 31 and 30; or SEQ ID NOS: 33 and 32.

15. The hybridoma or engineered cell of claim 13, wherein said antibody or antibody fragment is encoded by light and heavy chain variable sequences having 95% identity to paired variable sequences as set out below:
SEQ ID NOS: 1 or 7 and 6; SEQ ID NOS: 11 and 10; SEQ ID NOS: 21 and 20; SEQ ID NOS: 23 and 22; SEQ ID NOS: 25 and 24; SEQ ID NOS: 29 and 28; SEQ ID NOS: 31 and 30; or SEQ ID NOS: 33 and 32.

16. The hybridoma or engineered cell of claim 13, wherein said antibody or antibody fragment comprises paired light and heavy chain variable sequences as set out below:
SEQ ID NOS: 44 or 43 and 42; SEQ ID NOS: 48 and 47; SEQ ID NOS: 58 and 57; SEQ ID NOS: 60 and 59; SEQ ID NOS: 62 and 61; SEQ ID NOS: SEQ ID NOS: 66 and 65; SEQ ID NOS: 68 and 67; or SEQ ID NOS: 70 and 69.

17. The hybridoma or engineered cell of claim 13, wherein said antibody or antibody fragment comprises light and heavy chain variable sequences having 95% identity to paired sequences as set out below:
SEQ ID NOS: 44 or 43 and 42; SEQ ID NOS: 48 and 47; SEQ ID NOS: 58 and 57; SEQ ID NOS: 60 and 59; SEQ ID NOS: 62 and 61; SEQ ID NOS: SEQ ID NOS: 66 and 65; SEQ ID NOS: 68 and 67; or SEQ ID NOS: 70 and 69.

18. A method of determining the antigenic integrity of an antigen comprising:
(a) contacting a sample comprising said antigen with a first antibody or antibody fragment comprising paired heavy and light chain CDR1-3 sequences as set out below:
SEQ ID NOS: 81-83 (heavy chain) and SEQ ID NOS: 135-137 (light chain);
SEQ ID NOS: 81-83 (heavy chain) and SEQ ID NOS: 138-140 (light chain);
SEQ ID NOS: 87-89 (heavy chain) and SEQ ID NOS: 144-146 (light chain);
SEQ ID NOS: 102-104 (heavy chain) and SEQ ID NOS: 159-161 (light chain);
SEQ ID NOS: 105-107 (heavy chain) and SEQ ID NOS: 162-164 (light chain);
SEQ ID NOS: 108-110 (heavy chain) and SEQ ID NOS: 165-167 (light chain);
SEQ ID NOS: 114-116 (heavy chain) and SEQ ID NOS: 171-173 (light chain);
SEQ ID NOS: 117-119 (heavy chain) and SEQ ID NOS: 174-176 (light chain); or
SEQ ID NOS: 120-122 (heavy chain) and SEQ ID NOS: 177-179 (light chain); and
(b) determining antigenic integrity of said antigen by detectable binding of said antibody or antibody fragment to said antigen.

19. The method of claim 1, wherein said sample is a body fluid.

20. The method of claim 1, wherein said sample is blood, sputum, tears, saliva, mucous or serum, urine or feces.

21. The method of claim 1, wherein detection comprises ELISA, RIA or Western blot.

22. The method of claim 1, further comprising performing steps (a) and (b) a second time and determining a change in the Chikungunya virus antigen levels as compared to the first assay.

23. The method of claim 1, wherein said antibody or antibody fragment is encoded by paired light and heavy chain variable sequences as set out below:

SEQ ID NOS: 1 or 7 and 6; SEQ ID NOS: 11 and 10; SEQ ID NOS: 21 and 20; SEQ ID NOS: 23 and 22; SEQ ID NOS: 25 and 24; SEQ ID NOS: 29 and 28; SEQ ID NOS: 31 and 30; or SEQ ID NOS: 33 and 32.

24. The method of claim 1, wherein said antibody or antibody fragment is encoded by light and heavy chain variable sequences having at least 95% identity to paired sequences as set out below:

SEQ ID NOS: 1 or 7 and 6; SEQ ID NOS: 11 and 10; SEQ ID NOS: 21 and 20; SEQ ID NOS: 23 and 22; SEQ ID NOS: 25 and 24; SEQ ID NOS: 29 and 28; SEQ ID NOS: 31 and 30; or SEQ ID NOS: 33 and 32.

25. The method of claim 1, wherein said antibody or antibody fragment comprises paired light and heavy chain variable sequences as set out below:

SEQ ID NOS: 44 or 43 and 42; SEQ ID NOS: 48 and 47; SEQ ID NOS: 58 and 57; SEQ ID NOS: 60 and 59; SEQ ID NOS: 62 and 61; SEQ ID NOS: SEQ ID NOS: 66 and 65; SEQ ID NOS: 68 and 67; or SEQ ID NOS: 70 and 69.

26. The method of claim 1, wherein said antibody or antibody fragment comprises light and heavy chain variable sequences having 95% identity to paired sequences as set out below:

SEQ ID NOS: 44 or 43 and 42; SEQ ID NOS: 48 and 47; SEQ ID NOS: 58 and 57; SEQ ID NOS: 60 and 59; SEQ ID NOS: 62 and 61; SEQ ID NOS: SEQ ID NOS: 66 and 65; SEQ ID NOS: 68 and 67; or SEQ ID NOS: 70 and 69.

27. The method of claim 1, wherein the antibody fragment is a recombinant scFv (single chain fragment variable) antibody, Fab fragment, F(ab')$_2$ fragment, or Fv fragment.

* * * * *

UNITED STATES PATENT AND TRADEMARK OFFICE
CERTIFICATE OF CORRECTION

PATENT NO. : 11,851,478 B2  
APPLICATION NO. : 16/959760  
DATED : December 26, 2023  
INVENTOR(S) : James E Crowe, Jr.

Page 1 of 1

It is certified that error appears in the above-identified patent and that said Letters Patent is hereby corrected as shown below:

In the Specification

In Column 1, Lines 15-20, please delete the paragraph and insert:
--This invention was made with government support under Grant Nos. AI103038, AI096833, AI057157, AI114816, and Contract No. HHSN272201400018C, awarded by the National Institutes of Health, and Contract Nos. W911NF-13-1-0417 and W31P4Q-13-1-0003, awarded by the Department of the Army. The Government has certain rights in the invention.-- therefor.

Signed and Sealed this  
Twenty-third Day of September, 2025

John A. Squires  
*Director of the United States Patent and Trademark Office*